United States Patent
Khakpour et al.

(10) Patent No.: US 9,877,801 B2
(45) Date of Patent: Jan. 30, 2018

(54) APPARATUS AND METHODS FOR FILLING TEETH AND ROOT CANALS

(71) Applicant: SONENDO, INC., Laguna Hills, CA (US)

(72) Inventors: Mehrzad Khakpour, Laguna Hills, CA (US); Bjarne Bergheim, Mission Viejo, CA (US)

(73) Assignee: SONENDO, INC., Laguna Hills, CA (US)

( * ) Notice: Subject to any disclaimer, the term of this patent is extended or adjusted under 35 U.S.C. 154(b) by 0 days.

(21) Appl. No.: 14/315,211

(22) Filed: Jun. 25, 2014

(65) Prior Publication Data

US 2015/0147718 A1    May 28, 2015

Related U.S. Application Data

(60) Provisional application No. 61/839,855, filed on Jun. 26, 2013, provisional application No. 61/866,420, (Continued)

(51) Int. Cl.
*A61C 5/02* (2006.01)
*A61C 17/02* (2006.01)
(Continued)

(52) U.S. Cl.
CPC ............... *A61C 5/02* (2013.01); *A61C 1/087* (2013.01); *A61C 5/40* (2017.02); *A61C 5/50* (2017.02);
(Continued)

(58) Field of Classification Search
CPC .... A61C 5/02; A61C 5/40; A61C 5/62; A61C 5/50; A61C 1/087; A61C 17/02; A61C 17/0202; A61C 17/20; A61C 17/028
See application file for complete search history.

(56) References Cited

U.S. PATENT DOCUMENTS

| 1,500,107 A | 7/1924 | Chandler |
|---|---|---|
| 2,108,558 A | 2/1938 | Jackman |

(Continued)

FOREIGN PATENT DOCUMENTS

| AU | 2012-202315 A1 | 4/2012 |
|---|---|---|
| AU | 2007140780 | 5/2014 |

(Continued)

OTHER PUBLICATIONS

Ahmad et al., "Ultrasonic Debridement of Root Canals: Acoustic Cavitation and Its Relevance," Journal of Endontics, vol. 14, No. 10, pp. 486-493, Oct. 1988.
(Continued)

*Primary Examiner* — Nicholas Lucchesi
(74) *Attorney, Agent, or Firm* — Knobbe, Martens, Olson & Bear LLP

(57) ABSTRACT

A dental apparatus is disclosed. The dental apparatus can comprise a pressure wave generator to be disposed at a treatment region of a tooth. The pressure wave generator can include an opening to deliver a flowable filling material to the treatment region. The apparatus can include a reservoir for supplying the filling material to the pressure wave generator. The pressure wave generator can be configured to generate pressure waves through the treatment region to cause the filling material to substantially fill the treatment region.

27 Claims, 16 Drawing Sheets

Related U.S. Application Data filed on Aug. 15, 2013, provisional application No. 61/873,789, filed on Sep. 4, 2013, provisional application No. 61/976,699, filed on Apr. 8, 2014, provisional application No. 61/982,223, filed on Apr. 21, 2014.

(51) Int. Cl.
| | |
|---|---|
| *A61C 1/08* | (2006.01) |
| *A61C 17/20* | (2006.01) |
| *A61C 5/40* | (2017.01) |
| *A61C 5/50* | (2017.01) |
| *A61C 5/62* | (2017.01) |
| A61C 17/028 | (2006.01) |

(52) U.S. Cl.
CPC ............... *A61C 5/62* (2017.02); *A61C 17/02* (2013.01); *A61C 17/0202* (2013.01); *A61C 17/20* (2013.01); *A61C 17/028* (2013.01)

(56) References Cited

U.S. PATENT DOCUMENTS

| | | |
|---|---|---|
| 3,023,306 A | 2/1962 | Kester |
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 2/1984 | Johnson, Jr. |
| 4,492,575 A | 1/1985 | Mabille |
| 4,534,542 A | 8/1985 | Russo |
| 4,539,987 A | 9/1985 | Nath et al. |
| 4,608,017 A | 8/1986 | Sadohara |
| 4,659,218 A | 4/1987 | de Lasa et al. |
| 4,661,070 A | 4/1987 | Friedman |
| 4,676,586 A | 6/1987 | Jones et al. |
| 4,676,749 A | 6/1987 | Mabille |
| 4,684,781 A | 8/1987 | Frish et al. |
| 4,732,193 A * | 3/1988 | Gibbs ................ A61C 17/0214 137/624.14 |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,985,027 A | 1/1991 | Dressel |
| 4,993,947 A | 2/1991 | Grosrey |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,055,048 A | 10/1991 | Vassiliadis et al. |
| 5,066,232 A | 11/1991 | Negri et al. |
| 5,094,256 A | 3/1992 | Barth |
| 5,112,224 A | 5/1992 | Shirota |
| 5,116,227 A | 5/1992 | Levy |
| 5,173,049 A | 12/1992 | Levy |
| 5,173,050 A | 12/1992 | Dillon |
| 5,188,532 A | 2/1993 | Levy |
| 5,188,634 A | 2/1993 | Hussein et al. |
| 5,194,723 A | 3/1993 | Cates et al. |
| 5,195,952 A | 3/1993 | Solnit et al. |
| 5,224,942 A | 7/1993 | Beuchat et al. |
| 5,267,856 A | 12/1993 | Wolbarst et al. |
| 5,267,995 A | 12/1993 | Doiron et al. |
| 5,269,777 A | 12/1993 | Doiron et al. |
| 5,292,253 A | 3/1994 | Levy |
| 5,295,828 A | 3/1994 | Grosrey |
| 5,307,839 A | 5/1994 | Loebker et al. |
| 5,322,504 A | 6/1994 | Doherty et al. |
| 5,324,200 A | 6/1994 | Vassiliadis et al. |
| 5,326,263 A | 7/1994 | Weissman |
| 5,334,019 A | 8/1994 | Goldsmith et al. |
| 5,380,201 A | 1/1995 | Kawata |
| 5,387,376 A | 2/1995 | Gasser |
| D356,866 S | 3/1995 | Meller |
| 5,399,089 A | 3/1995 | Eichman et al. |
| 5,428,699 A | 6/1995 | Pon |
| 5,435,724 A | 7/1995 | Goodman et al. |
| 5,474,451 A | 12/1995 | Dalrymple et al. |
| 5,490,779 A | 2/1996 | Malmin |
| 5,503,559 A | 4/1996 | Vari |
| 5,540,587 A | 7/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,639,239 A | 6/1997 | Earle |
| 5,642,997 A | 7/1997 | Gregg et al. |
| 5,643,299 A | 7/1997 | Bair |
| 5,660,817 A | 8/1997 | Masterman et al. |
| 5,662,501 A | 9/1997 | Levy |
| 5,674,226 A | 10/1997 | Doherty et al. |
| 5,688,486 A | 11/1997 | Watson et al. |
| 5,720,894 A | 2/1998 | Neev et al. |
| 5,730,727 A | 3/1998 | Russo |
| 5,735,815 A | 4/1998 | Bair |
| 5,740,291 A | 4/1998 | De Lasa et al. |
| 5,755,752 A | 5/1998 | Segal |
| 5,759,159 A | 6/1998 | Masreliez |
| 5,762,501 A | 6/1998 | Levy |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,820,373 A | 10/1998 | Okano et al. |
| 5,825,958 A | 10/1998 | Gollihar et al. |
| 5,839,896 A | 11/1998 | Hickok et al. |
| 5,842,863 A | 12/1998 | Bruns et al. |
| 5,846,080 A | 12/1998 | Schneider |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,897,314 A | 4/1999 | Hack et al. |
| 5,915,965 A | 6/1999 | Ohlsson et al. |
| 5,921,775 A | 7/1999 | Buchanan |
| 5,968,039 A | 10/1999 | Deutsch |
| 5,975,897 A | 11/1999 | Propp et al. |
| 5,989,023 A | 11/1999 | Summer et al. |
| 6,004,319 A | 12/1999 | Goble et al. |
| 6,019,605 A | 2/2000 | Myers |
| 6,053,735 A | 4/2000 | Buchanan |
| 6,079,979 A | 6/2000 | Riitano |
| 6,122,300 A | 9/2000 | Freiberg et al. |
| 6,129,721 A | 10/2000 | Kataoka et al. |
| 6,139,319 A | 10/2000 | Sauer et al. |

(56) References Cited

U.S. PATENT DOCUMENTS

| | | | |
|---|---|---|---|
| 6,143,011 A | 11/2000 | Hood et al. |
| 6,159,006 A | 12/2000 | Cook et al. |
| 6,162,052 A | 12/2000 | Kokubu |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |
| 6,190,318 B1 | 2/2001 | Bab et al. |
| 6,221,031 B1 | 4/2001 | Heraud |
| 6,224,378 B1 | 5/2001 | Valdes et al. |
| 6,227,855 B1 | 5/2001 | Hickok et al. |
| 6,245,032 B1 | 6/2001 | Sauer et al. |
| 6,282,013 B1 | 8/2001 | Ostler et al. |
| 6,288,499 B1 | 9/2001 | Rizoiu et al. |
| 6,290,502 B1 | 9/2001 | Hugo |
| 6,312,440 B1 | 11/2001 | Hood et al. |
| 6,315,557 B1 | 11/2001 | Messick |
| 6,343,929 B1 | 2/2002 | Fischer |
| 6,386,871 B1 | 5/2002 | Rossell |
| 6,390,815 B1 | 5/2002 | Pond |
| 6,428,319 B1 | 8/2002 | Lopez et al. |
| 6,440,103 B1 | 8/2002 | Hood et al. |
| 6,454,566 B1 | 9/2002 | Lynch et al. |
| 6,464,498 B1 | 10/2002 | Pond |
| 6,485,304 B2 | 11/2002 | Beerstecher et al. |
| 6,497,572 B2 | 12/2002 | Hood et al. |
| 6,511,493 B1 | 1/2003 | Moutafis et al. |
| 6,514,077 B1 * | 2/2003 | Wilk .................. A61C 17/20 433/119 |
| 6,527,766 B1 | 3/2003 | Bair |
| 6,538,739 B1 | 3/2003 | Visuri et al. |
| 6,562,050 B1 | 5/2003 | Owen |
| 6,572,709 B1 | 6/2003 | Kaneda et al. |
| 6,602,074 B1 | 8/2003 | Suh et al. |
| 6,616,447 B1 | 9/2003 | Rizoiu et al. |
| 6,638,219 B1 | 10/2003 | Asch et al. |
| 6,641,394 B2 | 11/2003 | Garman |
| 6,663,386 B1 | 12/2003 | Moelsgaard |
| 6,676,409 B2 | 1/2004 | Grant |
| 6,783,364 B1 | 8/2004 | Juan |
| 6,817,862 B2 | 11/2004 | Hickok |
| 6,821,272 B2 | 11/2004 | Rizoiu et al. |
| D499,486 S | 12/2004 | Kuhn et al. |
| 6,827,766 B2 | 12/2004 | Carnes et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,521 B2 | 3/2006 | Sierro et al. |
| 7,011,644 B1 | 3/2006 | Andrew et al. |
| 7,014,465 B1 | 3/2006 | Marais |
| 7,044,737 B2 | 5/2006 | Fu |
| 7,090,497 B1 | 8/2006 | Harris |
| 7,108,693 B2 | 9/2006 | Rizoiu et al. |
| 7,115,100 B2 | 10/2006 | McRury et al. |
| 7,147,468 B2 | 12/2006 | Snyder et al. |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,269,306 B1 | 9/2007 | Koeneman et al. |
| 7,270,544 B2 | 9/2007 | Schemmer et al. |
| 7,288,086 B1 | 10/2007 | Andriasyan |
| 7,296,318 B2 | 11/2007 | Mourad et al. |
| 7,306,459 B1 | 12/2007 | Williams et al. |
| 7,306,577 B2 | 12/2007 | Lemoine et al. |
| 7,326,054 B2 | 2/2008 | Todd et al. |
| 7,356,225 B2 | 4/2008 | Loebel |
| 7,384,419 B2 | 6/2008 | Jones et al. |
| 7,415,050 B2 | 8/2008 | Rizoiu et al. |
| 7,421,186 B2 | 9/2008 | Boutoussov et al. |
| 7,445,618 B2 | 11/2008 | Eggers et al. |
| 7,470,124 B2 | 12/2008 | Bornstein |
| 7,485,116 B2 | 2/2009 | Cao |
| 7,549,861 B2 | 6/2009 | Ruddle et al. |
| 7,620,290 B2 | 11/2009 | Rizoiu et al. |
| 7,630,420 B2 | 12/2009 | Boutoussov |
| 7,641,668 B2 | 1/2010 | Perry et al. |
| 7,670,141 B2 | 3/2010 | Thomas et al. |
| 7,695,469 B2 | 4/2010 | Boutoussov et al. |
| 7,696,466 B2 | 4/2010 | Rizoiu et al. |
| 7,702,196 B2 | 4/2010 | Boutoussov et al. |
| 7,748,979 B2 | 7/2010 | Nahlieli |
| 7,778,306 B2 | 8/2010 | Marincek et al. |
| 7,815,630 B2 | 10/2010 | Rizoiu et al. |
| 7,817,687 B2 | 10/2010 | Rizoiu et al. |
| 7,833,016 B2 | 11/2010 | Gharib et al. |
| 7,845,944 B2 | 12/2010 | DiGasbarro |
| 7,867,224 B2 | 1/2011 | Lukac et al. |
| 7,901,373 B2 | 3/2011 | Tavger |
| 7,909,817 B2 | 3/2011 | Griffin et al. |
| 7,916,282 B2 | 3/2011 | Duineveld et al. |
| 7,959,441 B2 | 6/2011 | Glover et al. |
| 7,970,027 B2 | 6/2011 | Rizoiu et al. |
| 7,970,030 B2 | 6/2011 | Rizoiu et al. |
| 7,980,854 B2 | 7/2011 | Glover et al. |
| 7,980,923 B2 | 7/2011 | Olmo et al. |
| 8,002,544 B2 | 8/2011 | Rizoiu et al. |
| 8,011,923 B2 | 9/2011 | Lukac et al. |
| 8,033,825 B2 | 10/2011 | Rizoiu et al. |
| 8,047,841 B2 | 11/2011 | Jefferies |
| 8,128,401 B2 | 3/2012 | Ruddle et al. |
| 8,152,797 B2 | 4/2012 | Boutoussov et al. |
| 8,204,612 B2 | 6/2012 | Feine et al. |
| 8,295,025 B2 | 10/2012 | Edel et al. |
| 8,298,215 B2 | 10/2012 | Zinn |
| 8,317,514 B2 | 11/2012 | Weill |
| 8,322,910 B2 | 12/2012 | Gansmuller et al. |
| 8,419,719 B2 | 4/2013 | Rizoiu et al. |
| 8,439,676 B2 | 5/2013 | Florman |
| 8,506,293 B2 | 8/2013 | Pond |
| 8,617,090 B2 | 12/2013 | Fougere et al. |
| D699,180 S | 2/2014 | Sweere et al. |
| 8,672,678 B2 | 3/2014 | Gramann et al. |
| 8,684,956 B2 | 4/2014 | McDonough et al. |
| 8,709,057 B2 | 4/2014 | Tettamanti et al. |
| 8,740,957 B2 | 6/2014 | Masotti |
| 8,747,005 B2 | 6/2014 | Kemp et al. |
| 8,753,121 B2 | 6/2014 | Gharib et al. |
| 8,758,010 B2 | 6/2014 | Yamanaka et al. |
| 8,801,316 B1 | 8/2014 | Abedini |
| 8,834,457 B2 | 9/2014 | Cao |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,025,625 B2 | 5/2015 | Skrabelj et al. |
| 9,050,157 B2 | 6/2015 | Boyd et al. |
| 9,101,377 B2 | 8/2015 | Boutoussov et al. |
| 9,186,222 B2 | 11/2015 | Marincek et al. |
| D745,966 S | 12/2015 | Piorek et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 9,492,244 B2 | 11/2016 | Bergheim et al. |
| 9,504,536 B2 | 11/2016 | Bergheim et al. |
| 9,572,632 B2 | 2/2017 | Lukac et al. |
| 9,579,174 B2 | 2/2017 | Yamamoto et al. |
| 9,610,125 B2 | 4/2017 | Kazic et al. |
| 2001/0041324 A1 | 11/2001 | Riitano |
| 2002/0012897 A1 | 1/2002 | Tingley et al. |
| 2002/0072032 A1 | 6/2002 | Senn et al. |
| 2002/0090594 A1 | 7/2002 | Riitano et al. |
| 2002/0108614 A1 | 8/2002 | Schultz |
| 2002/0183728 A1 | 12/2002 | Rosenberg et al. |
| 2003/0013064 A1 | 1/2003 | Zirkel |
| 2003/0096213 A1 | 5/2003 | Hickok et al. |
| 2003/0121532 A1 | 7/2003 | Coughlin et al. |
| 2003/0191429 A1 | 10/2003 | Andrew et al. |
| 2003/0207231 A1 | 11/2003 | Nance |
| 2003/0207232 A1 | 11/2003 | Todd et al. |

(56) References Cited

U.S. PATENT DOCUMENTS

| | | |
|---|---|---|
| 2003/0236517 A1 | 12/2003 | Appling |
| 2004/0038170 A1 | 2/2004 | Hiszowicz et al. |
| 2004/0048226 A1 | 3/2004 | Garman |
| 2004/0063074 A1 | 4/2004 | Fisher |
| 2004/0072122 A1 | 4/2004 | Hegemann |
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2004/0193236 A1 | 9/2004 | Altshuler |
| 2004/0210276 A1 | 10/2004 | Altshuler et al. |
| 2004/0224288 A1 | 11/2004 | Bornstein |
| 2004/0259053 A1 | 12/2004 | Bekov et al. |
| 2005/0064371 A1 | 3/2005 | Soukos et al. |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1 | 8/2005 | Pond |
| 2005/0199261 A1 | 9/2005 | Vanhauwemeiren et al. |
| 2005/0271531 A1 | 12/2005 | Brown et al. |
| 2005/0277898 A1 | 12/2005 | Dimalanta et al. |
| 2005/0281530 A1 | 12/2005 | Rizoiu et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0184071 A1 | 8/2006 | Klopotek |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0240386 A1 | 10/2006 | Yaniv et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0016177 A1 | 1/2007 | Vaynberg et al. |
| 2007/0016178 A1 | 1/2007 | Vaynberg et al. |
| 2007/0020576 A1 | 1/2007 | Osborn et al. |
| 2007/0042316 A1 | 2/2007 | Pichat et al. |
| 2007/0049911 A1 | 3/2007 | Brown |
| 2007/0072153 A1 | 3/2007 | Gross et al. |
| 2007/0083120 A1 | 4/2007 | Cain et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0265605 A1 | 11/2007 | Vaynberg et al. |
| 2007/0287125 A1 | 12/2007 | Weill |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0138772 A1 | 6/2008 | Bornstein |
| 2008/0155770 A1 | 7/2008 | Grez |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1 | 8/2008 | Teichert et al. |
| 2008/0255498 A1 | 10/2008 | Houle |
| 2008/0285600 A1 | 11/2008 | Marincek et al. |
| 2008/0311540 A1 | 12/2008 | Gottenbos et al. |
| 2009/0004621 A1 | 1/2009 | Quan et al. |
| 2009/0011380 A1 | 1/2009 | Wang |
| 2009/0042171 A1 | 2/2009 | Rizoiu et al. |
| 2009/0047624 A1 | 2/2009 | Tsai |
| 2009/0047634 A1 | 2/2009 | Calvert |
| 2009/0054881 A1 | 2/2009 | Krespi |
| 2009/0059994 A1 | 3/2009 | Nemes et al. |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | Divito et al. |
| 2009/0227185 A1 | 9/2009 | Summers et al. |
| 2009/0263759 A1 | 10/2009 | Van Herpern |
| 2010/0042040 A1 | 2/2010 | Arentz |
| 2010/0047734 A1 | 2/2010 | Harris et al. |
| 2010/0092922 A1 | 4/2010 | Ruddle |
| 2010/0143861 A1 | 6/2010 | Gharib |
| 2010/0152634 A1 | 6/2010 | Dove |
| 2010/0160838 A1 | 6/2010 | Krespi |
| 2010/0160904 A1 | 6/2010 | McMillan et al. |
| 2010/0209867 A1* | 8/2010 | Becker ............... A61C 5/02 433/32 |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0027747 A1 | 2/2011 | Fougere et al. |
| 2011/0070552 A1 | 3/2011 | Bornstein |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1 | 5/2011 | Bergheim et al. |
| 2011/0143310 A1 | 6/2011 | Hunter |
| 2011/0229845 A1 | 9/2011 | Chen |
| 2011/0256503 A1 | 10/2011 | Fraser |
| 2011/0269099 A1 | 11/2011 | Glover et al. |
| 2011/0270241 A1 | 11/2011 | Boutoussov |
| 2011/0281231 A1 | 11/2011 | Rizoiu et al. |
| 2012/0135373 A1 | 5/2012 | Cheng et al. |
| 2012/0141953 A1 | 6/2012 | Mueller |
| 2012/0148979 A1 | 6/2012 | Ruddle |
| 2012/0237893 A1 | 9/2012 | Bergheim |
| 2012/0276497 A1 | 11/2012 | Gharib |
| 2012/0282570 A1 | 11/2012 | Mueller |
| 2012/0021375 A1 | 12/2012 | Binner et al. |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0085486 A1 | 4/2013 | Boutoussov et al. |
| 2013/0131656 A1 | 5/2013 | Marincek et al. |
| 2013/0143180 A1 | 6/2013 | Glover et al. |
| 2013/0177865 A1 | 7/2013 | Ostler |
| 2013/0190738 A1 | 7/2013 | Lukac et al. |
| 2013/0216980 A1 | 8/2013 | Boronkay et al. |
| 2013/0236857 A1 | 9/2013 | Boutoussov et al. |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0080090 A1 | 3/2014 | Laufer |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1 | 5/2014 | Blaisdell et al. |
| 2014/0127641 A1 | 5/2014 | Hilscher et al. |
| 2014/0170588 A1 | 6/2014 | Miller et al. |
| 2014/0205965 A1 | 7/2014 | Boutoussov et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0261534 A1 | 9/2014 | Schepis |
| 2014/0272782 A1 | 9/2014 | Luettgen et al. |
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0017599 A1 | 1/2015 | Marincek et al. |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0056570 A1 | 2/2015 | Kansal |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147717 A1 | 5/2015 | Taylor et al. |
| 2015/0150650 A1 | 6/2015 | Netchitailo et al. |

(56) References Cited

U.S. PATENT DOCUMENTS

| | | |
|---|---|---|
| 2015/0173850 A1 | 6/2015 | Garrigues et al. |
| 2015/0173852 A1 | 6/2015 | Khakpour |
| 2015/0190597 A1 | 7/2015 | Zachar et al. |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib |
| 2015/0367142 A1 | 12/2015 | Kazic et al. |
| 2015/0374471 A1 | 12/2015 | Stangel et al. |
| 2016/0022392 A1 | 1/2016 | Chang et al. |
| 2016/0067149 A1 | 3/2016 | Kishen |
| 2016/0095679 A1 | 4/2016 | Khakpour |
| 2016/0100921 A1 | 4/2016 | Ungar |
| 2016/0113733 A1 | 4/2016 | Pond et al. |
| 2016/0128815 A1 | 5/2016 | Birdee et al. |
| 2016/0135581 A1 | 5/2016 | Pai |
| 2016/0149370 A1 | 5/2016 | Marincek et al. |
| 2016/0149372 A1 | 5/2016 | Marincek et al. |
| 2016/0324600 A1 | 11/2016 | Gharib |
| 2016/0367346 A1 | 12/2016 | Gharib |
| 2017/0027646 A1 | 2/2017 | DivVito et al. |
| 2017/0036253 A1 | 2/2017 | Lukac et al. |
| 2017/0056143 A1 | 3/2017 | Hyun |

FOREIGN PATENT DOCUMENTS

| | | |
|---|---|---|
| AU | 2011316839 | 8/2015 |
| CN | 102724929 | 10/2012 |
| CN | 103027762 A | 4/2013 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 0 902 654 | 8/2004 |
| EP | 2 498 713 | 9/2012 |
| EP | 2 821 027 | 1/2015 |
| EP | 2 836 156 | 2/2015 |
| EP | 2 836 157 | 2/2015 |
| EP | 2 934 364 | 10/2015 |
| EP | 2 951 019 | 12/2015 |
| EP | 3 013 277 | 5/2016 |
| FR | 1 225 547 | 7/1960 |
| FR | 2 831 050 | 10/2001 |
| GB | 917633 | 2/1963 |
| HK | 1 188 108 A | 4/2014 |
| IL | 219169 | 4/2013 |
| JP | 09-276292 | 10/1997 |
| JP | 10-33548 | 2/1998 |
| JP | 11-113927 A | 4/1999 |
| JP | 11-244303 A | 9/1999 |
| JP | 2000-254153 A | 9/2000 |
| JP | 2002-209911 | 7/2002 |
| JP | 2004-313659 | 11/2003 |
| JP | 3535685 B2 | 6/2004 |
| JP | 2004-261288 | 9/2004 |
| JP | 2005-095374 | 4/2005 |
| JP | 2007-533333 | 11/2007 |
| JP | 2008-93080 | 4/2008 |
| JP | 2008-132099 | 6/2008 |
| JP | 2009-114953 | 5/2009 |
| JP | 2013-510688 | 3/2013 |
| JP | 2013-544120 | 12/2013 |
| JP | 2015-510829 | 4/2015 |
| JP | 2015-512761 | 4/2015 |
| KR | 10-2008-0105713 A | 12/2008 |
| KR | 10-2012-0084897 A | 7/2012 |
| KR | 10-2013-0141103 A | 12/2013 |
| KR | 2004-72508 Y1 | 5/2014 |
| RU | 2326611 C1 | 12/2011 |
| WO | WO 1992/004871 | 4/1992 |
| WO | WO 1992/12685 | 8/1992 |
| WO | WO 1998/025536 | 6/1995 |
| WO | WO 1996/12447 | 5/1996 |
| WO | WO 1997/021420 | 6/1997 |
| WO | WO 1998/023219 | 6/1998 |
| WO | WO 2000/045731 | 8/2000 |
| WO | WO 2000/74587 | 12/2000 |
| WO | WO 2001/026577 | 4/2001 |
| WO | WO 2001/93773 | 12/2001 |
| WO | WO 2002/078644 | 10/2002 |
| WO | WO 2003/086223 | 10/2003 |
| WO | WO 2004/034923 | 4/2004 |
| WO | WO 2004/082501 | 9/2004 |
| WO | WO 2005/007008 | 1/2005 |
| WO | WO 2005/032393 | 4/2005 |
| WO | WO 2006/082101 | 8/2006 |
| WO | WO 2007/007335 | 1/2007 |
| WO | WO 2007/007336 | 1/2007 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/047670 | 4/2009 |
| WO | WO 2009/064947 | 5/2009 |
| WO | WO 2009/137815 | 11/2009 |
| WO | WO 2010/099538 | 9/2010 |
| WO | WO 2011/060327 | 5/2011 |
| WO | WO 2011/077291 | 6/2011 |
| WO | WO 2012/054905 | 4/2012 |
| WO | WO 2012/074918 | 6/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2013/160888 | 10/2013 |
| WO | WO 2014/100751 | 6/2014 |
| WO | WO 2014/121293 | 8/2014 |
| WO | WO 2015/168329 | 11/2015 |
| WO | WO 2016/005221 | 1/2016 |

OTHER PUBLICATIONS

DiVito et al.: "Cleaning and debriding efficacy of new radial and stripped tips using an Erbium laser on human root canal dentin walls—an in vitro study: SEM observations," undated.

ADA American Dental Association, "Glossary of Dental Clinical and Administrative Terms," http://www.ada.org/en/publications/cdt/glossary-of-dental-clinical-and-administrative-ter, downloaded May 4, 2017, in 46 pages.

Lukac et al.: "Photoacoustic Endodontics Using the Novel SWEEPS Er:YAG Laser Modality," Journal of the Laser and Health Academy, vol. 2017, No. 1; www.laserlaserandhealth.com.

Schoop et al., "The Impact of an Erbium, Chromium: yttrium-scandium-gallium-garnet laser with radial-firing tips on endonic treatment," Lasers in Medical Science, Springer-Verlag, LO. vol. 24, No. 1,, Nov. 20, 2007.

Stamos et al., "Retreatodontics and ultrasonics", Journal of Endodontics, vol. 14., No. 1, pp. 39-42, Jan. 1, 1988.

Stamos et al., "Use of ultrasonics in single-visit endodontic therapy," Journal of Endodontics, vol. 13, No. 5, pp. 246-249, May 1, 1987.

Zehnder, "Root Canal Irrigants", Journal of Endodontics, vol. 32, No. 5, pp. 389-398, May 2006.

European Extended Search Report, re EP Application No. 10830829.7, dated Oct. 21, 2015.

European Extended Search Report, re EP Application No. 13775073.3, dated Nov. 3, 2015.

International Preliminary Report on Patentability, re PCT Application No. PCT/US2014/036451, dated Nov. 3, 2015, 2015, in 11 pages.

International Search Report and Written Opinion dated Jan. 21, 2015, International Application No. PCT/US2014/044186 filed Jun. 25, 2014, 19 pages.

(56) References Cited

OTHER PUBLICATIONS

Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.
Al-Jadaa et al; Acoustic Hypochlorite Activation in Simulated Curved Canals; pp. 1408-1411; Journal of Endodontics, vol. 35, No. 10; Oct. 2009.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.
Anantharamaiah et al; A simple expression for predicting the inlet roundness of micro-nozzles; pp. N31-N39; Journal of Micromechanics and Microengineering, vol. 17; Mar. 21, 2007.
Anantharamaiah et al; A study on flow through hydroentangling nozzles and their degradation; pp. 4582-4594; Chemical Engineering Science, vol. 61; May 2006.
Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.
Attin et al; Clinical evaluation of the cleansing properties of the nonistrumental technique for cleaning root canals; pp. 929-933; International Endodontic Journal, vol. 35, Issue 11; Nov. 2002.
Batchelor et al; Analysis of the stability of axisymmetric jets; pp. 529-551; Journal of Fluid Mechanics, vol. 14; Dec. 1962.
Begenir et al; Effect of Nozzle Geometry on Hydroentangling Water Jets: Experimental Observations; pp. 178-184; Textile Research Journal, vol. 74; Feb. 2004.
Begenir, Asli; The Role of Orifice Design in Hydroentanglement; Thesis submitted to North Carolina State University; dated Dec. 2002, in 107 pages.
Borkent et al; Is there gas entrapped on submerged silicon wafers? Visualizing nano-scale bubbles with cavitation; pp. 225-228; Solid State Phenomena, vol. 134 (2008); available online Nov. 2007.
Bremond et al; Cavitation on surfaces; pp. S3603-S3608; Journal of Physics: Condensed Matter, vol. 17; Oct. 28, 2005.
Brennen, Christopher E.; Fission of collapsing cavitation bubbles; pp. 153-166; Journal of Fluid Mechanics, vol. 472; Dec. 2002.
Chang et al; Effects of Inlet Surface Roughness, Texture, and Nozzle Material on Cavitation; pp. 299-317; Atomization and Sprays, vol. 16 (2006).
Culjat et al., "B-Scan Imaging of Human Teeth Using Ultrasound," Apr. 2003, in 4 pages.
Didenkulov et al; Nonlinear Acoustic Diagnostics of Scatterer Spatial Distribution in a Cavitation Jet; Nov. 19-23, 2001, pp. 276-278, XI Session of the Russion Acoustical Society.
Dumouchel, Christophe; On the experimental investigation on primary atomization of liquid streams; pp. 371-422; Experimental Fluids, vol. 45; Jun. 22, 2008.
Eddingfield et al; Mathematical Modeling of High Velocity Water Jets; pp. 25-39; Proceedings of 1st U.S. Water Jet Conference; 1981.
EMS Electro Medical Systems, "Cleaning", in 2 pages, dated 2005, downloaded from http://www.ems-dent.com/en/endodontics cleaning. htm.
ESI Endo Soft Instruments, EMS Electro Medical Systems, Brochure in 2 pages, downloaded from www.emsdent.com, dated Jan. 2004.
European Extended Search Report re EP Application No. 09743801.4, dated Jun. 4, 2012.
European Extended Search Report, dated Sep. 22, 2011, for EP Application No. 07755777.5., in 7 pages.
European Extended Search Report, re EP Application No. 08728345.3, dated Mar. 3, 2014.
Feng et al; Enhancement of ultrasonic cavitation yield by multi-frequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; pp. e1457-e1460; Ultrasonics vol. 44 (Supplement 1); Jun. 8, 2006.
Fuchs, "Ultrasonic Cleaning: Fundamental Theory and Application," Blackstone-Ney Ultrasonics, Jamestown, NY, May 2002.
G.E. Reisman and C.E. Brennen, "Pressure Pulses Generated by Cloud Cavitation", FED—vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hungarian Written Opinion and Search Report via/re Singapore Application No. 189554, dated Oct. 13, 2013.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
International Preliminary Report and Written Opinion dated Nov. 9, 2010 for International Appl. No. PCT/US09/43386, in 6 pages.
International Preliminary Report on Patentability dated Aug. 6, 2009, for International Appl. No. PCT/US08/52122, in 13 pages.
International Preliminary Report on Patentability dated Oct. 30, 2008, for International Appl. No. PCT/US07/09633, in 5 pages.
International Preliminary Report on Patentability re App. No. PCT/US2010/056620, dated May 15, 2012, in 10 pages.
International Preliminary Report on Patentability, re PCT Application No. PCT/US11/57401, dated Jan. 25, 2013 in 13 pages.
International Search Report and Written Opinion dated Apr. 11, 2008, for International Appl. No. PCT/US07/09633, in 8 pages.
International Search Report and Written Opinion dated Aug. 8, 2008, for International Appl. No. PCT/US08/52122, in 18 pages.
International Search Report and Written Opinion dated Jul. 29, 2009, for International Appl. No. PCT/US09/43386, in 8 pages.
International Search Report and Written Opinion from International Application No. PCT/US2011/057401, dated Jan. 30, 2012, in 20 pages.
International Search Report and Written Opinion dated Jun. 28, 2013, re PCT Application No. PCT/US2013/036493, in 21 pages.
International Search Report and Written Opinion re App. No. PCT/US2010/056620, dated Jan. 12, 2011, in 17 pages.
International Search Report and Written Opinion, re PCT Application No. PCT/US 13/32635, dated Jun. 17, 2013 in 14 pages.
International Search Report and Written Opinion, re PCT Application No. PCT/US2013/077286, dated May 27, 2014.
Jackson et al; Nozzle Design for Coherent Water Jet Production; pp. 53-89; Proceeding of the 2nd US Water Jet Conference; May 1983.

(56) References Cited

OTHER PUBLICATIONS

Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; In CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc ., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sabeti, "Healing of apical periodontitis after endodontic treatment with and without obturation in dogs," Journal of Endodontics, Jul. 2006, pp. 628-633.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
European Extended Search Report re EP Application No. 14187012.1, dated Mar. 3, 2015, in 10 pages.
International Preliminary Report on Patentability and Written Opinion, dated Oct. 14, 2014, re PCT Application No. PCT/US2013/036493, in 14 pages.
International Preliminary Report on Patentability re PCT Application No. PCT/US2014/014732, dated Aug. 4, 2015.
International Preliminary Report on Patentability, re PCT Application No. PCT/US2013/077286, dated Jun. 23, 2015.
International Search Report and Written Opinion re App. No. PCT/US2014/014732, dated Jul. 18, 2014.
International Search Report and Written Opinion, re PCT Application No. PCT/US2014/036451, dated Jan. 21, 2015, in 20 pages.
International Search Report and Written Opinion, re PCT Application No. PCT/US2015/028360, dated Sep. 28, 2015, in 24 pages.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
European Extended Search Report, re EP Application No. 11835265.7, dated Mar. 30, 2016, in 9 pages.
European Extended Search Report, re EP Application No. 13763534.8, dated Jan. 15, 2016.
International Preliminary Report on Patentability, re PCT Application No. PCT/US2014/044186, dated Dec. 29, 2015, in 19 pages.
Wohlemuth et al.: "Effectiveness of Gentle Wave System in Removing Separated Instruments," JOE, vol. 41, No. 11, Nov. 2015.
Ebihara et al.: "Er:YAG laser modification of root canal dentine: Influence of pulse duration, repetitive irradiation and water spray," Lasers in Medical Science, 17(3), 198-207, Aug. 2002.
Nammour et al.: "External temperature during KTP-nd:YAG laser irradiation in root canals: An in vitro study," Lasers in Medical Science, 19(1), 27-32, Jul. 2004.

(56) References Cited

OTHER PUBLICATIONS

Ulrich Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.
U.S. Appl. No. 15/478,039, filed Apr. 3, 2017, Khakpour et al.
U.S. Appl. No. 15/499,757, filed Apr. 27, 2017, DiVito et al.

* cited by examiner

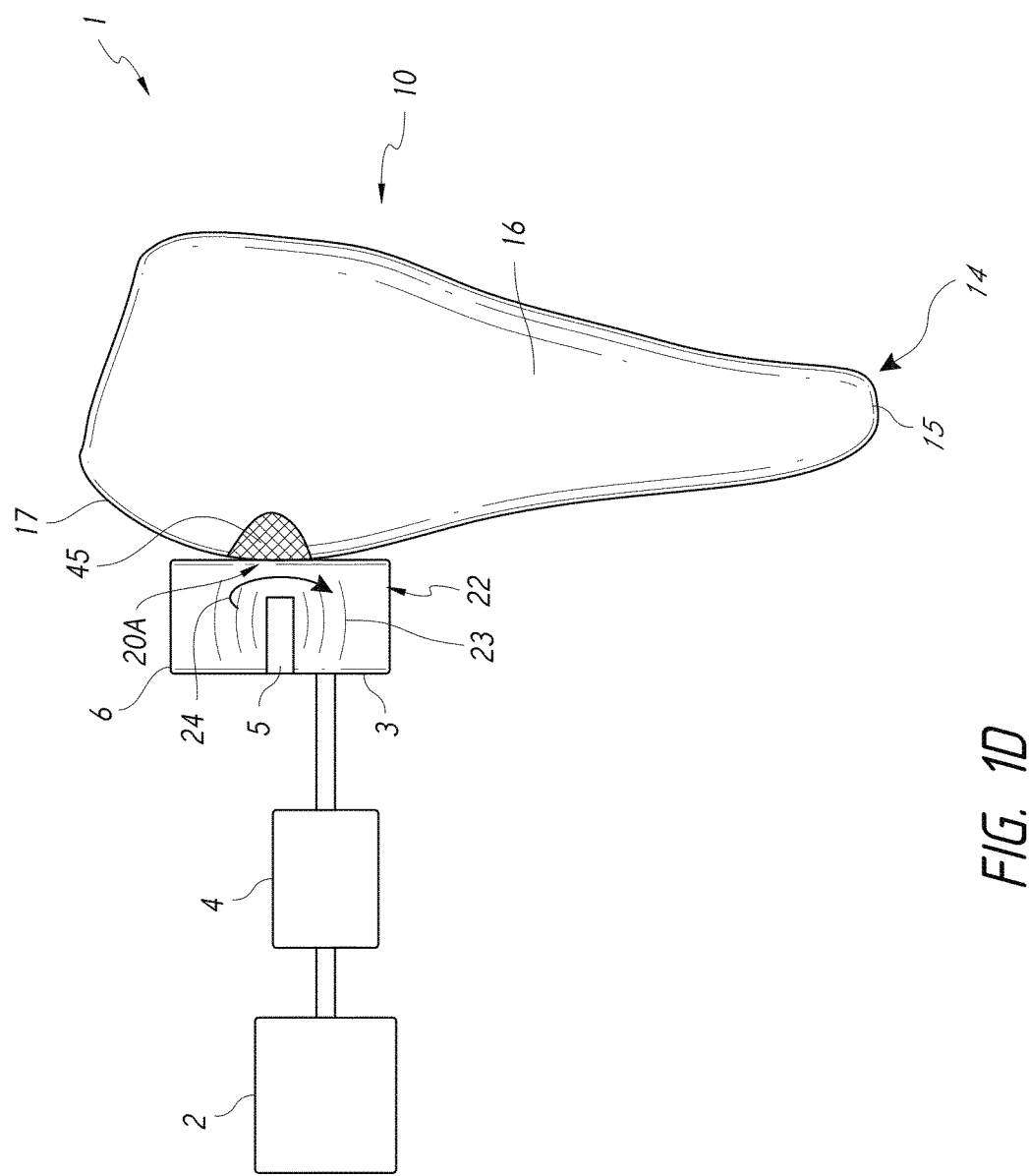

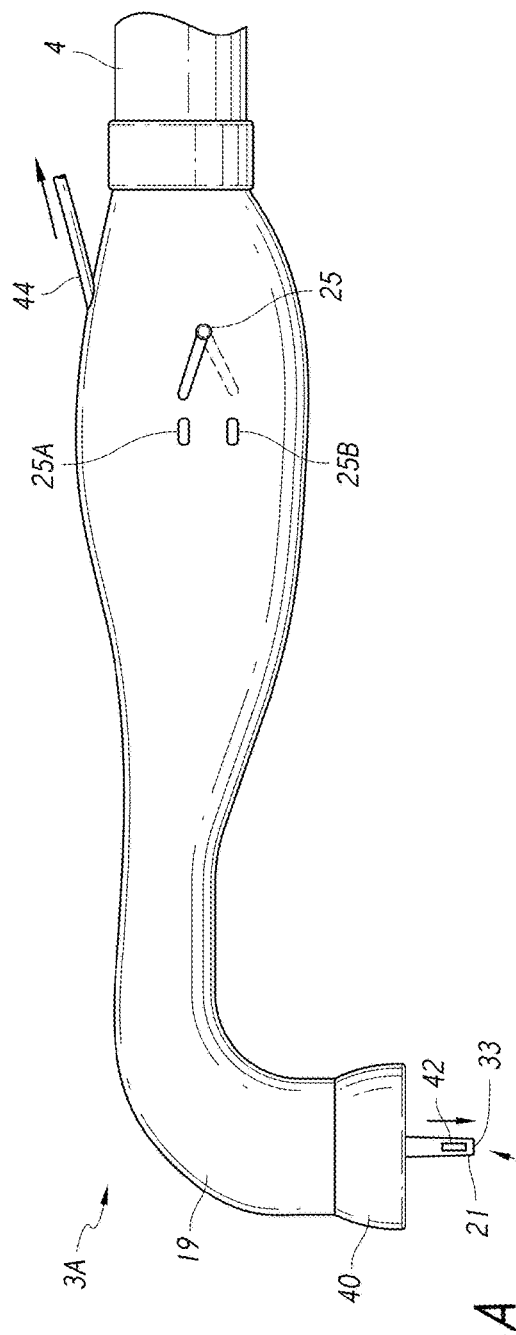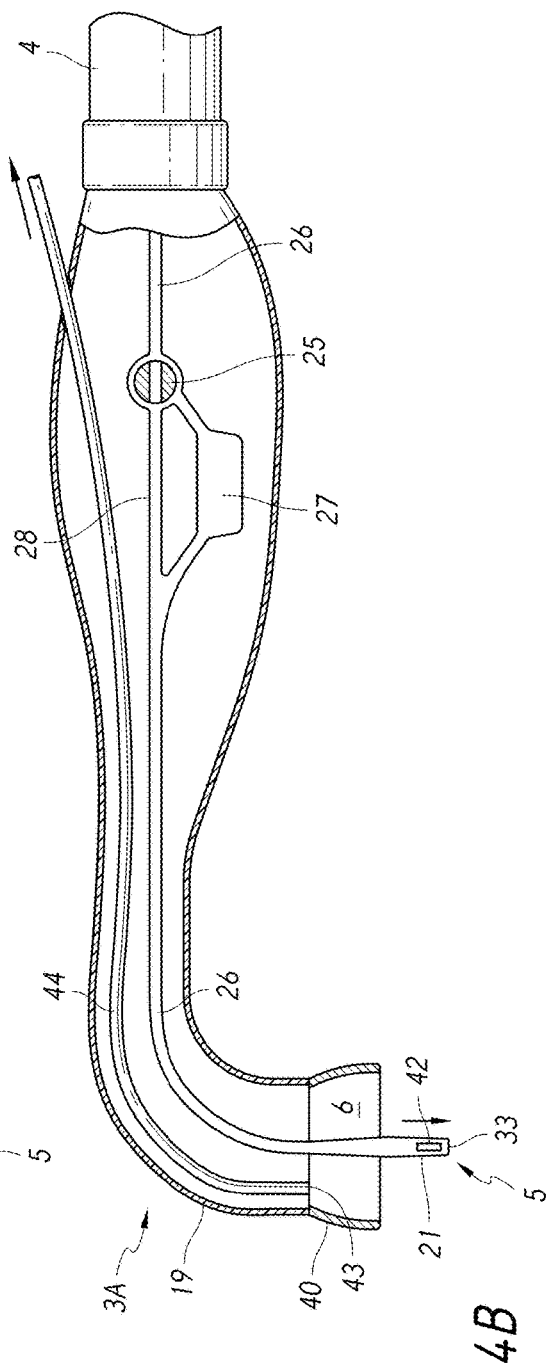
FIG. 4A
FIG. 4B

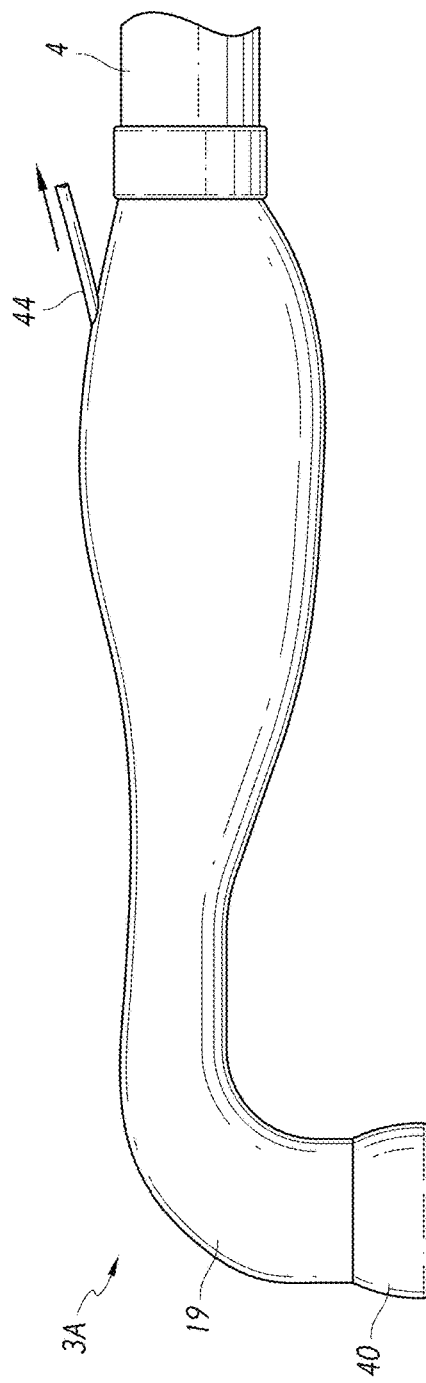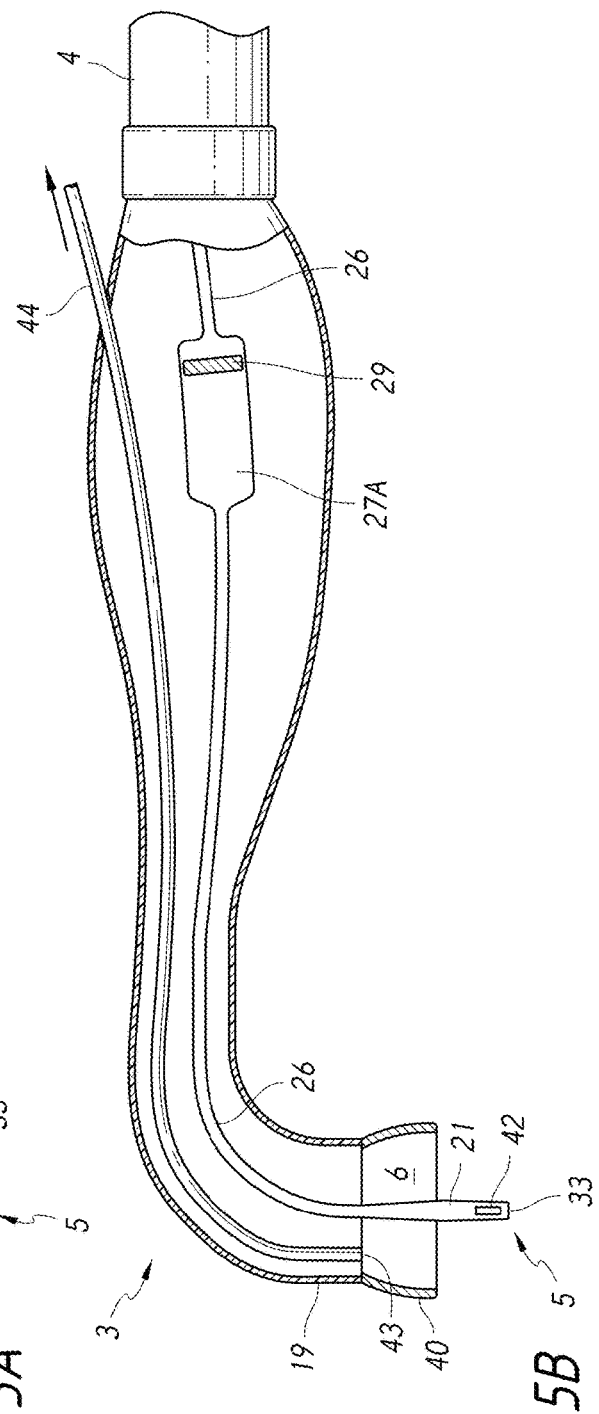
FIG. 5A
FIG. 5B

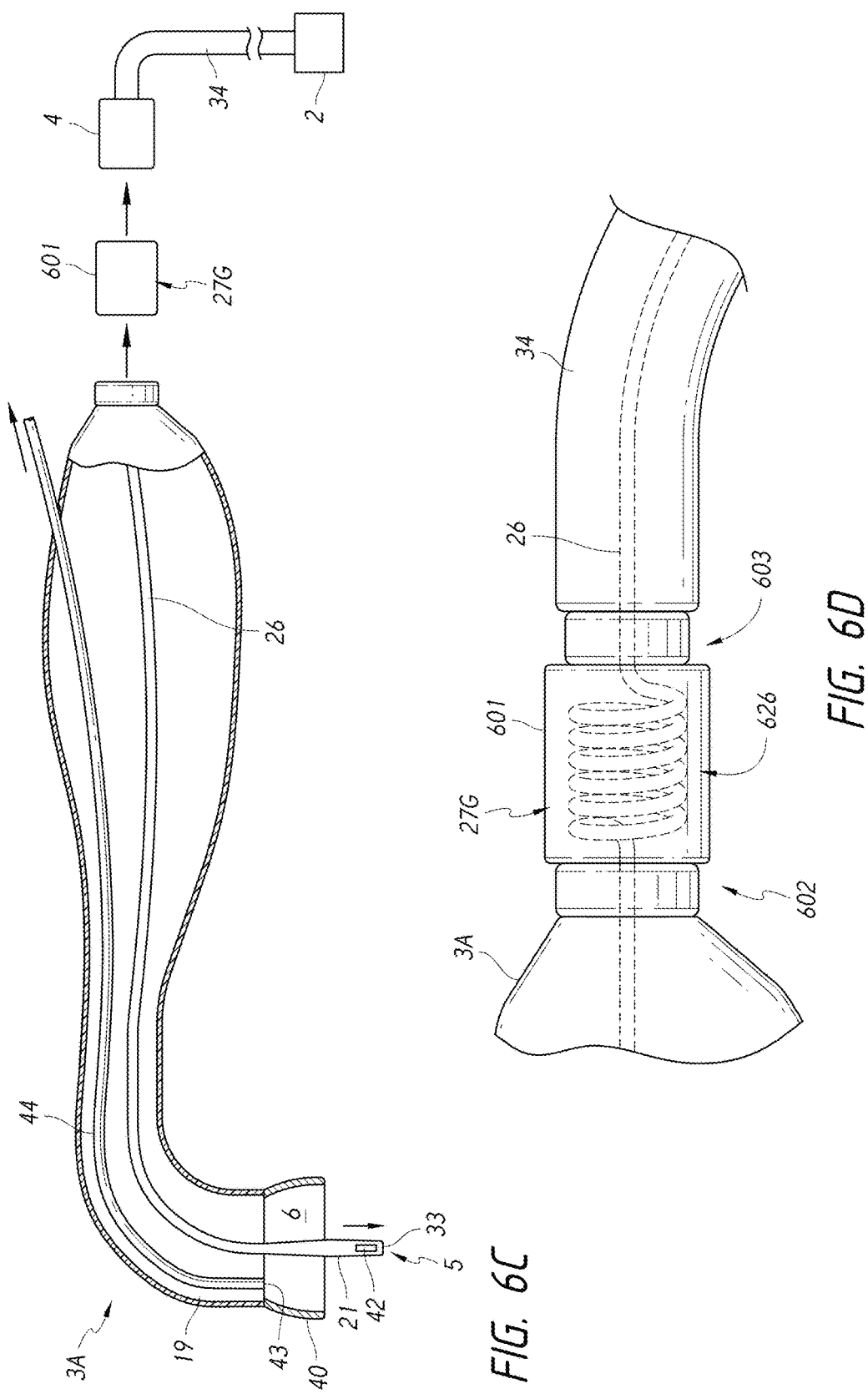

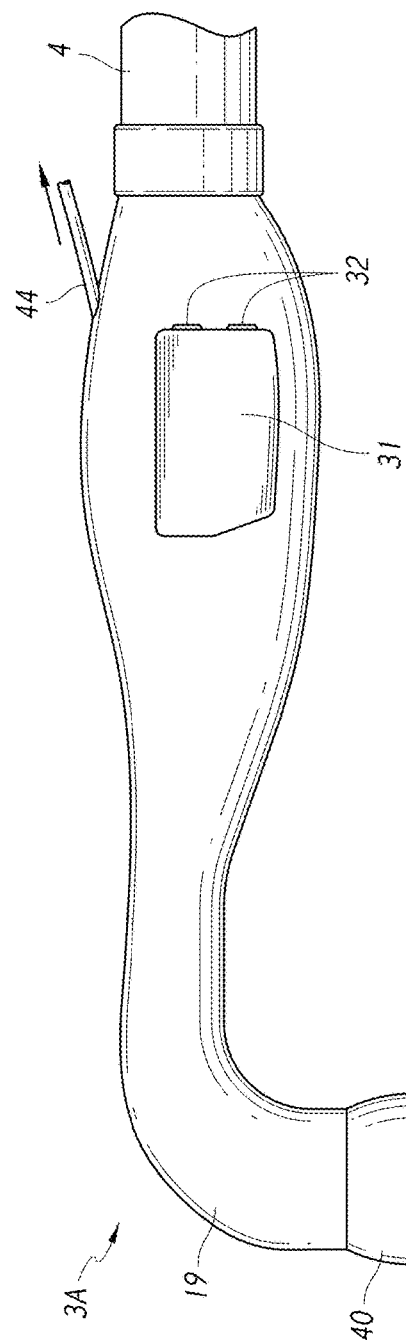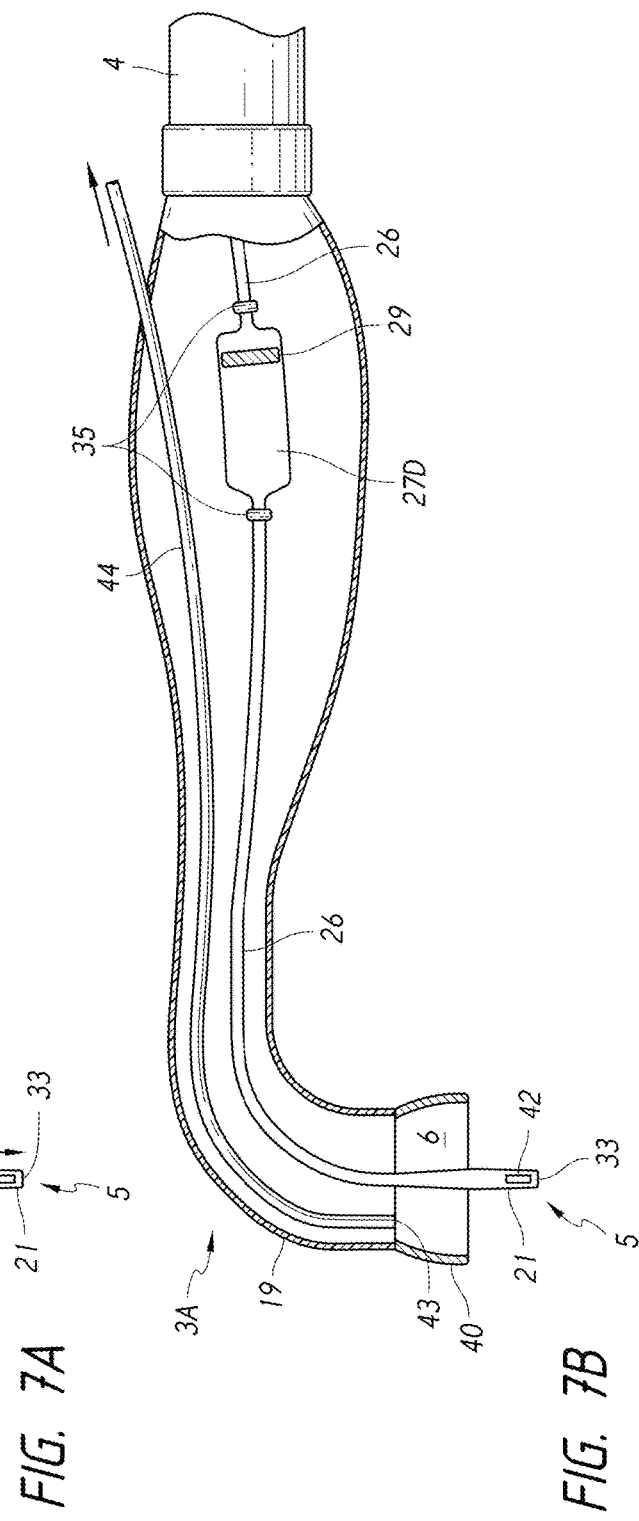
FIG. 7A
FIG. 7B

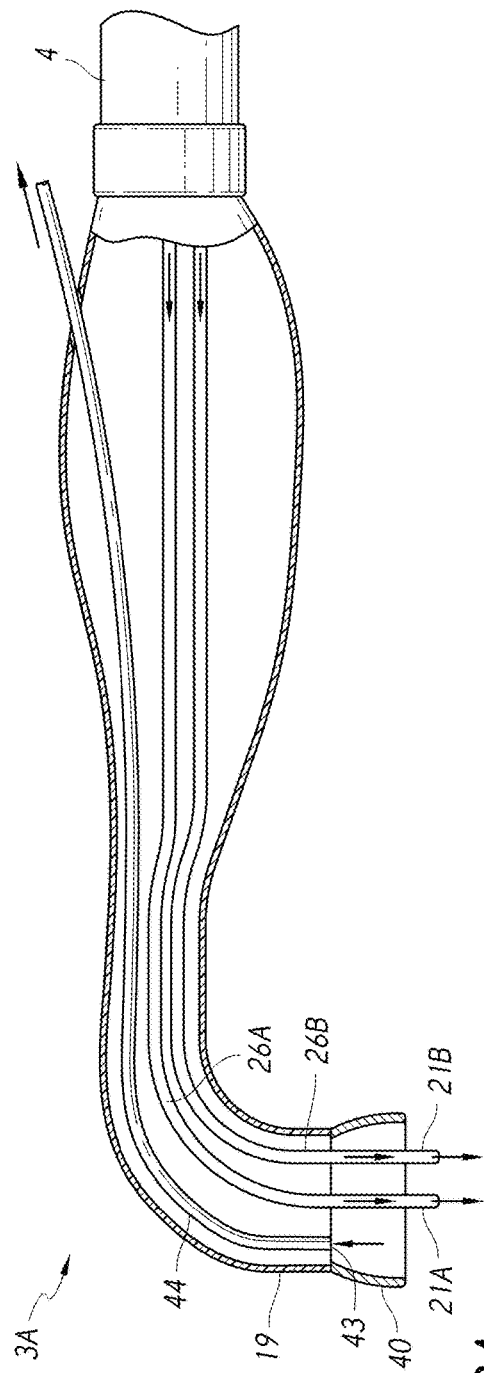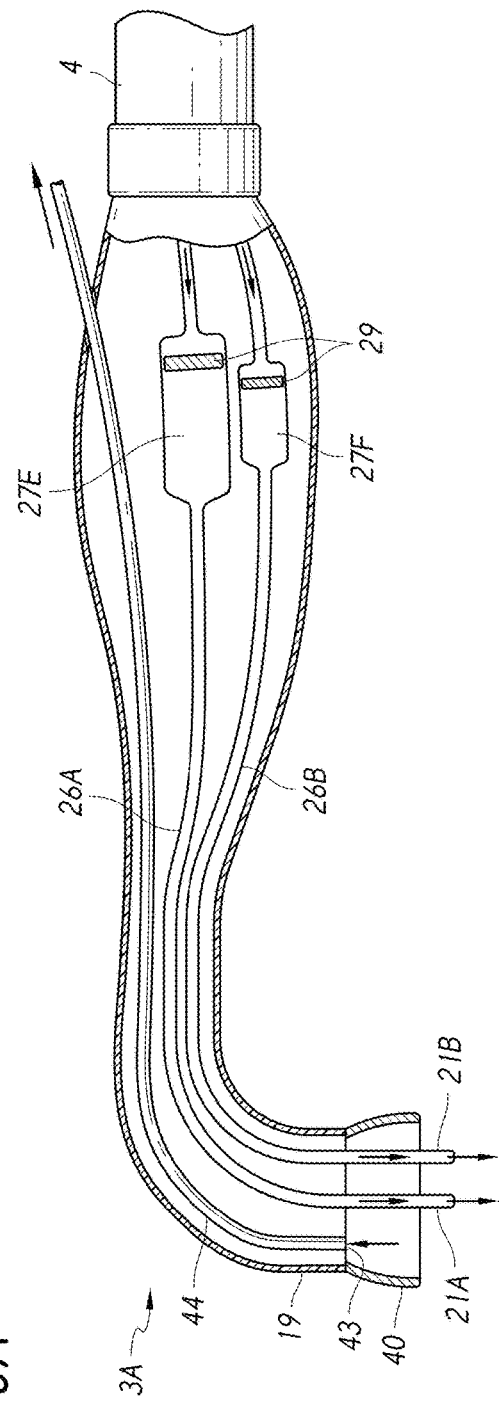
FIG. 8A
FIG. 8B

APPARATUS AND METHODS FOR FILLING TEETH AND ROOT CANALS

CROSS-REFERENCE TO RELATED APPLICATIONS

This application claims the benefit of U.S. Provisional Patent Application No. 61/839,855, filed Jun. 26, 2013, entitled "APPARATUS AND METHODS FOR FILLING TEETH AND ROOT CANALS;" U.S. Provisional Patent Application No. 61/866,420, filed Aug. 15, 2013, entitled "APPARATUS AND METHODS FOR FILLING TEETH AND ROOT CANALS;" U.S. Provisional Patent Application No. 61/873,789, filed Sep. 4, 2013, entitled "APPARATUS AND METHODS FOR FILLING TEETH AND ROOT CANALS;" U.S. Provisional Patent Application No. 61/976,699, filed Apr. 8, 2014, entitled "APPARATUS AND METHODS FOR FILLING TEETH AND ROOT CANALS;" and U.S. Provisional Patent Application No. 61/982,223, filed Apr. 21, 2014, entitled "APPARATUS AND METHODS FOR FILLING TEETH AND ROOT CANALS," each of which is hereby incorporated by reference herein in its entirety and for all purposes.

BACKGROUND OF THE INVENTION

1. Field of the Invention

The present disclosure relates generally to dentistry and endodontics, and to apparatus, methods, and compositions for filling teeth and root canals.

2. Description of the Related Art

In conventional dental and endodontic procedures, mechanical instruments such as drills, files, brushes, etc. are used to clean unhealthy material from a tooth. For example, dentists often use drills to mechanically break up carious regions (e.g., cavities) in a surface of the tooth. Such procedures are often painful for the patient and frequently do not remove all the diseased material. Furthermore, in conventional root canal treatments, an opening is drilled through the crown or side of a diseased tooth, and endodontic files are inserted into the root canal system to open the canal spaces and remove organic material therein. The root canal is then filled with an obturation material such as gutta percha or a flowable material, and the tooth is restored. However, it can be challenging to ensure that the filling material fully obturates the treatment region of the tooth. Accordingly, there is a continuing need for improved dental and endodontic treatments.

SUMMARY

Various non-limiting aspects of the present disclosure will now be provided to illustrate features of the disclosed apparatus, methods, and compositions. Examples of apparatus, methods, and compositions for endodontic treatments are provided.

In one embodiment, a dental apparatus is disclosed. The dental apparatus can comprise a pressure wave generator to be disposed at a treatment region of a tooth. The pressure wave generator can include an opening to deliver a flowable filling material to the treatment region. The apparatus can include a reservoir for supplying the filling material to the pressure wave generator. The pressure wave generator can be configured to generate pressure waves through the treatment region to cause the filling material to substantially fill the treatment region.

In another embodiment, a method of filling a treatment region of a tooth is disclosed. The method can comprise supplying a flowable filling material to the treatment region. The method can include generating pressure waves through the filling material to cause the filling material to substantially fill the treatment region.

In yet another embodiment, a dental apparatus is disclosed. The apparatus can include a handpiece having a distal portion to be positioned at a treatment region of a tooth and a fluid supply line extending proximally from the distal portion. The distal portion can comprise an opening for supplying fluid to the treatment region from the fluid supply line. The apparatus can be configured to operate in a cleaning mode in which cleaning fluid passes through the opening to clean the treatment region. The apparatus can be configured to operate in a filling mode in which a flowable filling material passes through the opening to fill the treatment region.

In another embodiment, a dental apparatus is disclosed. The dental apparatus can include a handpiece having a distal portion to be positioned at a treatment region of a tooth. The handpiece can further comprise a first fluid supply line and a second fluid supply line to deliver fluid to the treatment region. The apparatus can be configured to deliver a first composition through the first fluid supply line and a second composition through the second fluid supply line to the treatment region. The apparatus can be further configured to combine the first composition with the second composition at a location in the handpiece or at the treatment region of the tooth to form a filling material to substantially fill the treatment region.

In another embodiment, a method of obturating a treatment region of a tooth is disclosed. The method can include supplying a first composition to a handpiece. The method can include supplying a second composition to the handpiece. The method can comprise forming a filling material by combining the first composition with the second composition at a location in the handpiece or at the treatment region of the tooth. The method can comprise causing the filling material to flow throughout substantially the entire treatment region.

In another embodiment, a method of filling a treatment region of a tooth is disclosed. The method can comprise supplying a flowable filling material to the treatment region. The method can further include activating a pressure wave generator to cause the flowable filling material to harden or to enhance the hardening of the flowable filling material.

In another embodiment, a dental apparatus is disclosed. The dental apparatus can include a handpiece and a fluid supply line. The dental apparatus can include a supply device for supplying a filling material to the handpiece through the fluid supply line. The supply device can comprise a coiled portion of the fluid supply line.

For purposes of this summary, certain aspects, advantages, and novel features of certain disclosed inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein. Further, the foregoing is intended to summarize certain disclosed inventions and is not intended to limit the scope of the inventions disclosed herein.

BRIEF DESCRIPTION OF THE DRAWINGS

The foregoing and other features, aspects, and advantages of the embodiments of the apparatus and methods of cleaning teeth are described in detail below with reference to the drawings of various embodiments, which are intended to illustrate and not to limit the embodiments of the invention. The drawings comprise the following figures in which:

FIG. 1D is a schematic diagram of the system of FIG. 1C, in which the system is configured to fill the cleaned treatment region, in accordance with the embodiments disclosed herein.

FIG. 4A is a schematic side view of a tooth coupler comprising a handpiece having a cleaning mode and an obturation or filling mode.

FIG. 4B is a schematic side cross-sectional view of the handpiece shown in FIG. 4A.

FIG. 5A is a schematic side view of a treatment handpiece configured to deliver a flowable obturation or filler material to a treatment region of a tooth.

FIG. 5B is a schematic side cross-sectional view of the handpiece shown in FIG. 5A.

FIG. 6C is a side cross-sectional view of a handpiece configured to couple to a console by way of an interface member and a cartridge configured to be disposed between the interface member and the console.

FIG. 6D is a schematic, cross-sectional magnified view of a cartridge disposed proximal a handpiece.

FIG. 7A is a schematic side view of a handpiece having a removable obturation reservoir.

FIG. 7B is a schematic side cross-sectional view of the handpiece shown in FIG. 7A.

FIG. 8A is a schematic side cross-sectional view of a handpiece configured to deliver a first composition and a second composition to a treatment region of a tooth to obturate or fill the treatment region, according to one embodiment.

FIG. 8B is a schematic side cross-sectional view of a handpiece configured to deliver a first composition and a second composition to fill a treatment region of a tooth, according to another embodiment.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

I. Overview of System and Methods

A. Overview of Various System Components

Figure 1A:
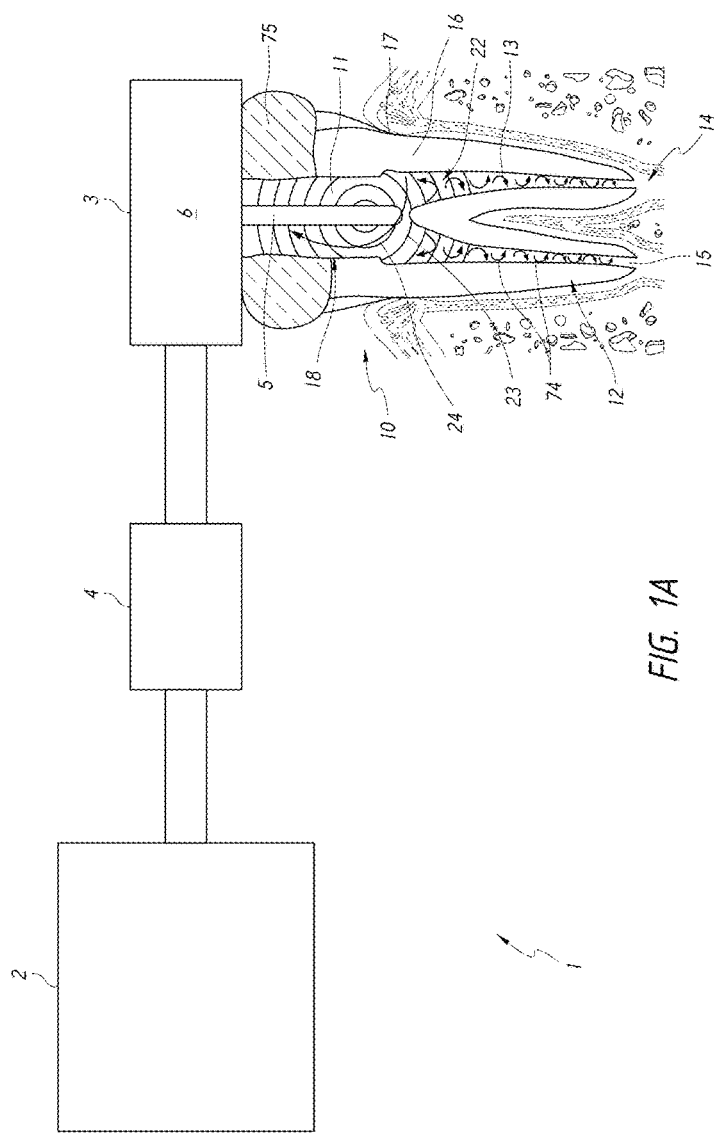
FIG. 1A is a schematic diagram of a system for cleaning a root canal of a tooth, in accordance with the embodiments disclosed herein.

FIG. 1A is a schematic diagram of a system 1, in accordance with the embodiments disclosed herein. The system 1 shown in FIG. 1A may be configured to perform various types of treatment procedures, including, e.g., cleaning treatments, obturation treatments, restoration treatments, etc. In the embodiment shown in FIG. 1A, the system 1 is illustrated as being coupled to (e.g., positioned against in some arrangements) a tooth 10 that is a molar tooth of a mammal, such as a human. However, the tooth 10 may be any other suitable type of tooth, such as a pre-molar, bicuspid, incisor, canine, etc. Furthermore, the system 1 shown in FIG. 1A can include components configured to remove unhealthy or undesirable materials from a tooth or surrounding gum tissue, for example, a root canal 13 of the tooth 10. Thus, in the embodiment of FIG. 1A, the system 10 is configured to clean the tooth 10.

The tooth 10 includes hard structural and protective layers, including a hard layer of dentin 16 and a very hard outer layer of enamel 17. A pulp cavity 11 is defined within the dentin 16. The pulp cavity 11 comprises one or more root canals 13 extending toward an apex 14 of each root 12. The pulp cavity 11 and root canal 13 contain dental pulp, which is a soft, vascular tissue comprising nerves, blood vessels, connective tissue, odontoblasts, and other tissue and cellular components. Blood vessels and nerves enter/exit the root canal 13 through a tiny opening, the apical foramen or apical opening 15, near a tip of the apex 14 of the root 12. It should be appreciated that, although the tooth 10 illustrated herein is a molar, the embodiments disclosed herein can advantageously be used to treat any suitable type of tooth, including pre-molars, canines, incisors, etc.

As illustrated in FIG. 1A, the system 1 can be used to remove unhealthy materials (such as organic and inorganic matter) from an interior of the tooth 10, e.g., from the root canal 13 of the tooth 10. For example, an endodontic access opening 18 can be formed in the tooth 10, e.g., on an occlusal surface, a buccal surface, or a lingual surface. The access opening 18 provides access to a portion of a pulp cavity 11 of the tooth 10. The system 1 can include a console 2, a pressure wave generator 5, and a tooth coupler 3 (such as a handpiece) adapted to couple to the tooth 10. The tooth coupler 3 can couple to the tooth 10 in any suitable way. In some arrangements, the tooth coupler 3 can be positioned against and/or attach to the tooth 10 by way of a tooth seal 75. For example, the clinician can hold the tooth coupler 3 against the tooth 10 during treatment. In some embodiments, the tooth coupler 3 can define a chamber 6 configured to retain fluid therein. In some embodiments, the pulp cavity 11 can define a tooth chamber configured to retain fluid therein. In some embodiments, the tooth coupler 3 may not define a chamber, and the tooth chamber defined at least in part by the pulp cavity 11 can retain fluid.

The tooth coupler 3 disclosed herein can be any suitable structure or housing configured to couple to the tooth 10 for a treatment procedure. As used herein, "couple" is meant to include arrangements in which there is a connection with the tooth 10, as well as arrangements in which the coupler 3 is placed against or in the tooth and is held by the clinician in that position. The pressure wave generator 5 can be coupled to and/or disposed in or on the tooth coupler 3 in various embodiments.

A system interface member 4 can electrically, mechanically, and/or fluidly connect the console 2 with the tooth coupler 3 and pressure wave generator 5. For example, in some embodiments, the system interface member 4 can removably couple the tooth coupler 3 to the console 2. In such embodiments, the clinician may use the tooth coupler 3 one time (or a few times), and may dispose the tooth coupler 3 after each procedure (or after a set number of procedures). The console 2 and interface member 4 may be reused multiple times to removably couple (e.g., to connect and/or disconnect) to multiple tooth couplers 3 using suitable engagement features, as discussed herein. The interface member 4 can include various electrical and/or fluidic pathways to provide electrical, electronic, and/or fluidic communication between the console 2 and the tooth coupler 3. The console 2 can include a control system and various fluid and/or electrical systems configured to operate the pressure wave generator 5 during a treatment procedure. The console 2 can also include a management module configured to manage data regarding the treatment procedure. The console 2 can include a communications module configured to communicate with external entities about the treatment procedures.

As shown in FIG. 1A, the system 1 can be used in cleaning procedures to clean substantially the entire root canal system. In other procedures, such as obturation procedures (see FIG. 1B), the system 1 can be used to fill substantially the entire root canal system with an obturation or filler material. In still other procedures, the system 1 can be used to restore a tooth 10. For example, in cleaning procedures, the chamber 6 of the tooth coupler 3 and/or the pulp cavity 11 of the tooth 10 can be at least partially (or substantially) filled with a fluid 22. In various embodiments disclosed herein, the pressure wave generator 5 can generate pressure waves 23 that propagate through the fluid 22. The generated pressure waves 23 may be of sufficient power and relatively low frequencies to produce fluid motion 24 in the pulp cavity 11 of the tooth 10, the root canal 13, and/or in the chamber 6 of the tooth coupler 3. The pressure wave generator 5 can also generate pressure waves of sufficient power and relatively higher frequencies to produce surface effect cavitation and/or microscale fluid motion created by the impact of the waves on a surface, either inside or outside the tooth 10. That is, for example, the pressure wave generators 5 disclosed herein can clean the tooth by generating large-scale or bulk fluid motion 24 in or near the tooth 10, and by generating smaller-scale fluid motion at higher frequencies. In some arrangements, the fluid motion 24 in the chamber 6 can generate induced fluid motion such as vortices 74, swirl, etc. in the tooth 10 and root canal 13 that can clean the canal 13. For example, in some embodiments, a high velocity stream of liquid can pass over an orifice (such as the canals), which can create a high speed stream of liquid transverse to the canals. The transverse stream may induce vortices 74 that traverse down the canals 13. Thus, the high-pressure stream can create a low pressure stream that cleans the root canals. In some arrangements, the pressure waves 23 can generate normal stress or shear stress or a combination of both onto the surfaces within the treatment region. Although the pressure wave generator 5 shown in FIG. 1A is shown as extending into the tooth, in other arrangements, the pressure wave generator 5 may be disposed outside the tooth, such as within the chamber 6. Additional systems and methods for cleaning teeth, e.g., using pressure wave generators that can include a liquid jet device, (including molars, pre-molars, etc.) may be found in U.S. Patent Publication US 2007/0248932, in U.S. Patent Publication 2011/0117517, in U.S. Patent Publication US 2012/0237893 and in U.S. patent application Ser. No. 14/137,937, filed Dec. 20, 2013, titled "APPARATUS AND METHODS FOR CLEANING TEETH AND ROOT CANALS," each of which is incorporated by reference herein in its entirety and for all purposes. Additionally, the console 2 can include a control system comprising a processor and non-transitory memory. Computer-implemented instructions can be stored on the memory and can be executed by the processor to assist in controlling cleaning and/or filling procedures. Additional details of the console 2 may be found in U.S. patent application Ser. No. 14/172,809, filed on Feb. 4, 2014, entitled "DENTAL TREATMENT SYSTEM," and in U.S. Patent Publication No. US 2012/0237893, each of which is incorporated by reference herein in its entirety and for all purposes.

Figure 1B:
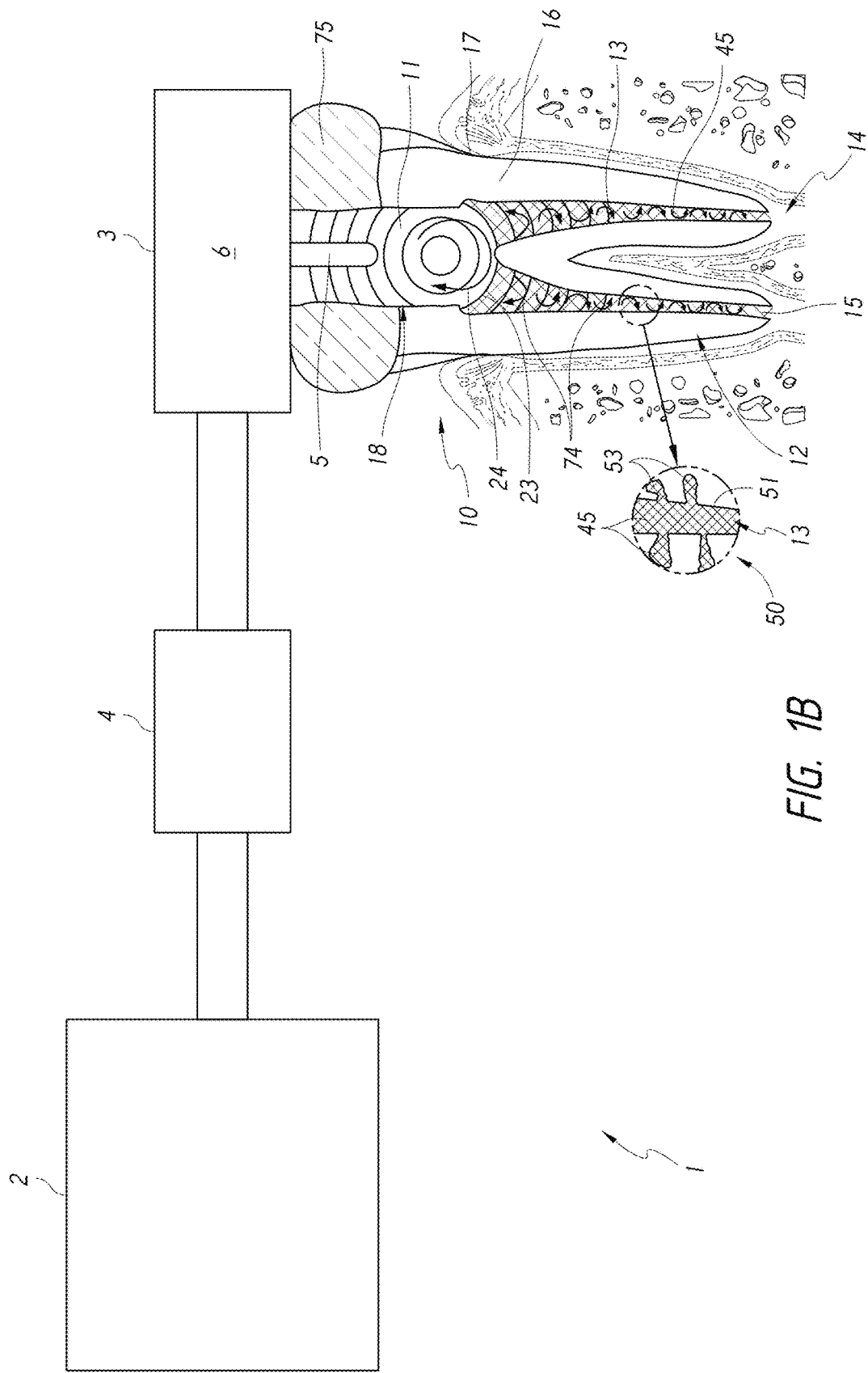
FIG. 1B is a schematic diagram of the system of FIG. 1A, in which the system is configured to obturate the root canal, in accordance with the embodiments disclosed herein.

FIG. 1B is a schematic diagram of the system 1, in which the system is configured to obturate or fill the root canals 13 of the tooth 10. As with the embodiment of FIG. 1A, the system can include a pressure wave generator 5, a tooth coupler 3, an interface member 4, and a console 2. In FIG. 1B, the system 1 is used to fill or obturate the root canal 13 with an obturation material 45. For example, the clinician can clean the root canal 13 in any suitable way, such as by using drills or files, or by using a pressure wave generator (which may be the same as or different from the pressure wave generator 5 shown in FIG. 1B). When the root canal 13 is cleaned, the clinician can supply an obturation material 45 in its flowable state to the pulp cavity 11, canals 13, or other internal chambers of the tooth 10.

As explained herein, the clinician can supply the obturation material 45 to the treatment region (e.g., the root canal) in any suitable manner. For example, in some embodiments, the pressure wave generator 5 (which may be coupled to or formed with a handpiece) may have one or more openings (see, e.g., FIGS. 4A-4B, et seq.) configured to deliver the flowable obturation material 45 to the tooth 10. In other embodiments, the clinician can supply the obturation material 45 to the tooth by manually placing it in the tooth 10, e.g., by hand, by syringe, or by a mechanical tool. In still other embodiments, a dental handpiece can include one or more supply lines that are configured to route the flowable obturation material 45 to the tooth 10. The obturation material 45 can be any suitable obturation material disclosed herein. In particular, the obturation material 45 can have a flowable state in which the obturation material 45 flows through the treatment region to fill the root canals 13 and/or pulp cavity 11. The obturation material 45 can have a hardened state in which the obturation material 45 solidifies after filling the treatment region.

Advantageously, the pressure wave generator 5 can be activated to enhance the obturation procedure. For example, the pressure wave generator 5 can be activated to assist in flowing the obturation material 45 throughout the treatment region to be filled. The pressure wave generator 45 can thereby assist in substantially filling the tooth 10. As shown in inset 50 of FIG. 1B, for example, when activated, the pressure wave generator 5 can cause the obturation material 45 to flow into major canal spaces 51 of the tooth 10, as well as into small spaces 53 of the tooth 10. Thus, the system 1 shown in FIG. 1B can assist in filling even small cracks, tubules, and other tiny spaces (e.g., the small spaces 53) of the tooth 10. By filling the small spaces 53 of the tooth, the system 1 can ensure a more robust obturation procedure which results in long-term health benefits for the patient. As explained herein, the pressure waves 23 and/or fluid motion 24 (which may include vortices 74) generated by the pressure wave generator 5 may interact with the obturation material 45 to assist in filling the small spaces 53 and the major spaces 51 of the tooth 10. Furthermore, in some embodiments, the pressure wave generator 5 can be activated to assist in curing or hardening the obturation material 45. For example, as explained herein, some types of obturation materials may cure or harden (or the curing or hardening may be enhanced) when agitated by pressure waves 23 generated by the pressure wave generator 5. In addition, in various embodiments, the obturation or filling material can be degassed, which can help deliver the obturation material to small spaces of the tooth. Accordingly, the pressure wave generator 5 can enhance the obturation procedure in a variety of ways.

In some embodiments, the obturation material 45 is supplied to the tooth 10, and the pressure wave generator 5 is subsequently activated to enhance the obturation procedure (e.g., to improve the filling process and/or to enhance or activate the curing process). For example, in such embodiments, the clinician can supply the obturation material 45 to the tooth 10 using a syringe or other device, and the pressure wave generator 5 can subsequently (or concurrently) be activated to fill the treatment region. In other embodiments, the pressure wave generator 5 can supply the obturation material 45 and generate pressure waves through the obturation material (or other fluids at the treatment region). In some embodiments, supplying the obturation material and generating pressure waves can occur substantially simultaneously, or can overlap by some amount over time. For example, the pressure wave generator 5 can be activated to supply the obturation material 45 to the treatment region. For example, in embodiments in which the pressure wave generator 5 comprises a liquid jet, a jet of obturation material 45 can interact with fluids in the tooth 10 (e.g., other portions of the obturation material or other treatment fluid) to generate pressure waves that propagates through the fluids. The resulting pressure waves can enhance the obturation procedure. In other embodiments, different types of fluids (e.g., water or other treatment fluids) may form the jet, and the jet can pass through obturation materials in the treatment region. Interaction of the fluid jet and the obturation material can enhance the obturation procedure.

As disclosed herein, the pressure wave generator 5 can comprise any suitable type of pressure wave generator, e.g., a liquid jet device, a laser, a mechanical stirrer, an ultrasonic transducer, etc. The pressure wave generator 5 can be sized such that the pressure wave generator 5 is disposed outside the region of the tooth 10 that is to be obturated. For example, the pressure wave generator 5 can be disposed in the chamber 6 such that it is disposed outside the tooth 10. In other arrangements, the pressure wave generator 5 can extend partially into the tooth 10. In some arrangements, the pressure wave generator 5 can extend to a depth that does not interfere with the filling. As explained herein, the system 1 can include a cleaning mode for cleaning the treatment region and a filling mode to fill or obturate the treatment region. The console 2 can include a control system comprising a processor and memory. The control system can be programmed or configured to switch the system 1 from the cleaning mode to the filling mode and vice versa. The control system of the console 2 can also control the operation of cleaning and/or filling procedures.

Figure 1C:
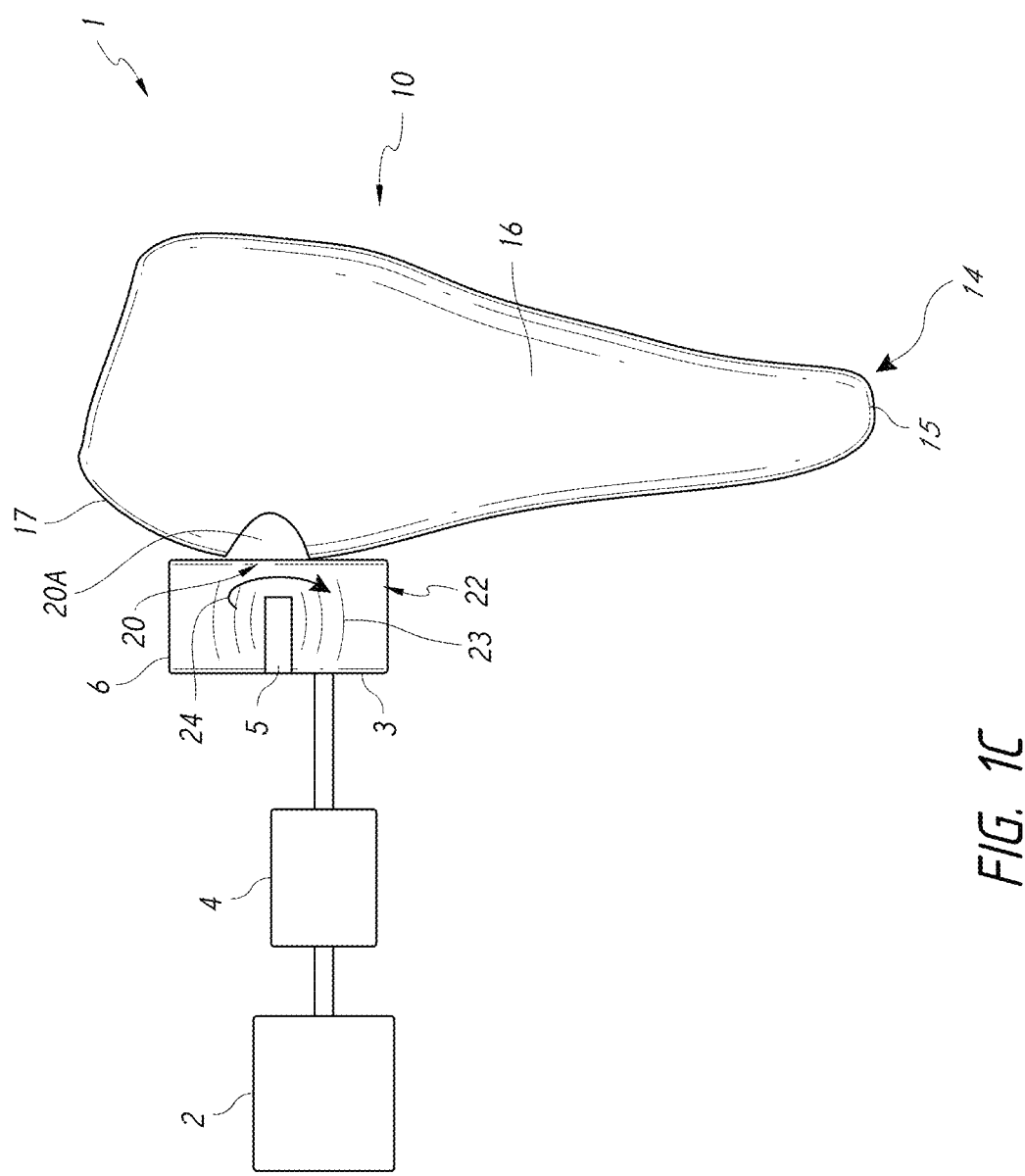
FIG. 1C is a schematic diagram of a system that includes components configured to clean unhealthy or undesirable material from a treatment region on an exterior surface of the tooth.

FIG. 1C is a schematic diagram of a system 1 that includes components configured to clean unhealthy or undesirable material from a treatment region 20 on an exterior surface of the tooth 10. For example, as in FIG. 1A, the system 1 can include a tooth coupler 3 and a pressure wave generator 5. The tooth coupler 3 can communicate with a console 2 by way a system interface member 4. Unlike the system 1 of FIG. 1A, however, the tooth coupler 3 is coupled to (e.g., positioned against by a clinician) a treatment region 20 on an exterior surface of the tooth 10. In some embodiments, the tooth coupler 3 can be stably positioned against the treatment region and can be sealed to the tooth 10, e.g., by way of an adhesive or other seal. The system 1 of FIG. 1C can be activated to clean an exterior surface of the tooth 10, e.g., a carious region of the tooth 10 and/or remove undesirable dental deposits, such as plaque, calculus biofilms, bacteria, etc, from the tooth 10 and/or surround gum tissue. In other embodiments (see FIG. 1D), the system 1 can be activated to fill a treated region on the exterior surface of the tooth 10 with a filling or restoration material. As with the embodiment of FIG. 1A, pressure waves 23 and/or fluid motion 24 can be generated in the tooth coupler 3 and chamber 6, which can act to clean the treatment region 20 of the tooth 10, forming a cleaned treatment region 20A in which the carious (or other unhealthy material) is removed. Additional details of systems and methods for treating carious regions of teeth may be found in International Application Publication WO 2013/142385 (PCT/US2013/032635), having an international filing date of Mar. 15, 2013, entitled "APPARATUS AND METHODS FOR CLEANING TEETH," which is incorporated by reference herein in its entirety and for all purposes. Additional details of systems and methods for removing undesirable dental deposits (such as plaque, calculus, etc.) from teeth and/or gums may be found in International Application Publication WO 2013/155492 (Application No. PCT/US2013/036493), having an international filing date of Apr. 12, 2013, entitled "APPARATUS AND METHODS FOR CLEANING TEETH AND GINGIVAL POCKETS," and in U.S. Patent Publication No. US 2014/0099597, filed Apr. 11, 2013, entitled "APPARATUS AND METHODS FOR CLEANING TEETH AND GINGIVAL POCKETS," each of which is incorporated by reference herein in its entirety and for all purposes.

FIG. 1D is a schematic diagram of the system 1 of FIG. 1C, in which the system 1 is configured to fill the treated carious region 20A of the tooth 10. As with the embodiment of FIG. 1C, the system can include a pressure wave generator 5, a tooth coupler 3, an interface member 4, and a console 2. When the carious or other unhealthy material is removed from the tooth 10, the clinician can fill the cleaned treatment region 20A with a suitable filler or obturation material 45. As with the embodiment of FIG. 1B, the obturation material 45 can be supplied to the cleaned treatment region 20A. The pressure wave generator 5 can act to substantially fill the treatment region 20A and/or to enhance or activate the hardening of the filler obturation material 45. In some embodiments, the filler or obturation material 45 is supplied to the tooth 10, and the pressure wave generator 5 is subsequently activated to enhance the filling procedure (e.g., to improve the filling process and/or to enhance or activate the curing process). For example, in such embodiments, the clinician can supply the filler or obturation material 45 to the treatment region 20A using a syringe, and the pressure wave generator 5 can subsequently be activated to fill the treatment region. In other embodiments, the pressure wave generator 5 is activated to supply the filler or obturation material 45 to the treatment region 20A and to generate pressure waves through the material. For example, in embodiments in which the pressure wave generator 5 comprises a liquid jet, a jet of obturation or filler material 45 (or other type of fluid) can interact with fluids at the treatment region 20A (e.g., other portions of the filler or obturation material or other treatment fluid) to generate pressure waves that propagates through the fluids. The resulting pressure waves can enhance the obturation procedure.

B. Overview of Treatment Procedures

The system 1 disclosed herein can be used with various types of treatment procedures. For example, some embodiments disclosed herein can advantageously remove undesirable or unhealthy materials from a tooth such that substantially all the unhealthy material is removed while inducing minimal or no discomfort and/or pain in the patient. For example, when activated by the clinician, the pressure wave generator 5 can induce various fluidic effects that interact with the unhealthy material to be removed, even when the pressure wave generator 5 is disposed at a position remote from the treatment region of the tooth, e.g., the region of the tooth that includes the unhealthy or undesirable material to be removed. The pressure wave generator 5 can impart energy to a fluid 22 that induces the relatively large-scale or bulk circulation or movement 24 of liquid in the chamber 6 and/or tooth 10, and that also generates pressure waves 23 that propagate through the fluid 22 and tooth 10. The generated fluid motion 24 and pressure waves 23 can magnify or enhance the properties of the fluid 22 to enhance cleaning of the tooth 10. In some embodiments, the pressure wave generator 5 can be used to obturate or fill the root canals and/or other treated regions of the tooth, and can also be used to restore or build up a damaged or diseased tooth.

1. Enhancing the Cleaning of Teeth

The system 1 disclosed herein can be used to clean teeth. For example, the system 1 can be configured to clean organic and inorganic material, including diseased pulp, bacteria, etc., from root canals of the tooth 10. In some embodiments, the system 1 can be configured to remove carious regions of the tooth 10, e.g., regions of the tooth 10 that are decayed. The carious regions can be formed on an exterior surface of the tooth 10 in some arrangements. Moreover, the system 1 can be configured to clean undesirable dental deposits from exterior surfaces of the tooth 10, including plaque, calculus, biofilms, bacteria, and other unhealthy deposits. In some arrangements, the system 1 can utilize, alone or in combination, the chemistry of various treatment fluids, pressure waves generated by the pressure wave generator 5, and fluid motion 24 created in the chamber 6 of the tooth coupler 3 and/or in a chamber within the tooth 10.

a. Chemistry of Various Treatment Fluids

In cleaning procedures, the fluid 22 supplied to the chamber 6 and/or to the pulp cavity 11 of the tooth 10 can comprise a treatment fluid that can be introduced into the tooth 10 and the chamber 6 to assist in removing unhealthy or undesirable materials from the tooth 10. The treatment fluids can be selected based on the chemical properties of the fluids when reacting with the undesirable or unhealthy material to be removed from the tooth 10. The treatment fluids disclosed herein can include any suitable fluid, including, e.g., water, saline, etc. Various chemicals can be added to treatment fluid for various purposes, including, e.g., tissue dissolving agents (e.g., NaOCl or bleach), disinfectants (e.g., chlorhexidine), anesthesia, fluoride therapy agents, ethylenediaminetetraacetic acid (EDTA), citric acid, and any other suitable chemicals. For example, any other antibacterial, decalcifying, disinfecting, mineralizing, or whitening solutions may be used as well. The clinician can supply the various fluids to the tooth in one or more treatment cycles, and can supply different fluids sequentially or simultaneously.

During some treatment cycles, bleach-based solutions (e.g., solutions including NaOCl) can be used to dissociate diseased tissue (e.g., diseased organic matter in the root canal 13) and/or to remove bacteria, biofilm or endotoxins (Lipopolysaccharide or LPS) from the tooth 10. One example of a treatment solution comprises water or saline with 0.3% to 6% bleach (NaOCl). In some methods, tissue dissolution and dental deposit removal in the presence of bleach may not occur when the bleach concentration is less than 1%. In some treatment methods disclosed herein, tissue dissolution and dental deposit removal can occur at smaller (or much smaller) concentrations.

During other treatment cycles, the clinician can supply an EDTA-based solution to remove undesirable or unhealthy calcified material from the tooth 10. For example, if a portion of the tooth 10 and/or root canal 13 is shaped or otherwise instrumented during the procedure, a smear layer may form on the walls of the canal 13. The smear layer can include a semi-crystalline layer of debris, which may include remnants of pulp, bacteria, dentin, and other materials. Treatment fluids that include EDTA may be used to remove part or all of the smear layer, and/or calcified deposits on the tooth 10. EDTA may also be used to remove dentin packed into isthmuses and lateral canals during the instrumentation process. EDTA may also be used to remove a microscopic layer off enamel and cleaning and staining purposes. Other chemicals such as citric acid may also be used for similar purposes.

During yet other cycles, for example, the clinician may supply a treatment fluid that comprises substantially water. The water can be used to assist in irrigating the tooth before, during, and/or after the treatment. For example, the water can be supplied to remove remnants of other treatment fluids (e.g., bleach or EDTA) between treatment cycles. Because bleach has a pH that tends to be a base and because EDTA is an acid, it can be important to purge the tooth 10 and chamber 6 between bleach and EDTA treatments to avoid potentially damaging chemical reactions. Furthermore, the water can be supplied with a sufficient momentum to help remove detached materials that are disrupted during the treatment. For example, the water can be used to convey waste material from the tooth 10.

Various solutions may be used in combination at the same time or sequentially at suitable concentrations. In some embodiments, chemicals and the concentrations of the chemicals can be varied throughout the procedure by the clinician and/or by the system to improve patient outcomes. For example, during an example treatment procedure, the clinician can alternate between the use of water, bleach, and EDTA, in order to achieve the advantages associated with each of these chemicals. In one example, the clinician may begin with a water cycle to clean out any initial debris, then proceed with a bleach cycle to dissociate diseased tissue and bacteria from the tooth. A water cycle may then be used to remove the bleach and any remaining detached materials from the tooth 10. The clinician may then supply EDTA to the tooth to remove calcified deposits and/or portions of a smear layer from the tooth 10. Water can then be supplied to remove the EDTA and any remaining detached material from the tooth 10 before a subsequent bleach cycle. The clinician can continually shift between cycles of treatment fluid throughout the procedure. The above example is for illustrative purposes only. It should be appreciated that the order of the cycling of treatment liquids may vary in any suitable manner and order.

Thus, the treatment fluids used in the embodiments disclosed herein can react chemically with the undesirable or unhealthy materials to dissociate the unhealthy materials from the healthy portions of the tooth 10. The treatment fluids can also be used to irrigate waste fluid and/or detached or delaminated materials out of the tooth 10. In some embodiments, as explained in more detail herein, the treatment solution (including any suitable composition) can be degassed, which may improve cavitation and/or reduce the presence of gas bubbles in some treatments. In some embodiments, the dissolved gas content can be less than about 1% by volume.

b. Enhancement of Cleaning and Filling Using Pressure Waves and Examples of Pressure Wave Generators A pressure wave generator 5 can remove unhealthy materials from a tooth by propagating pressure waves 23 through a propagation medium such as the fluid 22 (e.g., the treatment fluid) to the treatment region, which can include one or more teeth and/or gums. Without being limited by theory, a few potential ways that the pressure waves 23 remove undesirable materials are presented herein. In addition, the pressure wave generators disclosed herein may also be used to effectively obturate or fill treatment regions of the tooth. Note that these principles, and the principles described above, may be generally applicable for each embodiment disclosed herein.

In some arrangements, cavitation may be induced by the generated pressure waves 23. Upon irradiation of a liquid (e.g., water or other treatment fluid) with high intensity pressure or pressure waves 23, acoustic cavitation may occur. The oscillation or the implosive collapse of small cavitation bubbles can produce localized effects, which may further enhance the cleaning process, e.g., by creating intense, small-scale localized heat, shock waves, and/or microjets and shear flows. Therefore, in some treatment methods, acoustic cavitation may be responsible for or involved in enhancing the chemical reactions, sonochemistry, sonoporation, soft tissue/cell/bacteria dissociation, delamination and breakup of biofilms.

For example, if the treatment liquid contains chemical(s) that act on a particular target material (e.g., diseased organic or inorganic matter, stains, caries, dental calculus, plaque, bacteria, biofilms, etc.), the pressure waves 23 (acoustic field) and/or the subsequent acoustic cavitation may enhance the chemical reaction via convection, turbulence, agitation and/or sonochemistry. Indeed, the pressure waves 23 can enhance the chemical effects that each composition has on the unhealthy material to be removed from the tooth. For example, with a bleach-based treatment fluid, the generated pressure waves 23 can propagate so as to dissociate tissue throughout the entire tooth 10, including in the dentinal tubules and throughout tiny cracks and crevices of the tooth 10. As another example, with an EDTA-based treatment fluid, the generated pressure waves 23 can propagate so as to remove the smear layer and/or calcified deposits from the tooth 10, including in the tubules and/or in tiny cracks and crevices formed in the tooth 10. With a water-based treatment fluid, the generated pressure waves 23 can propagate so as to flush and/or irrigate undesirable materials from the tooth, including in tubules and tiny cracks and crevices. Accordingly, the generated pressure waves 23 can enhance the removal of undesirable or unhealthy materials from the tooth 10 by magnifying the chemical effects of whatever treatment fluid composition is used during a particular treatment cycle.

Furthermore, sonoporation, which is the process of using pressure waves and/or the subsequent acoustic cavitation to modify the permeability of the bacterial cell plasma membrane, may also expedite the chemical reaction that removes the microorganisms from the tooth. It should also be appreciated that generated pressure waves, and/or the subsequent acoustic cavitation of certain frequencies, may result in cellular and bacterial rupture and death (e.g., lysis) as well as removal of decayed and weakened dentin and enamel. The cellular and bacterial rupture phenomenon may kill bacteria which might otherwise reinfect the gingival pockets and/or the oral cavity.

Generated pressure waves and/or the subsequent acoustic cavitation may also loosen the bond of the structure of the unhealthy material (e.g., diseased tissue, calculus, biofilm, caries, etc.), and/or the pressure waves may dissociate the unhealthy material from the tooth 10. In some cases, pressure waves and/or acoustic cavitation may loosen the bond between the cells and the dentin and/or delaminate the tissue from the tooth. Furthermore, the pressure waves and/or the subsequent acoustic cavitation may act on decayed hard tissue (which may be relatively weak and loosely connected) through vibrations and/or shock waves, and/or the microjets created as a result of cavitation bubble implosion, to remove decayed hard tissue from other healthy portions of the tooth.

A pressure wave generator 5 can be used in various disclosed embodiments to clean a tooth 10, e.g., from interior or exterior portions of the tooth 10 and/or gums. In other embodiments, the pressure wave generator 5 can be used to fill or obturate a cleaned root canal or other treatment region of the tooth 10. In some embodiments, the pressure wave generator 5 can comprise an elongated member having an active distal end portion. The active distal end portion can be activated by a user to apply energy to the treatment tooth 10 to remove unhealthy or undesirable material from the tooth 10.

As explained herein, the disclosed pressure wave generators 5 can be configured to generate pressure waves 23 and fluid motion 24 with energy sufficient to clean undesirable material from a tooth 10. The pressure wave generator 5 can be a device that converts one form of energy into acoustic waves and bulk fluid motion (e.g., rotational motion) within the fluid 22. The pressure wave generator 5 can induce, among other phenomena, both pressure waves and bulk fluid dynamic motion in the fluid 22 (e.g., in the chamber 6), fluid circulation, turbulence, vortices and other conditions that can enable the cleaning of the tooth. The pressure wave generator 5 disclosed in each of the figures described herein may be any suitable type of pressure wave generator.

The pressure wave generator 5 can be used to clean the tooth 10 by creating pressure waves that propagate through the fluid 22, e.g., through treatment fluid at least partially retained in the chamber 6. In some implementations, the pressure wave generator 5 may also create cavitation, acoustic streaming, turbulence, etc. The pressure wave generator 5 (e.g., high-speed liquid jet, ultrasonic transducer, a laser fiber, etc.) can be placed at the desired treatment location in or on the tooth 10. The pressure wave generator 5 can create pressure waves 23 and fluid motion 24 within the fluid 22 inside a substantially-enclosed chamber 6 and/or in a tooth chamber of the tooth (e.g., the pulp cavity 11 and/or the root canal 13). In general, the pressure wave generator 5 can be sufficiently strong to remove unhealthy materials such as organic and/or inorganic tissue from teeth 10. In some embodiments, the pressure wave generator 5 can be configured to avoid substantially breaking down or harming natural dentin and/or enamel.

i. Liquid Jet Apparatus

For example, in some embodiments, the pressure wave generator 5 can comprise a liquid jet device. The liquid jet can be created by passing high pressure liquid through an orifice. The liquid jet can create pressure waves within the treatment liquid. In some embodiments, the pressure wave generator 5 comprises a coherent, collimated jet of liquid. The jet of liquid can interact with liquid in a substantially-enclosed volume (e.g., the chamber 6, the tooth chamber (e.g., pulp cavity 11 and/or root canals 13), and/or the mouth of the user) and/or an impingement member to create the acoustic waves. In addition, the interaction of the jet and the treatment fluid, as well as the interaction of the spray which results from hitting the impingement member and the treatment fluid, may assist in creating cavitation and/or other acoustic and fluid motion effects to clean the tooth. The liquid jet apparatus can be configured to clean and/or fill or obturate a treatment region of the tooth.

In various embodiments, the liquid jet device can comprise a positioning member (e.g., a guide tube) having a channel or lumen along which or through which a liquid jet can propagate. The distal end portion of the positioning member can include one or more openings that permit the deflected liquid to exit the positioning member and interact with the surrounding environment in the chamber 6 and/or tooth 10. In some treatment methods, the openings disposed at or near the distal end portion of the positioning member can be submerged in liquid that can be at least partially enclosed in the tooth coupler 3 attached to or enclosing a portion of the tooth 10. In some embodiments, the liquid jet can pass through the guide tube and can impact an impingement surface. The passage of the jet through the surrounding treatment fluid and impact of the jet on the impingement surface can generate the acoustic waves in some implementations. The flow of the submerged portion of the liquid jet may generate a cavitation cloud within the treatment fluid. The creation and collapse of the cavitation cloud may, in some cases, generate a substantial hydroacoustic field in or near the tooth. Further cavitation effects may be possible, including growth, oscillation, and collapse of cavitation bubbles. In addition, as explained above, bulk fluid motion, such as rotational flow, may be induced. The induced rotational flow can enhance the cleaning process by removing detached material and replenishing reactants for the cleaning reactions. These (and/or other) effects may lead to efficient cleaning of the tooth. The rotational flow may also create sufficient shear stress onto surface which then leads to dissociation, detachment, and delamination of unhealthy materials. In some embodiments, the rotational flow may include turbulent regions working on small scale regions or small scale unhealthy materials.

Additional details of a pressure wave generator and/or pressure wave generator that includes a liquid jet device may be found at least in ¶¶[0045]-[0050], [0054]-[0077] and various other portions of U.S. Patent Publication No. US 2011/0117517, published May 19, 2011, and in ¶¶[0136]-[0142] and various other portions of U.S. Patent Publication No. US 2012/0237893, published Sep. 20, 2012, each of which is incorporated by reference herein in its entirety and for all purposes.

As has been described, a pressure wave generator can be any physical device or phenomenon that converts one form of energy into acoustic waves within the treatment fluid and that induces normal and shear stresses as well as small scale flows near a treatment region in the chamber 6 and/or tooth 10. The pressure wave generator 5 may also convert the energy into rotational fluid motion of various length scales in the chamber 6 and/or tooth 10. Many different types of pressure wave generators (or combinations of pressure wave generators) are usable with embodiments of the systems and methods disclosed herein.

ii. Mechanical Energy

Mechanical energy pressure wave generators can also include rotating objects, e.g. miniature propellers, eccentrically-confined rotating cylinders, a perforated rotating disk, etc. These types of pressure wave generators can also include vibrating, oscillating, or pulsating objects such as sonication devices that create pressure waves via piezoelectricity, magnetostriction, etc. In some pressure wave generators, electric energy transferred to a piezoelectric transducer can produce acoustic waves in the treatment fluid. In some cases, the piezoelectric transducer can be used to create acoustic waves having a broad band of frequencies. Mechanical pressure wave generators can be configured to clean and/or fill or obturate a treatment region of the tooth.

iii. Electromagnetic Energy

Electromagnetic pressure wave generators can also be configured to clean and/or fill or obturate a treatment region of the tooth. An electromagnetic beam of radiation (e.g., a laser beam) can propagate energy into a chamber, and the electromagnetic beam energy can be transformed into acoustic waves as it enters the treatment fluid. In some embodiments, the laser beam can be directed into the chamber 6 and/or tooth coupler 3 as a collimated and coherent beam of light. The collimated laser beam can be sufficient to generate pressure waves as the laser beam delivers energy to the fluid. Furthermore, in various embodiments, the laser beam can be focused using one or more lenses or other focusing devices to concentrate the optical energy at a location in the treatment fluid. The concentrated energy can be transformed into pressure waves sufficient to clean the undesirable materials. In one embodiment, the wavelength of the laser beam or electromagnetic source can be selected to be highly absorbable by the treatment fluid in the chamber, tooth, and/or mouth (e.g., water) and/or by the additives in the treatment fluid (e.g., nanoparticles, etc.). The electromagnetic energy can be absorbed by at least one component and can turn the electromagnetic energy into either heat, vibration, or pressure waves, for example, through cavitation. For example, at least some of the electromagnetic energy may be absorbed by the fluid (e.g., water) in the chamber, which can generate localized heating and pressure waves that propagate in the fluid. The pressure waves generated by the electromagnetic beam can generate light-induced cavitation effects in the fluid. In some embodiments, the localized heating can induce rotational fluid flow in the chamber 6 and/or tooth 10 that further enhances cleaning of the tooth 10. The electromagnetic radiation from a radiation source (e.g., a laser) can be propagated to the chamber by an optical waveguide (e.g., an optical fiber), and dispersed into the fluid at a distal end of the waveguide (e.g., a shaped tip of the fiber, e.g., a conically-shaped tip). In other implementations, the radiation can be directed to the chamber by a beam scanning system.

The wavelength of the electromagnetic energy may be in a range that is strongly absorbed by water molecules. The wavelength may in a range from about 300 nm to about 3000 nm. In some embodiments, the wavelength is in a range from about 400 nm to about 700 nm, about 700 nm to about 1000 nm (e.g., 790 nm, 810 nm, 940 nm, or 980 nm), in a range from about 1 micron to about 3 microns (e.g., about 2.7 microns or 2.9 microns), or in a range from about 3 microns to about 30 microns (e.g., 9.4 microns or 10.6 microns). The electromagnetic energy can be in the ultraviolet, visible, near-infrared, mid-infrared, microwave, or longer wavelengths.

The electromagnetic energy can be pulsed or modulated (e.g., via a pulsed laser), for example with a repetition rate in a range from about 1 Hz to about 500 kHz. The pulse energy can be in a range from about 1 mJ to about 1000 mJ. The pulse width can be in a range from about 1 µs to about 500 µs, about 1 ms to about 500 ms, or some other range. In some cases, nanosecond pulsed lasers can be used with pulse rates in a range from about 100 ns to about 500 ns. The foregoing are non-limiting examples of radiation parameters, and other repetition rates, pulse widths, pulse energies, etc. can be used in other embodiments.

The laser can include one or more of a diode laser, a solid state laser, a fiber laser, an Er:YAG laser, an Er:YSGG laser, an Er,Cr:YAG laser, an Er,Cr:YSGG laser, a Ho:YAG laser, a Nd:YAG laser, a CTE:YAG laser, a $CO_2$ laser, or a Ti:Sapphire laser. In other embodiments, the source of electromagnetic radiation can include one or more light emitting diodes (LEDs). The electromagnetic radiation can be used to excite nanoparticles (e.g., light-absorbing gold nanorods or nanoshells) inside the treatment fluid, which may increase the efficiency of photo-induced cavitation in the fluid. The treatment fluid can include excitable functional groups (e.g., hydroxyl functional groups) that may be susceptible to excitation by the electromagnetic radiation and which may increase the efficiency of pressure wave generation (e.g., due to increased absorption of radiation). During some treatments, radiation having a first wavelength can be used (e.g., a wavelength strongly absorbed by the liquid, for instance water) followed by radiation having a second wavelength not equal to the first wavelength (e.g., a wavelength less strongly absorbed by water) but strongly absorbed by another element, e.g. dentin, dyes, or nanoparticles added to solution. For example, in some such treatments, the first wavelength may help create bubbles in the fluid, and the second wavelength may help disrupt the tissue.

The electromagnetic energy can be applied to the chamber 6 for a treatment time that can be in a range from about one to a few seconds up to about one minute or longer. A treatment procedure can include one to ten (or more) cycles of applying electromagnetic energy to the tooth. A fluid can circulate or otherwise move in the chamber during the treatment process, which advantageously may inhibit heating of the tooth 10 (which may cause discomfort to the patient). The movement or circulation of treatment fluid (e.g., water with a tissue dissolving agent) in the chamber 6 can bring fresh treatment fluid to tissue and organic matter as well as flush out dissolved material from the treatment site. In some treatments using electromagnetic radiation, movement of the treatment fluid (for example small- or large scale rotational flows or turbulent flow) can increase the effectiveness of the cleaning (as compared to a treatment with little or no fluid circulation).

In some implementations, electromagnetic energy can be added to other fluid motion generation modalities. For example, electromagnetic energy can be delivered to a chamber in which another pressure wave generator (e.g., a liquid jet) is used to generate the acoustic waves.

iv. Acoustic Energy

Acoustic energy (e.g., ultrasonic, sonic, audible, and/or lower frequencies) can be generated from electric energy transferred to, e.g., an ultrasound or other transducer or an ultrasonic tip (or file or needle) that creates acoustic waves in the treatment fluid. The ultrasonic or other type of acoustic transducer can comprise a piezoelectric crystal that physically oscillates in response to an electrical signal or a magnetostrictive element that converts electromagnetic energy into mechanical energy. The transducer can be disposed in the treatment fluid, for example, in the fluid inside the chamber. As explained herein, ultrasonic or other acoustic devices used with the embodiments disclosed herein are preferably broadband and/or multi-frequency devices.

v. Further Properties of Some Pressure Wave Generators

A pressure wave generator 5 can be placed at a desired location with respect to the tooth 10. The pressure wave generator 5 creates pressure waves within the fluid 22 inside the chamber 6 and/or tooth 10 (the generation of acoustic waves may or may not create or cause cavitation). The acoustic or pressure waves 23 propagate throughout the fluid 22 inside the chamber 6 of the tooth coupler 3 and/or in a tooth chamber of the tooth 10, with the fluid 22 in the chamber 6 or tooth 10 serving as a propagation medium for the pressure waves 23. The pressure waves 23 can also propagate through tooth material (e.g., dentin). It is believed, although not required, that as a result of application of a sufficiently high-intensity acoustic wave, acoustic cavitation may occur. The collapse of cavitation bubbles may induce, cause, or be involved in a number of processes described herein such as, e.g., sonochemistry, tissue dissociation, tissue delamination, sonoporation, and/or removal of calcified structures. In some embodiments, the pressure wave generator can be configured such that the acoustic waves (and/or cavitation) do not substantially break down natural dentin in the tooth 110. The acoustic wave field by itself or in addition to cavitation may be involved in one or more of the abovementioned processes.

In some implementations, the pressure wave generator 5 generates primary cavitation, which creates acoustic waves, which may in turn lead to secondary cavitation. The secondary cavitation may be weaker than the primary cavitation and may be non-inertial cavitation. In other implementations, the pressure wave generator 5 generates acoustic waves directly, which may lead to secondary cavitation.

Additional details of pressure wave generators (e.g., which may comprise a pressure wave generator) that may be suitable for use with the embodiments disclosed herein may be found, e.g., in ¶¶[0191]-[0217], and various other portions of U.S. Patent Publication No. US 2012/0237893, published Sep. 20, 2012, which is incorporated by reference herein for all purposes.

c. Enhancement of Cleaning Using Large-Scale Fluid Motion

In some arrangements, bulk fluid motion 24 (e.g., fluid rotation, convection, planar flow, chaotic flow, etc.) can enhance the cleaning of unhealthy material from a diseased tooth. For example, the fluid motion 24 generated in the chamber 6 and/or tooth 10 can impart relatively large momentum to the tooth, which can help dissociate and irrigate unhealthy materials from the tooth. Furthermore, the fluid motion 24 can induce vortices and/or swirl in the tooth 10 that can result in negative pressures (or low positive pressures) near the apical opening 15 of the tooth 10. The resulting negative pressures at the apical opening 15 can prevent or reduce an amount of material extruded through the apical opening 15 and into the jaw of the patient. By preventing or reducing the amount of extruded material, the risk of pain and discomfort as well as infection can be lowered or eliminated, and patient outcomes and comfort can be substantially improved.

In addition, due to relatively short time scales of the chemical reaction processes between the fluid 22 and the unhealthy materials as compared to that of diffusion mechanisms, a faster mechanism of reactant delivery such as "macroscopic" liquid circulation may be advantageous in some of the embodiments disclosed herein. For example, liquid circulation with a time scale comparable to (and preferably faster than) that of chemical reaction may help replenish the reactants at the chemical reaction front and/or may help to remove the reaction byproducts from the reaction site. The relatively large convective time scale, which may relate to effectiveness of the convection process, can be adjusted and/or optimized depending on, e.g., the location and characteristics of the source of circulation. Furthermore, it should be appreciated that the introduction of liquid circulation or other fluid motion 24 generally does not eliminate the diffusion process, which may still remain effective within a thin microscopic layer at the chemical reaction front. Liquid circulation can also cause a strong irrigation effect at the treatment site (e.g. removing diseased tissue deep in the canal 13 and/or tubules and small spaces and cracks of the tooth 10) and may therefore result in loosening and/or removing large and small pieces of debris from the treatment site.

In some arrangements, various properties can be adjusted to enhance bulk fluid motion and/or fluid circulation, e.g., fluid motion in the chamber 6 of the tooth coupler 3. For example, the position of the pressure wave generator 5 relative to the location of the treatment site can be adjusted. Furthermore, in some embodiments, the pressure wave generator 5 can be disposed adjacent the access opening 18 formed in the tooth and/or adjacent an access port of the tooth coupler 3. The geometry of the space surrounding the pressure wave generator 5 and treatment site (e.g., the geometry of the tooth coupler 3) can also be varied. It should also be appreciated that circulation may be affected by the viscosity of the fluid 22 and/or the mechanism of action of the pressure wave generator 5. For example, the pressure wave generator 5, such as a jet of liquid ejected through an inlet opening, a stirrer such as a propeller or a vibrating object, etc., can be selected to enhance fluid motion of the treatment fluid. In some aspects, the input power of the source of liquid circulation can also be adjusted, such as the source of a pump that drives a liquid jet in some embodiments.

2. Enhancement of Other Dental and Endodontic Procedures

In some embodiments, the pressure wave generators 5 disclosed herein can enhance other dental and endodontic procedures. For example, after cleaning a tooth (e.g., a root canal inside the tooth, a carious region on or near an exterior surface of the tooth, etc.), the treatment region can be filled with an obturation or filler material. The clinician can also restore damaged or diseased tooth material by building up the tooth using a suitable restoration material. In some embodiments, a filler material can be supplied to the treatment region as a flowable material and can be hardened to fill the treatment region (e.g., the cleaned root canal or carious region, etc.). In some embodiments, a pressure wave generator 5 can be activated to supply the obturation material throughout the treatment region.

For example, after a root canal procedure, the pressure wave generator can supply the flowable obturation material into the tooth and root canal. The large-scale fluid movement generated by the pressure wave generator 5 can assist in propagating the obturation material throughout relatively large spaces, such as the main root canal or canals. For example, the pressure wave generator 5 may introduce sufficient momentum such that the flowable obturation material propagates throughout the canal space without introducing additional instrumentation into the tooth. For example, the bulk fluid motion of the obturation material into the canal may be such that the clinician may not need to or desire to enlarge the canals. By reducing or eliminating canal enlargement, patient outcomes and pain levels can be improved. In some arrangements, the bulk fluid motion of the flowable obturation material can be generated at relatively low frequencies produced by the pressure wave generator.

In addition to generating large-scale or bulk fluid motion of the obturation material throughout the canal, the pressure wave generators 5 disclosed herein can generate higher frequency perturbations to propagate the obturation material into smaller cracks, spaces, and crevices in the tooth. For example, higher-frequency effects, such as acoustic cavitation, can assist in propagating the filler material throughout the tooth.

Accordingly, the pressure wave generators disclosed herein can enhance the filling and/or restoration of a treatment region such as a root canal, carious region of the tooth, etc. For example, the obturation material can be propagated at a distance such that it flows into the treatment region from a remote pressure wave generator 5 (which may be disposed outside the tooth). Large-scale or bulk fluid motion of the obturation material can fill larger canal spaces or other treatment regions without further enlargening the treatment region. Smaller-scale and/or higher frequency agitation by the pressure wave generator 5 can propagate the obturation material into smaller cracks and spaces of the tooth. By filling substantially all the cleaned spaces of the tooth, the disclosed methods can improve patient outcomes relative to other methods by reducing the risk of infection in spaces unfilled by the obturation material.

3. Enhancement of Treatment Procedures with Broadband Pressure Waves

Figure 2A:
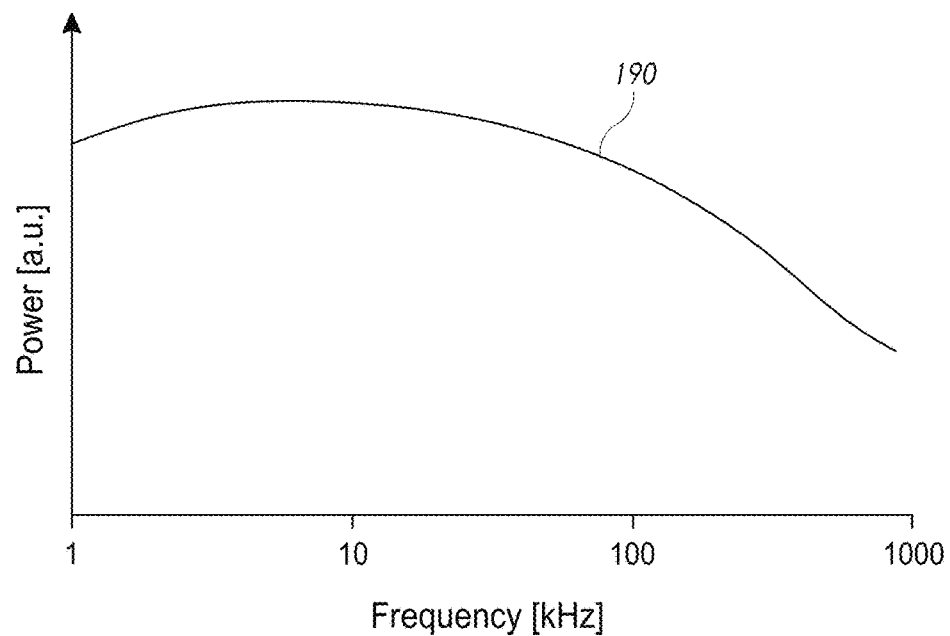
FIGS. 2A and 2B are graphs that schematically illustrate possible examples of power that can be generated by different embodiments of a pressure wave generator.
Figure 2B:
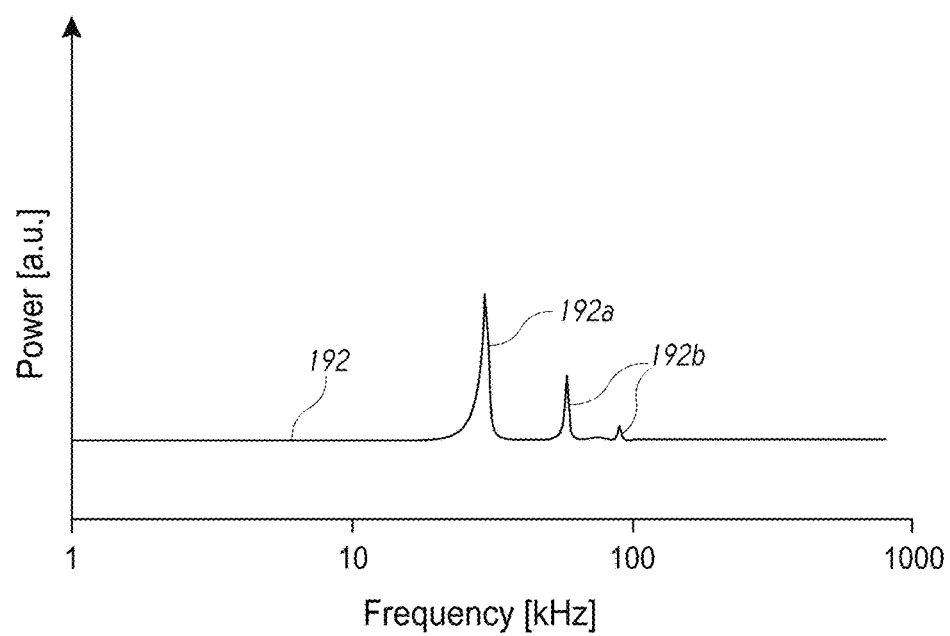

In various embodiments, disclosed herein, it can be advantageous to configure the pressure wave generator 5 to create pressure waves 23 having a broadband spectrum, e.g., including numerous or multiple frequencies of waves. For example, the generation of broadband pressure waves having multiple frequencies can assist in cleaning a treatment region of the tooth and/or in obturation or filling the treatment region. FIGS. 2A and 2B are graphs that schematically illustrate possible examples of power that can be generated by different embodiments of the pressure wave generator 5. These graphs schematically show acoustic power (in arbitrary units) on the vertical axis as a function of acoustic frequency (in kHz) on the horizontal axis. The acoustic power in the tooth may influence, cause, or increase the strength of effects including, e.g., acoustic cavitation (e.g., cavitation bubble formation and collapse, normal and shear stress formation, as well as microscale flow and microjet formation), acoustic streaming, microerosion, fluid agitation, turbulence, fluid circulation and/or rotational motion, sonoporation, sonochemistry, and so forth, which may act to dissociate organic material in or on the tooth and effectively clean the undesirable materials, e.g., undesirable organic and/or inorganic materials and deposits. In some embodiments, these effects can enhance or enable the obturation or filling of treated root canals or other treatment regions of the tooth. For example, the embodiments disclosed herein can advantageously obturate or fill substantially the entire canal(s) and/or branch structures therefrom, as explained in greater detail above. In various embodiments, the pressure wave generator can produce a pressure wave including acoustic power (at least) at frequencies above: about 1 Hz, about 0.5 kHz, about 1 kHz, about 10 kHz, about 20 kHz, about 50 kHz, about 100 kHz, or greater. The pressure wave can have acoustic power at other frequencies as well (e.g., at frequencies below the aforelisted frequencies).

The graph in FIG. 2A represents a schematic example of acoustic power generated by a liquid jet impacting a surface disposed within a chamber on or around the tooth that is substantially filled with liquid and by the interaction of the liquid jet with fluid in the chamber. This schematic example shows a broadband spectrum 190 of acoustic power with significant power extending from about 1 Hz to about 1000 kHz, including, e.g., significant power in a range of about 1 kHz to about 1000 kHz (e.g., the bandwidth can be about 1000 kHz). The bandwidth of the acoustic energy spectrum may, in some cases, be measured in terms of the 3-decibel (3-dB) bandwidth (e.g., the full-width at half-maximum or FWHM of the acoustic power spectrum). In various examples, a broadband acoustic power spectrum can include significant power in a bandwidth in a range from about 1 Hz to about 500 kHz, in a range from about 1 kHz to about 500 kHz, in a range from about 10 kHz to about 100 kHz, or some other range of frequencies. In some implementations, a broadband spectrum can include acoustic power above about 1 MHz. In some embodiments, the pressure wave generator can produce broadband acoustic power with peak power at about 10 kHz and a bandwidth of about 100 kHz. In various embodiments, the bandwidth of a broadband acoustic power spectrum is greater than about 10 kHz, greater than about 50 kHz, greater than about 100 kHz, greater than about 250 kHz, greater than about 500 kHz, greater than about 1 MHz, or some other value. In some cleaning methods, acoustic power between about 1 Hz and about 200 kHz, e.g., in a range of about 20 kHz to about 200 kHz may be particularly effective at cleaning teeth. The acoustic power can have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). In some arrangements, the broadband spectrum 190 can include one or more peaks, e.g., peaks in the audible, ultrasonic, and/or megasonic frequency ranges.

The graph in FIG. 2B represents a schematic example of acoustic power generated by an ultrasonic transducer disposed in a chamber on or around the tooth that is substantially filled with liquid. This schematic example shows a relatively narrowband spectrum 192 of acoustic power with a highest peak 192a near the fundamental frequency of about 30 kHz and also shows peaks 192b near the first few harmonic frequencies. The bandwidth of the acoustic power near the peak may be about 5 to 10 kHz, and can be seen to be much narrower than the bandwidth of the acoustic power schematically illustrated in FIG. 2A. In other embodiments, the bandwidth of the acoustic power can be about 1 kHz, about 5 kHz, about 10 kHz, about 20 kHz, about 50 kHz, about 100 kHz, or some other value. The acoustic power of the example spectrum 192 has most of its power at the fundamental frequency and first few harmonics, and therefore the ultrasonic transducer of this example may provide acoustic power at a relatively narrow range of frequencies (e.g., near the fundamental and harmonic frequencies). The acoustic power of the example spectrum 190 exhibits relatively broadband power (with a relatively high bandwidth compared to the spectrum 192), and the example liquid jet can provide acoustic power at significantly more frequencies than the example ultrasonic transducer. For example, the relatively broadband power of the example spectrum 190 illustrates that the example jet device provides acoustic power at these multiple frequencies with energy sufficient to break the bonds between the decayed and healthy material so as to substantially remove the decayed material from the carious region.

It is believed, although not required, that pressure waves having broadband acoustic power (see, e.g., the example shown in FIG. 2A) can generate acoustic cavitation or other means of cleaning and disinfection that is more effective at cleaning teeth (including cleaning, e.g., unhealthy materials in or on the tooth) than cavitation generated by pressure waves having a narrowband acoustic power spectrum (see, e.g., the example shown in FIG. 2B). One reason is that in a broadband spectrum the energy is delivered as substantially all length scales covered in the range and therefore targeting substantially all structures whose dimensions fall within that range of length scales. Further, broadband acoustic power can also generate sufficient energy at frequencies capable of obturating or filling a root canal or other treatment region (such as a treated carious region on an exterior surface of the tooth). For example, a broadband spectrum of acoustic power can produce a relatively broad range of bubble sizes in the cavitation cloud and on the surfaces on the tooth, and the implosion of these bubbles may be more effective at disrupting tissue than bubbles having a narrow size range. Relatively broadband acoustic power may also allow acoustic energy to work on a range of length scales, e.g., from the cellular scale up to the tissue scale. Accordingly, pressure wave generators that produce a broadband acoustic power spectrum (e.g., some embodiments of a liquid jet) can be more effective at tooth cleaning for some treatments than pressure wave generators that produce a narrowband acoustic power spectrum. In some embodiments, multiple narrowband pressure wave generators can be used to produce a relatively broad range of acoustic power. For example, multiple ultrasonic tips, each tuned to produce acoustic power at a different peak frequency, can be used. As used herein, broadband frequencies and broadband frequency spectrum is defined regardless of secondary effects such as harmonics of the main frequencies and regardless of any noise introduced by measurement or data processing (e.g., FFT); that is, these terms should be understood when only considering all main frequencies activated by the pressure wave generator.

Figure 2C:
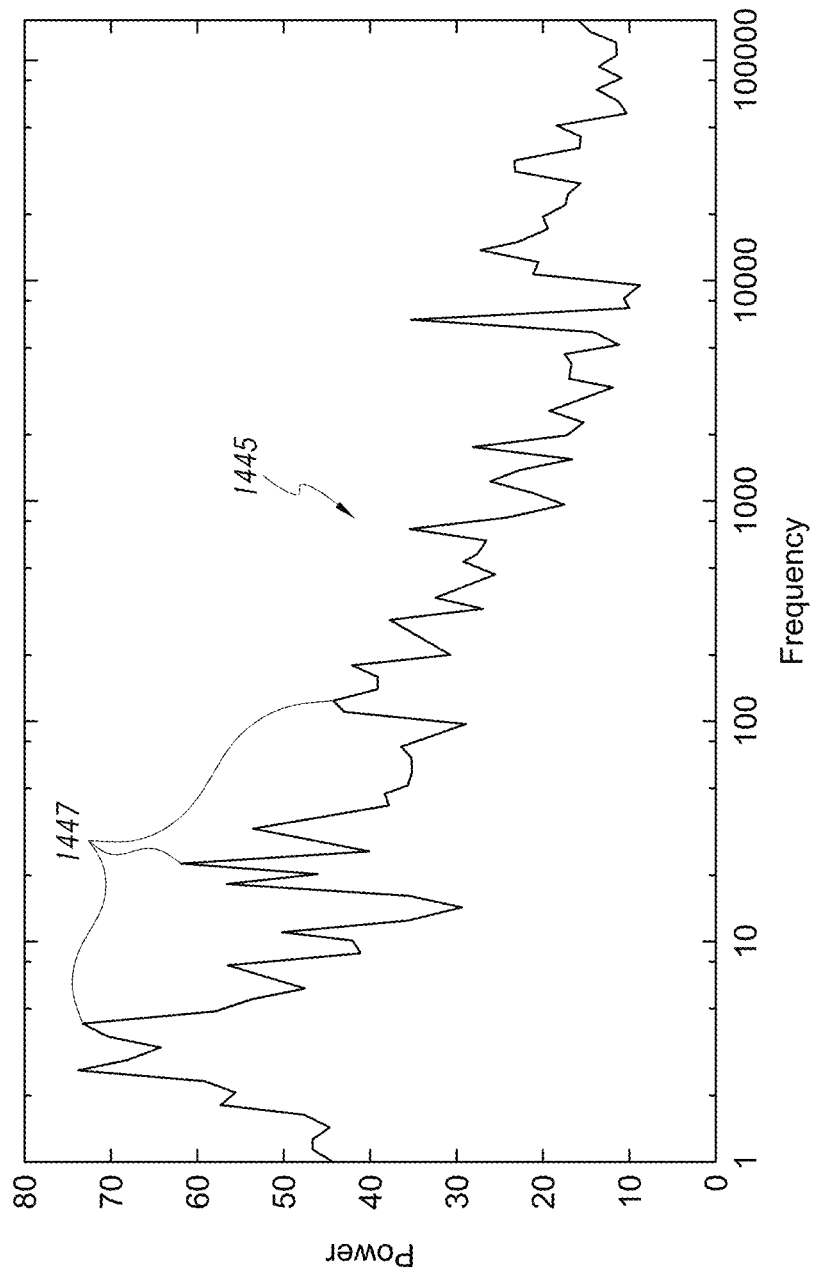
FIG. 2C is a graph of an acoustic power spectrum generated at multiple frequencies by pressure wave generators disclosed herein.

FIG. 2C is a graph of an acoustic power spectrum 1445 generated at multiple frequencies by the pressure wave generators disclosed herein. For example, the spectrum 1445 in FIG. 2C is an example of acoustic power generated by a liquid jet impacting a surface disposed within a chamber on, in, or around the tooth that is substantially filled with liquid and by the interaction of the liquid jet with fluid in the chamber. The spectrum 1445 of FIG. 2C represents acoustic power detected by a sensor spaced apart from the source of the acoustic energy, e.g., the pressure wave generator. The data was acquired inside an insulated water tank when the distance between the power wave generator and the hydrophone (e.g., sensor) being about 8 inches. The vertical axis of the plot represents a measure of acoustic power: Log ($P_{acoustic}^2$), referred to herein as "power units". The units of $P_{acoustic}$ in the measurement were µPa (micro Pascal). Thus, it should be appreciated that the actual power at the source may be of a different magnitude because the sensor is spaced from the acoustic power generator. However, the general profile of the power spectrum at the source should be the same as the spectrum 1445 detected at the sensor and plotted in FIG. 2C. It should also be understood that, although the plot shows frequencies only up to 100 KHz, the power above 100 KHz was greater than zero (although not plotted in the figures shown herein). It should further be noted that, as would be appreciated by one skilled in the art, the plot and the values would also depend on other parameters, such as, for example, the size and shape of the tank in which data was acquired, the insulation of the inner surface of the tank, the relative distance between the source (e.g., power wave generator), and the free water surface of the tank.

As shown in FIG. 2C, the spectrum 1445 can include acoustic power at multiple frequencies 1447, e.g., multiple discrete frequencies. In particular, the spectrum 1445 illustrated in FIG. 2C includes acoustic power at frequencies in a range of about 1 Hz to about 100 KHz. The acoustic power can be in a range of about 10 power units to about 80 power units at these frequencies. In some arrangements, the acoustic power can be in a range of about 30 power units to about 75 power units at frequencies in a range of about 1 Hz to about 10 kHz. In some arrangements, the acoustic power can be in a range of about 10 power units to about 30 power units at frequencies in a range of about 1 KHz to about 100 kHz. In some embodiments, for example, the broadband frequency range of the pressure waves generated by the pressure wave generators disclosed herein can comprise a substantially white noise distribution of frequencies.

Pressure wave generators that generate acoustic power associated with the spectrum 1445 of FIG. 2C can advantageously and surprisingly clean undesirable materials from teeth. As explained above, the generation of power at multiple frequencies can help to remove various types of organic and/or inorganic materials that have different material or physical characteristics, and/or different bonding strengths at various frequencies. For example, some undesirable materials may be removed from the teeth and/or gums at relatively low acoustic frequencies, while other materials may be removed from the teeth at relatively high acoustic frequencies, while still other materials may be removed at intermediate frequencies between the relatively low and relatively high frequencies. As shown in FIG. 2C, lower frequency cleaning phases can be activated at higher powers, and higher frequency cleaning phases can be activated at lower powers. In other embodiments, low frequency cleaning phases may be activated at relatively low powers, and high frequency cleaning phases may be activated at relatively high powers. Pressure wave generators that generate acoustic power at multiple frequencies (e.g., multiple discrete frequencies) are capable of cleaning undesirable materials and decayed matter from interior and/or exterior portions of teeth.

In the embodiments disclosed herein, treatment procedures can be activated to generate acoustic power at various frequency ranges for cleaning procedures and/or for obturation procedures. For example, some treatment phases may be activated at lower frequencies, and other treatment phases may be activated at higher frequencies. The pressure wave generators disclosed herein can be adapted to controllably generate acoustic power at any suitable frequencies 1447 of the spectrum 1445. For example, the pressure wave generators disclosed herein can be adapted to generate power at multiple frequencies 1447 simultaneously, e.g., such that the delivered acoustic power in a particular treatment procedure can include a desired combination of individual frequencies. For example, in some procedures, power may be generated across the entire frequency spectrum 1445. In some treatment phases, the pressure wave generator can deliver acoustic power at only relatively low frequencies, and in other treatment phases, the pressure wave generator can deliver power at only relatively high frequencies, as explained herein. Further, depending on the desired treatment procedure, the pressure wave generator can automatically or manually transition between frequencies 1447 according to a desired pattern, or can transition between frequencies 1447 randomly. In some arrangements, relatively low frequencies can be associated with large-scale bulk fluid movement, and relatively high frequencies can be associated with small-scale, high-energy oscillations.

In some embodiments, the treatment procedure may include one or more treatment phases. In each treatment phase, energy can be applied at a different frequency or band of frequencies. For example, in one phase, energy (e.g., pressure or acoustic waves) propagating at a relatively low frequency (or band of frequencies) may be generated. The low frequency pressure waves can interact with the treatment fluid in the chamber and can induce removal of large-scale dental deposits or materials. Without being limited by theory, for cleaning procedures, the low frequency pressure waves can remove a substantial portion of the unhealthy materials in the tooth. For example, the low frequency waves may have a sufficiently high energy at suitably low frequencies to remove large deposits or materials from the tooth. The acoustic power at the relatively low frequencies can include acoustic power at any suitable low-frequency band of the power spectrum of the pressure wave generator (see, e.g., FIG. 2A). For example, in some embodiments, the acoustic power in the first, low-frequency range can include one or more frequencies in a range of about 0.1 Hz to about 100 Hz, for example in a range of about 1 Hz to about 50 Hz in some arrangements. For obturation procedures, low frequency waves may be suitable for conveying obturation material through large spaces and canals of the tooth.

In another phase, acoustic energy may be generated at relatively high frequencies. At higher frequencies, the pressure wave generator can be configured to remove smaller deposits and debris in cleaning procedures. For example, at higher frequencies, the pressure waves can propagate through the treatment fluid. The higher frequency waves can remove smaller portions from relatively small locations, such as crevices, cracks, spaces, and irregular surfaces of the tooth. In some embodiments, degassed liquid can be used to enhance the removal of matter from these small spaces. When the higher frequency cleaning is performed after the lower frequency cleaning, in some embodiments, the high frequency waves (and/or intermediate frequency waves) can clean the remainder of the unhealthy material left behind from the low frequency cleaning. In the relatively high frequency phases, acoustic energy can be generated in a range of about 10 kHz to about 1000 kHz, e.g., in a range of about 100 kHz to about 500 kHz. For obturation procedures, higher frequency pressure waves may assist in filling small spaces of the tooth and canals.

In some embodiments, the treatment procedure can progress from the relatively low frequencies (or bands of frequencies) toward higher frequencies (or bands of frequencies). For example, the procedure can move from the relatively low frequency phase(s), through intermediate frequency phase(s), until the high frequency phase(s) are reached. Thus, in some embodiments, the treatment procedure can provide a gradual and/or substantially continuous transition between relatively low and relatively high frequencies. As the treatment progresses through the frequencies, unhealthy dental deposits or materials of varying size and type can be removed by the pressure wave generator. In other embodiments, however, the treatment procedure can transition or switch between frequencies (or bands of frequencies) or phases (e.g., between high, low and/or intermediate frequencies or bands of frequencies) at discrete levels. At various intermediate frequency ranges, acoustic energy can be generated in a range of about 100 Hz to about 10 kHz. For example, in some embodiments, the various phases of the treatment procedures described above may be activated by the user or clinician, or the pressure wave generator can be configured to automatically transition between the phases. In some embodiments, for example, the pressure wave generator can randomly switch between high, low, and intermediate frequencies.

Various treatment procedures may include any suitable number of treatment phases at various different frequencies. Furthermore, although various low- and high-frequency phases may be described above as occurring in a particular order, in other embodiments, the order of activating the low- and high-frequency phases, and/or any intermediate frequency phases, may be any suitable order. Furthermore, the treatment procedures and phases described herein can also be used to fill or obturate treatment regions of a tooth after cleaning. In obturation procedures, the embodiments disclosed herein can advantageously obturate or fill substantially the entire canal(s) and/or branch structures therefrom, as explained in greater detail herein.

4. Enhancing Treatment Procedures with Degassed Fluids

As described herein, the treatment fluid (and/or any of solutions added to the treatment fluid) can be degassed compared to normal liquids used in dental offices. For example, degassed distilled water can be used with or without the addition of chemical agents or solutes. For obturation and/or restoration procedures, the obturation or filling material (and components thereof) may be substantially degassed. Degassed obturation or filling materials can prevent bubbles from being or forming in the filling material, which can assist in filling small spaces of the canal system.

a. Examples of Possible Effects of Dissolved Gases in the Treatment Fluid

In some procedures, the treatment fluid can include dissolved gases (e.g., air). For example, the fluids used in dental offices generally have a normal dissolved gas content (e.g., determined from the temperature and pressure of the fluid based on Henry's law). During cleaning procedures using a pressure wave generator, the acoustic field of the pressure wave generator and/or the flow or circulation of fluids in the chamber can cause some of the dissolved gas to come out of solution and form bubbles.

The bubbles can block small passageways or cracks or surface irregularities in the tooth, and such blockages can act as if there were a "vapor lock" in the small passageways. In some such procedures, the presence of bubbles may at least partially block, impede, or redirect propagation of acoustic waves past the bubbles and may at least partially inhibit or prevent cleaning action from reaching, for example, unhealthy dental materials in tubules and small spaces of the tooth 10. The bubbles may block fluid flow or circulation from reaching these difficult-to-reach, or otherwise small, regions, which may prevent or inhibit a treatment solution from reaching these areas of the tooth.

In certain procedures, cavitation is believed to play a role in cleaning the tooth. Without wishing to be bound by any particular theory, the physical process of cavitation inception may be, in some ways, similar to boiling. One possible difference between cavitation and boiling is the thermodynamic paths that precede the formation of the vapor in the fluid. Boiling can occur when the local vapor pressure of the liquid rises above the local ambient pressure in the liquid, and sufficient energy is present to cause the phase change from liquid to a gas. It is believed that cavitation inception can occur when the local ambient pressure in the liquid decreases sufficiently below the saturated vapor pressure, which has a value given in part by the tensile strength of the liquid at the local temperature. Therefore, it is believed, although not required, that cavitation inception is not determined by the vapor pressure, but instead by the pressure of the largest nuclei, or by the difference between the vapor pressure and the pressure of the largest nuclei. As such, it is believed that subjecting a fluid to a pressure slightly lower than the vapor pressure generally does not cause cavitation inception. However, the solubility of a gas in a liquid is proportional to pressure; therefore lowering the pressure may tend to cause some of the dissolved gas inside the fluid to be released in the form of gas bubbles that are relatively large compared to the size of bubbles formed at cavitation inception. These relatively large gas bubbles may be misinterpreted as being vapor cavitation bubbles, and their presence in a fluid may have been mistakenly described in certain reports in the literature as being caused by cavitation, when cavitation may not have been present.

In the last stage of collapse of vapor cavitation bubbles, the velocity of the bubble wall may even exceed the speed of sound and create strong shock waves inside the fluid. The vapor cavitation bubble may also contain some amount of gas, which may act as a buffer and slow down the rate of collapse and reduce the intensity of the shockwaves. Therefore, in certain procedures that utilize cavitation bubbles for tooth cleaning, it may be advantageous to reduce the amount of the dissolved air in the fluid to prevent such losses.

The presence of bubbles that have come out of solution from the treatment fluid may lead to other disadvantages during certain procedures. For example, if the pressure wave generator produces cavitation, the agitation (e.g. pressure drop) used to induce the cavitation may cause the release of the dissolved air content before the water molecules have a chance to form a cavitation bubble. The already-formed gas bubble may act as a nucleation site for the water molecules during the phase change (which was intended to form a cavitation bubble). When the agitation is over, the cavitation bubble is expected to collapse and create pressure waves. However, cavitation bubble collapse might happen with reduced efficiency, because the gas-filled bubble may not collapse and may instead remain as a bubble. Thus, the presence of gas in the treatment fluid may reduce the effectiveness of the cavitation process as many of the cavitation bubbles may be wasted by merging with gas-filled bubbles. Additionally, bubbles in the fluid may act as a cushion to damp pressure waves propagating in the region of the fluid comprising the bubbles, which may disrupt effective propagation of the pressure waves past the bubbles. Some bubbles may either form on or between tooth surfaces, or be transferred there by the flow or circulation of fluid in the tooth. The bubbles may be hard to remove due to relatively high surface tension forces. This may result in blocking the transfer of chemicals and/or pressure waves into the irregular surfaces and small spaces in and between teeth, and therefore may disrupt or reduce the efficacy of the treatment. Existence of a very small amount of gas inside the fluid may however be beneficial as the gas may form very small volume bubbles which then act as the nucleation site for vapor cavitation to occur (and therefore facilitate vapor cavitation), and due to their small volume compared to the volume of the actual vapor cavitation, their damping and interrupting effects may be negligible.

b. Examples of Degassed Treatment Fluids

Accordingly, it may be advantageous in some systems and methods to use a degassed fluid, which can inhibit, reduce, or prevent bubbles from coming out of solution during treatments as compared to systems and methods that use normal (e.g., non-degassed) fluids. In dental procedures in which the treatment fluid has a reduced gas content (compared with the normal fluids) tooth surfaces or tiny spaces in the tooth may be free of bubbles that have come out of solution. Acoustic waves generated by the pressure wave generator can propagate through the degassed fluid to reach and clean the surfaces, cracks, and tooth spaces and cavities. In some procedures, the degassed fluid can be able to penetrate spaces as small as about 500 microns, 200 microns, 100 microns, 10 microns, 5 microns, 1 micron, or smaller, because the degassed fluid is sufficiently gas-free that bubbles are inhibited from coming out of solution and blocking these spaces (as compared to use of fluids with normal dissolved gas content).

For example, in some systems and methods, the degassed fluid can have a dissolved gas content that is reduced when compared to the "normal" gas content of water. For example, according to Henry's law, the "normal" amount of dissolved air in water (at 25 C and 1 atmosphere) is about 23 mg/L, which includes about 9 mg/L of dissolved oxygen and about 14 mg/L of dissolved nitrogen. In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid can be reduced to approximately 5%-50% or 1%-70% of the normal gas content of the fluid. In some treatments, the dissolved gas content can be less than about 70%, less than about 50%, less than about 40%, less than about 30%, less than about 20%, less than about 10%, less than about 5%, or less than about 1% of the normal gas amount.

In some embodiments, the amount of dissolved gas in the degassed fluid can be measured in terms of the amount of dissolved oxygen (rather than the amount of dissolved air), because the amount of dissolved oxygen can be more readily measured (e.g., via titration or optical or electrochemical sensors) than the amount of dissolved air in the fluid. Thus, a measurement of dissolved oxygen in the fluid can serve as a proxy for the amount of dissolved air in the fluid. In some such embodiments, the amount of dissolved oxygen in the degassed fluid can be in a range from about 1 mg/L to about 3 mg/L, in a range from about 0.5 mg/L to about 7 mg/L, or some other range. The amount of dissolved oxygen in the degassed fluid can be less than about 7 mg/L, less than about 6 mg/L, less than about 5 mg/L, less than about 4 mg/L, less than about 3 mg/L, less than about 2 mg/L, or less than about 1 mg/L.

In some embodiments, the amount of dissolved gas in the degassed fluid can be in a range from about 2 mg/L to about 20 mg/L, in a range from about 1 mg/L to about 12 mg/L, or some other range. The amount of dissolved gas in the degassed fluid can be less than about 20 mg/L, less than about 18 mg/L, less than about 15 mg/L, less than about 12 mg/L, less than about 10 mg/L, less than about 8 mg/L, less than about 6 mg/L, less than about 4 mg/L, or less than about 2 mg/L.

In other embodiments, the amount of dissolved gas can be measured in terms of air or oxygen percentage per unit volume. For example, the amount of dissolved oxygen (or dissolved air) can be less than about 5% by volume, less than about 1% by volume, less than about 0.5% by volume, or less than about 0.1% by volume.

The amount of dissolved gas in a liquid can be measured in terms of a physical property such as, e.g., fluid viscosity or surface tension. For example, degassing water tends to increase its surface tension. The surface tension of non-degassed water is about 72 mN/m at 20° C. In some embodiments, the surface tension of degassed water can be about 1%, 5%, or 10% greater than non-degassed water.

In some treatment methods, one or more secondary fluids can be added to a primary degassed fluid (e.g., an antiseptic solution can be added to degassed distilled water). In some such methods, the secondary solution(s) can be degassed before being added to the primary degassed fluid. In other applications, the primary degassed fluid can be sufficiently degassed such that inclusion of the secondary fluids (which can have normal dissolved gas content) does not increase the gas content of the combined fluids above what is desired for a particular dental treatment.

In various implementations, the treatment fluid can be provided as degassed liquid inside sealed bags or containers. The fluid can be degassed in a separate setup in the operatory before being added to a fluid reservoir. In an example of an "in-line" implementation, the fluid can be degassed as it flows through the system, for example, by passing the fluid through a degassing unit attached along a fluid line (e.g., the fluid inlet). Examples of degassing units that can be used in various embodiments include: a Liqui-Cel® MiniModule® Membrane Contactor (e.g., models 1.7×5.5 or 1.7×8.75) available from Membrana-Charlotte (Charlotte, N.C.); a PermSelect® silicone membrane module (e.g., model PDM-SXA-2500) available from MedArray, Inc. (Ann Arbor, Mich.); and a FiberFlo® hollow fiber cartridge filter (0.03 micron absolute) available from Mar Cor Purification (Skippack, Pa.). The degassing can be done using any of the following degassing techniques or combinations of thereof: heating, helium sparging, vacuum degassing, filtering, freeze-pump-thawing, and sonication.

In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but can be passed through a de-bubbler to remove the small gas bubbles from the fluid.

In some embodiments, a degassing system can include a dissolved gas sensor to determine whether the treatment fluid is sufficiently degassed for a particular treatment. A dissolved gas sensor can be disposed downstream of a mixing system and used to determine whether mixing of solutes has increased the dissolved gas content of the treatment fluid after addition of solutes, if any. A solute source can include a dissolved gas sensor. For example, a dissolved gas sensor can measure the amount of dissolved oxygen in the fluid as a proxy for the total amount of dissolved gas in the fluid, since dissolved oxygen can be measured more readily than dissolved gas (e.g., nitrogen or helium). Dissolved gas content can be inferred from dissolved oxygen content based at least partly on the ratio of oxygen to total gas in air (e.g., oxygen is about 21% of air by volume). Dissolved gas sensors can include electrochemical sensors, optical sensors, or sensors that perform a dissolved gas analysis. Examples of dissolved gas sensors that can be used with embodiments of various systems disclosed herein include a Pro-Oceanus GTD-Pro or HGTD dissolved gas sensor available from Pro-Oceanus Systems Inc. (Nova Scotia, Canada) and a D-Opto dissolved oxygen sensor available from Zebra-Tech Ltd. (Nelson, New Zealand). In some implementations, a sample of the treatment can be obtained and gases in the sample can be extracted using a vacuum unit. The extracted gases can be analyzed using a gas chromatograph to determine dissolved gas content of the fluid (and composition of the gases in some cases).

Accordingly, fluid delivered to the tooth from a fluid inlet and/or the fluid used to generate the jet in a liquid jet device can comprise a degassed fluid that has a dissolved gas content less than normal fluid. The degassed fluid can be used, for example, to generate the high-velocity liquid beam for generating acoustic waves, to substantially fill or irrigate a chamber, to provide a propagation medium for acoustic waves, to inhibit formation of air (or gas) bubbles in the chamber, and/or to provide flow of the degassed fluid into small spaces in the tooth (e.g., cracks, irregular surfaces, tubules, etc.). In embodiments utilizing a liquid jet, use of a degassed fluid can inhibit bubbles from forming in the jet due to the pressure drop at a nozzle orifice where the liquid jet is formed.

Thus, examples of methods for dental and/or endodontic treatment comprise flowing a degassed fluid onto a tooth or tooth surface or into a chamber. The degassed fluid can comprise a tissue dissolving agent and/or a decalcifying agent. The degassed fluid can have a dissolved oxygen content less than about 9 mg/L, less than about 7 mg/L, less than about 5 mg/L, less than about 3 mg/L, less than about 1 mg/L, or some other value. A fluid for treatment can comprise a degassed fluid with a dissolved oxygen content less than about 9 mg/L, less than about 7 mg/L, less than about 5 mg/L, less than about 3 mg/L, less than about 1 mg/L, or some other value. The fluid can comprise a tissue dissolving agent and/or a decalcifying agent. For example, the degassed fluid can comprise an aqueous solution of less than about 6% by volume of a tissue dissolving agent and/or less than about 20% by volume of a decalcifying agent.

Figure 3A:
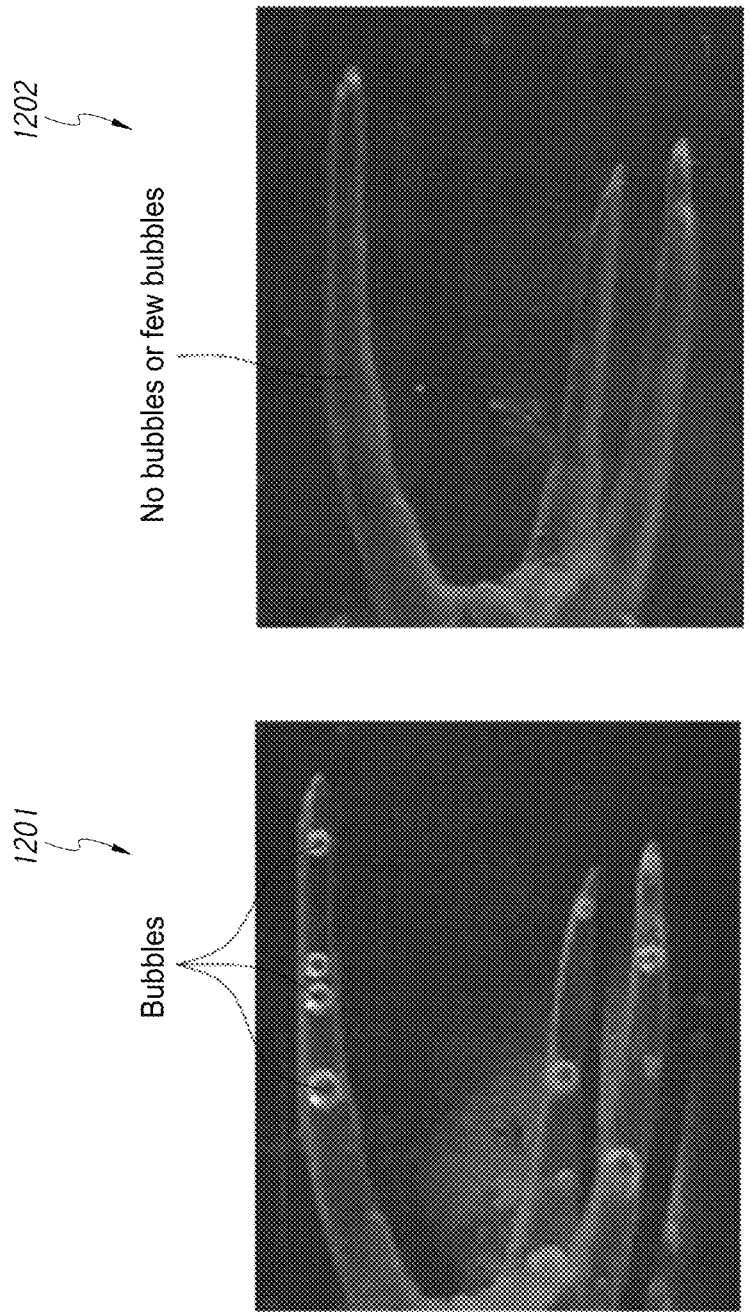
FIG. 3A illustrates images of root canals that compare the use of non-degassed liquid and degassed liquid in the disclosed pressure wave generators.
Figure 3B:
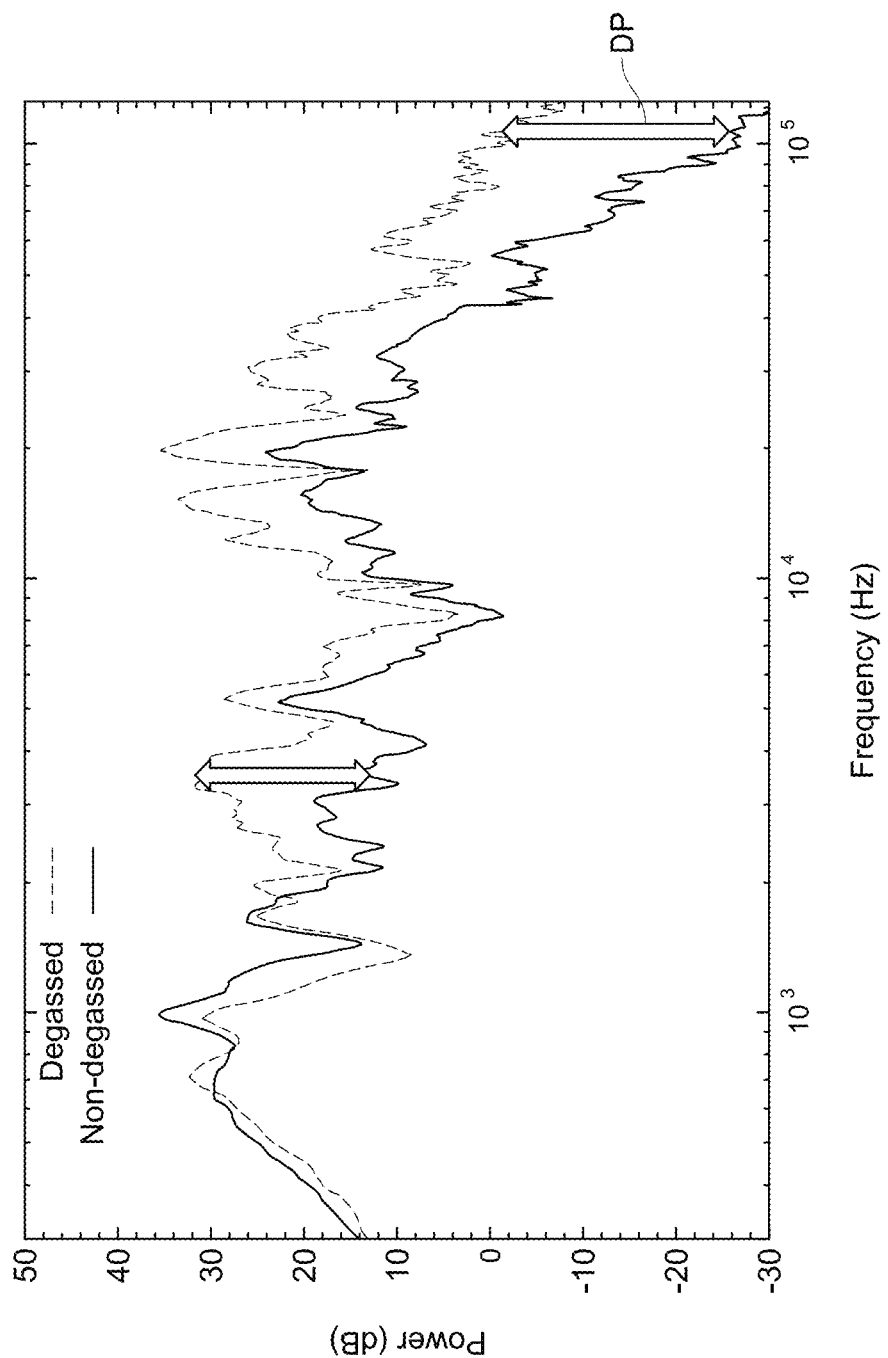
FIG. 3B is a plot comparing the power output for techniques using non-degassed and degassed liquids.

FIG. 3A illustrates images of root canals that compare the use of non-degassed liquid and degassed liquid in the disclosed pressure wave generators for a cleaning procedure. As shown in image 1201 on the left side of FIG. 3A, the use of non-degassed liquid may cause bubbles to form in the canals, which may inhibit the propagation of energy in some arrangements. As shown in image 1202 on the right side of FIG. 3A, the use of degassed liquid may substantially prevent the formation of bubbles in the root canals when exposed to broadband acoustic or pressure waves. FIG. 3B is a plot comparing the power output for techniques using non-degassed and degassed liquids. The power outputs plotted in FIG. 3B are measured based on the liquid jet device described herein. As shown in FIG. 3B, at higher acoustic frequencies, the use of degassed liquid in the disclosed systems can generate significantly more power than in techniques using non-degassed liquid. As illustrated in FIG. 3B, for example, at high acoustic frequencies, the difference between power generated by degassed and non-degassed liquids can be given by $\Delta P$, which can be in a range of about 5 dB to about 25 dB for frequencies in a range of about 20 kHz to about 200 kHz. For example, for frequencies in a range of about 70 kHz to about 200 kHz, $\Delta P$ can be in a range of about 10 dB to about 25 dB. At lower frequencies, the differences in power generated by degassed and non-degassed techniques may not be noticeable. At lower frequencies, relatively high powers may be generated even with non-degassed liquid because low frequency, large-scale fluid motion may produce substantial momentum that contributes to the cleaning of the tooth.

II. Examples of Handpieces

FIG. 4A is a schematic side view of a tooth coupler comprising a handpiece 3A having a cleaning mode and an obturation or filling mode. FIG. 4B is a schematic side cross-sectional view of the handpiece 3A shown in FIG. 4A. The dental handpiece 3A can include a body or housing shaped to be gripped by the clinician. In some embodiments, the pressure wave generator 5 can be coupled to or formed with a distal portion of the handpiece 3A. Before a treatment procedure (e.g., a cleaning procedure, an obturation procedure, a restorative procedure, etc.), the clinician can connect the handpiece 3A to an interface member 4 of the system 1. The interface member 4 can be in fluid and/or electrical communication with the console 2 (see FIGS. 1A-1D), which can be configured to control the treatment procedures. The interface member 4 may be similar to or the same as the interface members disclosed in U.S. patent application Ser. No. 14/172,809, filed on Feb. 4, 2014, entitled "DENTAL TREATMENT SYSTEM," and in U.S. Patent Publication No. US 2012/0237893, each of which is incorporated by reference herein in its entirety and for all purposes. In some embodiments, the handpiece 3A can comprise a wireless chip (such as a radio frequency identification, or RFID, chip) configured to wirelessly communicate with the console 2 or with a reader that is in communication with the console 2. The RFID chip can be used to confirm what type of handpiece 3A is being used with the system 1. For example, the RFID chip can store information regarding the handpiece 3A, such as whether the handpiece 3A is a cleaning handpiece, and obturation handpiece, or both. This information can be used to track information regarding the treatment procedure and/or to ensure that the proper procedure is being performed with the particular handpiece 3A. Additional details of such a wireless chip system for the handpiece are disclosed in U.S. patent application Ser. No. 14/172,809, filed on Feb. 4, 2014, entitled "DENTAL TREATMENT SYSTEM," which is incorporated by reference herein in its entirety and for all purposes.

The clinician can manipulate the handpiece 3A such that the pressure wave generator 5 is positioned near the treatment region on or in the tooth. The clinician can activate the pressure wave generator 5 using controls on the console 2 and/or the handpiece 3A, and can perform the desired treatment procedure. After performing the treatment procedure, the clinician can disconnect the handpiece 3A from the interface member 4 and can remove the handpiece 3A from the system 1. The handpiece 3A shown in FIGS. 4A-4B can advantageously be configured to clean a tooth when the handpiece 3A is in the cleaning mode and to obturate or fill the tooth when the handpiece is in the obturation mode. In other embodiments, the handpiece 3A may only be configured to clean the tooth or may only be configured to obturate the treatment region. As explained above, the clinician can position the handpiece 3A against the treatment region during a treatment procedure. The handpiece 3A in FIGS. 4A-4B can include a sealing cap 40 at a distal portion 19 of the handpiece 3A. The sealing cap 40 can be sized and shaped to be positioned against a portion of a tooth to be treated. In some arrangements, the cap 40 can be held against the treatment tooth by the clinician during the procedure. In other arrangements, the cap 40 can be attached to the tooth.

In some embodiments, a pressure wave generator 5 can be disposed near the distal portion 19 of the handpiece 19. For example, as shown in FIG. 4B, the sealing cap 40 can be disposed about the pressure wave generator 5. The sealing cap 40 can at least partially define a chamber 6 configured to retain fluid during a treatment procedure. The pressure wave generator 5 can be any suitable apparatus configured to generate pressure waves sufficient to clean and/or obturate or fill a tooth, as explained in more detail herein. In the embodiment of FIGS. 4A-4B, the pressure wave generator 5 comprises a fluid jet device. For example, the pressure wave generator 5 can comprise a guide tube 21 having one or more openings 42 near a distal portion of the guide tube 21. However, as explained herein, other types of pressure wave generators may be suitable.

A high pressure supply line 26 and a waste line 44 can pass through the handpiece 3A and to the console 2 by way of an interface member 4 that couples the handpiece 3A to various conduits coupled to the console 2. The high pressure supply line 26 can extend from the console 2 (see FIG. 1A) to the handpiece 3A and can be configured to convey pressurized fluid to the guide tube 21. For example, the high pressure supply line 26 can be in fluid communication with a high pressure pump and other components in the console 2. The pump can pressurize the fluid (e.g., treatment fluid) such that the fluid passes through the handpiece 3A along the supply line 26 at relatively high pressures. Additional examples of systems including high pressure pumps, fluid supply lines, and other system components that can be used in the embodiments disclosed herein may be found in FIGS. 4-5H and the associated disclosure of U.S. patent application Ser. No. 14/172,809, filed on Feb. 4, 2014, entitled "DENTAL TREATMENT SYSTEM," and in U.S. Patent Publication No. US 2012/0237,893, each of which is incorporated by reference herein in its entirety and for all purposes.

As explained herein, during a cleaning procedure, high pressure cleaning fluids (e.g., water, EDTA, bleach, etc.) may be conveyed through the high pressure supply line 26 to the guide tube 21. A nozzle orifice (not shown) at the distal portion 19 of the handpiece 3A can be configured to form a liquid jet that passes along the guide tube 21. During a cleaning procedure, the liquid jet can pass through treatment fluid contained in the chamber 6 formed at least in part by the sealing cap 40. Interaction of the jet with the fluid in the chamber 6 (e.g., by way of the opening(s) 42) can generate pressure waves that propagate through the treatment region to substantially clean the tooth, including small spaces and cracks in the tooth. An impingement surface 33 can be disposed at the distal end of the guide tube 21 and can be shaped to prevent the jet from damaging the anatomy. The jet can impact the impingement surface 33, and the cleaning fluids can pass through the opening(s) 42 and into the treatment region to assist in cleaning the treatment region.

Similarly, during an obturation procedure, a flowable obturation material can be conveyed along the high pressure supply line 26 and can also form a jet that passes through the guide tube 21. Interaction of the jet with the surrounding fluid (such as flowable obturation material that fills the chamber 6) by way of the opening 42 can generate pressure waves, which may cause the flowable obturation material to fill small spaces and cracks in the tooth. The flowable obturation material can thus pass through the same opening(s) 42 as the cleaning fluid. When the flowable obturation material hardens or is cured, the obturation material can substantially fill the treatment region to prevent bacteria or other undesirable materials from reforming in the cleaned treatment region. The console 2 may comprise pumps and degassers. For example, the console can include high pressure pumps for pressurizing the obturation material and a degassing apparatus for degassing the obturation material. In the embodiment of FIGS. 4A-4B, the obturation or filling material in the reservoir 27 may be degassed before being disposed in the handpiece 3A.

One or more suction ports 43 can also be formed near the distal portion 19 of the handpiece 3A. The suction port 43 can fluidly communicate with the waste line 44, which can be driven by a vacuum pump (or other suitable suction system). Waste fluids can be drawn into the waste line 44 by way of the suction port 43. The waste fluids can be passed to a suitable waste collection system for disposal.

The handpiece 3A can include a switch 25 configured to change between treatment modes. The switch 25 can comprise a rotatable member that switches between a cleaning branch lumen 28 and an obturation or filling material reservoir 27. In some arrangements, the rotatable member of the switch 25 can comprise a tubular member through which suitable flowable materials can pass. For example, the switch 25 can be moved to a cleaning mode 25A, in which cleaning fluids can pass through the cleaning branch 28 of the high pressure supply line 26 to the guide tube 21 at the distal portion 19 of the handpiece 3A. The clinician may also interact with the console 2 to activate the cleaning procedure. When the switch 25 is in the cleaning mode 25A, the pressurized cleaning fluids (e.g., water, EDTA, bleach, etc.) may pass through the interface member 4, through the switch 25, and into the cleaning branch lumen 28. The cleaning branch lumen 28 can rejoin the primary supply line 26 distal the switch 25, and the cleaning fluid can be conveyed to the guide tube 21. When the cleaning fluids interact with surrounding fluid in the chamber 6, pressure waves can propagate through the treatment region. The generated pressure waves can cause the cleaning fluids to pass through tiny spaces and cracks of the treatment region to substantially clean the tooth.

In the embodiments disclosed herein, the reservoir 27 may comprise walls that have weakened portions that communicate with the supply line 26. When fluid (e.g., the obturation or filling material) is driven with a sufficiently high pressure, the fluid can break through the weakened portions of the wall to create an opening between the supply line 26 and the reservoir 27. The pressurized fluid can flow through the opening in some arrangements. Still other connections between the reservoirs and fluid supply lines may be suitable, including, e.g., valves, etc. The volume of the reservoir 27 may be sufficiently large so as to retain sufficient filing material for the filling procedure. For example, in some embodiments, the volume of the reservoir should be sized to hold a volume at least as large as the volume of the treatment region (e.g., the volume of the tooth interior for root canal treatments) plus the volume of the supply line 26 between the reservoir 27 and the treatment region. The additional volume of material may be useful in ensuring that the pressure wave generator 5 is supplied with sufficient materials so as to be able to generate sufficient pressure waves to fill the treatment region.

When the cleaning treatment is complete, the clinician can move the switch from the cleaning mode 25A to an obturation or filling mode 25B. The clinician can interact with the console 2 to activate an obturation procedure in some embodiments. The obturation reservoir 27 can be at least partially filled with an obturation or filler material. In some embodiments, the obturation material in the reservoir 27 is in a flowable state, and high pressure fluid can pass through the supply line 26 and can drive the flowable obturation material from the reservoir 27, through the supply line 26, and out into the treatment region by way of the guide tube 21 and opening(s) 42. In other arrangements, the pressurized fluid can drive a plunger (see FIGS. 5A-5B), which can cause the obturation material to flow into the treatment region through the guide tube 21 and opening(s) 42. Once the obturation material fills the treatment region, the obturation material can be hardened or cured in any suitable manner.

It should be appreciated that any suitable obturation material in its flowable state may be used to fill or obturate the treatment region of the tooth, including any of the obturation materials described herein. For example, the obturation material in its flowable state may have a viscosity and various other fluid properties that are selected to form a fluid jet when passing through an orifice near a proximal end of the guide tube 21. In some embodiments, the obturation material can comprise a powder, solid, or semi-solid material that can be dissolved in a suitable liquid (e.g., the pressurized liquid that is passed through the supply line 26 to drive the obturation material to the guide tube 21 and tooth), resulting in a flowable obturation material. For example, water can be driven through the high pressure supply line 26. When the switch 25 is switched to the obturation mode 25B, the water can mix, dissolve, or otherwise carry a base obturation material (such as a powder) to the treatment region. In other embodiments, the obturation material may be in a flowable state when stored in the reservoir 27 of the handpiece 3A.

The handpiece 3A can be used in any suitable dental cleaning treatment. For example, the handpiece 3A can be used to clean a root canal of the tooth. In such arrangements, the sealing cap 40 can be sized and shaped to be positioned against an occlusal surface of the tooth, and the pressure wave generator 5 can be disposed inside or outside the tooth chamber. Cleaning fluids can be used to form a liquid jet to clean the root canal spaces, tubules, and tiny cracks and spaces of the interior of the tooth. Once the root canal is cleaned, the clinician can switch from the cleaning mode 25A on the handpiece 3A to the obturation mode 25B. Additional details of dental platforms for root canal treatments may be found throughout U.S. Patent Publication No. US 2012/0237893, filed on Oct. 21, 2011, which is incorporated by reference herein in its entirety and for all purposes.

In other arrangements, the handpiece 3A can be used to clean a carious region of a tooth and to fill the cleaned region. Suitable sealing caps 40 and/or handpieces 3A that may be used to clean a carious region of the tooth may be found at least in FIGS. 1A-9B and the associated disclosure of International Application Publication No. WO 2013/142385, which is incorporated by reference herein in its entirety and for all purposes. In addition, the handpiece 3A can be used to clean undesirable dental deposits (such as plaque, calculus, biofilms, etc.) and fill or repair the cleaned regions if desired or needed. For example, suitable arrangements for cleaning undesirable dental deposits are disclosed in U.S. Patent Publication No. US 2014/0099597, which is incorporated by reference herein in its entirety and for all purposes. Still other treatment systems for treating root canals (including obturation systems using pressure wave generators) are disclosed in U.S. patent application Ser. No. 14/137,937, filed Dec. 20, 2013, which is incorporated by reference herein in its entirety and for all purposes.

Advantageously, the clinician can use a single instrument (e.g., the handpiece 3) to clean and fill the treatment tooth, which may reduce expenses, simplify the treatment procedure, and reduce treatment times. The pressure wave generator 5 can surprisingly generate pressure waves at the treatment site using cleaning fluids when in the cleaning mode 25A and using a flowable obturation material when in the obturation or filling mode 25B. For example, the clinician can prepare the tooth for a cleaning procedure and can switch the handpiece 3A to the cleaning mode. The clinician can use the handpiece 3A to clean the tooth, e.g., with the pressure wave generator 5. The pressure wave generator 5 can generate pressure waves such that the cleaning fluid and associated fluid dynamics interact with diseased materials throughout the treatment region (e.g., a root canal system, a carious region, undesirable dental deposits on an outer surface of the tooth, etc.), even in tiny spaces and cracks, to substantially clean the entire treatment region.

Once the tooth is cleaned, the clinician can switch the handpiece 3A from the cleaning mode 25A to the obturation mode 25B. The clinician can activate the handpiece 3A and/or console 2 to obturate the tooth. The pressure wave generator 5 can generate pressure waves such that the flowable obturation material is flowed into even tiny spaces and cracks in the treatment region to substantially fill or obturate the treatment region. Thus, the embodiments disclosed herein can advantageously clean and fill a treatment region using a pressure wave generator 5, which may be disposed in or coupled with a single treatment handpiece 3A. In the embodiment of FIGS. 4A-4B, the cleaning fluids and obturation material can flow through the same opening(s) 42 in the guide tube 21.

Furthermore, providing the obturation reservoir 27 in the handpiece 3A (rather than in the console or other components of the system) may facilitate more effective purging or cleaning of the console 2. For example, since the obturation material is stored in the handpiece 3A in the embodiment of FIGS. 4A-4B, the obturation material does not contaminate or clog the console 2 or other components between the handpiece 3A and console 2.

FIG. 5A is a schematic side view of a treatment handpiece 3A configured to deliver a flowable obturation or filling material to a treatment region of a tooth. FIG. 5B is a schematic side cross-sectional view of the handpiece 3A shown in FIG. 5A. Unless otherwise noted, reference numerals used in FIGS. 5A-5B may correspond to components similar to or the same as similarly-numbered components in FIGS. 4A-4B. For example, the handpiece 3A of FIGS. 5A-5B includes a pressure wave generator 5 and a sealing cap 40 at a distal portion 19 of the handpiece 3A. The pressure wave generator 5 can comprise a fluid jet device including a nozzle (not shown), a guide tube 21, one or more openings 42 in the guide tube 21, and an impingement surface 33 at a distal end of the guide tube 21. A suction port 43 can fluidly communicate with a waste line 44 configured to convey waste fluids to a waste collection system. An interface member 4 can connect the handpiece 3A to one or more conduits coupled with the console 2.

The handpiece 3A illustrated in FIGS. 5A-5B can include a fluid supply line 26 extending from the console 2 to an obturation reservoir 27A. The obturation reservoir 27A may be at least partially filled with an obturation material (or a base material that, when mixed with a liquid, forms a flowable obturation material). A plunger 29 or piston can be disposed in the reservoir 27A. Pressurized fluid (e.g., air, water, etc.) can pass through the supply line 26 and can drive the plunger 29 distally. The plunger can drive the obturation material distally through the supply line 26 to the guide tube 21. The obturation material can interact with fluids in the chamber 6, and pressure waves may be generated. The flowable obturation material can flow out of the guide tube 21 through the opening(s) 42 and can fill the treatment region, including tiny cracks and spaces in the tooth. The obturation material can be hardened or cured to prevent bacteria or other undesirable materials from forming in the treatment region.

The handpiece 3A illustrated in FIGS. 5A-5B does not include a switch that changes the handpiece to a cleaning mode. However, it should be appreciated that the plunger 29 shown in FIG. 5B can be used with the reservoir 27 of FIGS. 4A-4B in a multi-mode handpiece 3A that includes both a cleaning mode and a filling or obturation mode. The pressurized fluid that drives the piston or plunger 29 can be pressurized using the pressurization system described above with respect to U.S. application Ser. No. 14/172,809 and U.S. Patent Publication No. US 2012/0237893, each of which is incorporated by reference herein.

Figures 6A, 6B:
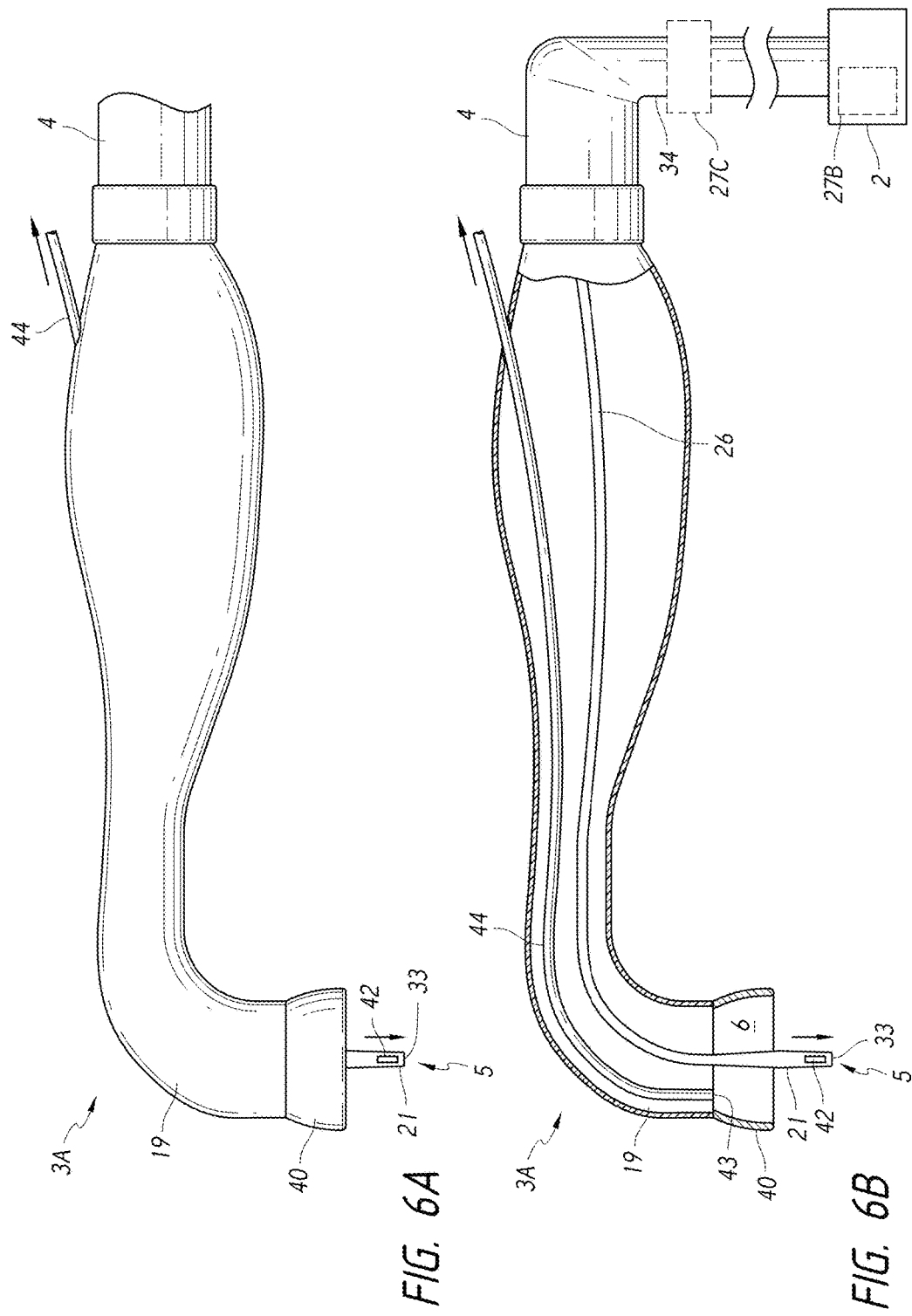
FIG. 6A is a schematic side view of a handpiece having a cleaning mode and an obturation or filling mode.
FIG. 6B is a schematic side cross-sectional view of the handpiece shown in FIG. 6A.

FIG. 6A is a schematic side view of a handpiece 3A having a cleaning mode and an obturation or filling mode. FIG. 6B is a schematic side cross-sectional view of the handpiece 3A shown in FIG. 6A. The handpiece 3A shown in FIGS. 6A-6B can advantageously be configured to clean a tooth when the handpiece 3A is in the cleaning mode and to obturate or fill the tooth when the handpiece is in the obturation mode. Unless otherwise noted, reference numerals used in FIGS. 6A-6B may correspond to components similar to or the same as similarly-numbered components in FIGS. 4A-5B. For example, the handpiece 3A of FIGS. 6A-6B includes a pressure wave generator 5 and a sealing cap 40 at a distal portion 19 of the handpiece 3A. The pressure wave generator 5 can comprise a fluid jet device including a nozzle (not shown), a guide tube 21, one or more openings 42 in the guide tube 21, and an impingement surface 33 at a distal end of the guide tube 21. A suction port 43 can fluidly communicate with a waste line 44 configured to convey waste fluids to a waste collection system. An interface member 4 can connect the handpiece 3A to one or more conduits coupled with the console 2. The console can include high pressure pumps for pressurizing the obturation material and a degassing apparatus for degassing the obturation material. Additional details of such a console may be found in U.S. patent application Ser. No. 14/172,809, filed on Feb. 4, 2014, entitled "DENTAL TREATMENT SYSTEM," which is incorporated by reference herein in its entirety and for all purposes.

The handpiece 3A can also include a high pressure supply line 26 extending from the console 2 to the interface member 4 and into the handpiece 3A. As explained with respect to FIGS. 4A-4B and 5A-5B, a pressurization system (e.g., high pressure pump) in the console 2 can pressurize suitable fluids, which are driven distally to the handpiece 3A and guide tube 21 by way of the supply line 26. As with the embodiment of FIGS. 4A-4B, the system can have a cleaning mode, in which the handpiece 3A is configured to clean the treatment region, and an obturation or filling mode, in which the handpiece is configured to deliver a flowable obturation or filling material to the treatment region. However, unlike the embodiment of FIGS. 4A-4B, in the embodiment of FIGS. 6A-6B, the modes can be switched upstream or proximal the handpiece 3A.

For example, the console 2 can include a switch (which may be similar to the switch 25 shown in FIG. 4B) that switches between the cleaning mode and the obturation mode. In various embodiments, the console 2 can include a controller (e.g., including a processor) and non-transitory memory that includes software instructions stored thereon that, when executed by the controller, switches between the cleaning and filling or obturation mode. When in the cleaning mode, cleaning fluids can be passed along the supply line 26 to the guide tube 21 to clean the treatment region of the tooth, as explained above with respect to FIGS. 4A-4B. When the clinician is finished cleaning the treatment region of the tooth, the clinician can switch to the obturation or filling mode, e.g., using the console 2. As shown in FIG. 6B, an obturation reservoir 27B or 27C can be disposed at any suitable portion of the fluid pathway. In some embodiments, for example, the obturation reservoir 27B can be disposed at or in the console 2. In other arrangements, the obturation reservoir 27C may be disposed along a conduit 34, or along any other portion of the fluid pathway, that extends between the handpiece 3A and the console 2.

When in the obturation or filling mode, flowable obturation material can flow from the reservoir 27B or 27C and through the supply line 26 to the guide tube 21. The flowable obturation material can flow outwardly to the treatment region through the opening(s) 42 to fill the treatment region. The obturation material can be driven distally in any suitable manner. For example, in some embodiments, fluid (such as air, water, etc.) can be pressurized and can dissolve, mix with, or otherwise interact with the obturation material. The pressurized fluid can carry the obturation material to the treatment region by way of the supply line 26. In other embodiments, the pressurized fluid can drive a plunger (such as the plunger 29 or piston shown in FIG. 5B) to drive the obturation material to the treatment region.

Accordingly, the obturation or filler reservoir, e.g., the component that contains the obturation or filler material, may be provided upstream of and/or proximal the handpiece 3A in some embodiments, and can be flowed downstream or distally by way of the pressurized fluid, whether directly or indirectly using a plunger. Furthermore, the handpiece 3A can be used in both cleaning procedures and obturation or restoration procedures, which can simplify treatment procedures and/or reduce costs.

FIG. 6C is a side cross-sectional view of a handpiece 3A configured to couple to a console 2 by way of an interface member 4 and a cartridge 601 configured to be disposed between the interface member 4 and the console 2. The handpiece 3A shown in FIGS. 6A-6B can advantageously be configured to clean a tooth when the handpiece 3A is in the cleaning mode and to obturate or fill the tooth when the handpiece is in the obturation or filling mode. Unless otherwise noted, reference numerals used in FIG. 6C may correspond to components similar to or the same as similarly-numbered components in FIGS. 6A-6B. The handpiece 3A of FIG. 6C includes a pressure wave generator 5 and a sealing cap 40 at a distal portion 19 of the handpiece 3A. The pressure wave generator 5 can comprise a fluid jet device including a nozzle (not shown), a guide tube 21, one or more openings 42 in the guide tube 21, and an impingement surface 33 at a distal end of the guide tube 21. A suction port 43 can fluidly communicate with a waste line 44 configured to convey waste fluids to a waste collection system. An interface member 4 can connect the handpiece 3A to one or more conduits 34 coupled with the console 2.

The handpiece 3A can also include a high pressure supply line 26 extending from the console 2 through the conduits 34 (which may comprise a hose) to the interface member 4 and into the handpiece 3A. As explained with respect to FIGS. 4A-4B and 5A-5B, a pressurization system (e.g., high pressure pump) in the console 2 can pressurize suitable fluids, which are driven distally to the handpiece 3A and guide tube 21 by way of the supply line 26. As with the embodiment of FIGS. 4A-4B, the system can have a cleaning mode, in which the handpiece 3A is configured to clean the treatment region, and an obturation or filling mode, in which the handpiece is configured to deliver a flowable obturation or filling material to the treatment region.

A reservoir 27G can also be provided to store and/or supply filling or obturation material to the handpiece 3A and treatment region. However, in the embodiment illustrated in FIG. 6C, the reservoir 27G can be disposed in or on a cartridge 601 that is disposed proximal the handpiece 3A. As shown in FIG. 6C, the cartridge 601 can connect to a distal portion of the interface member 4, which couples with the console 2 by way of conduit 34 (e.g., a high-pressure hose). Similarly, the handpiece 3A can connect to a distal portion of the cartridge 601. Thus, in some embodiments, the cartridge 601, which can include or be coupled with the reservoir 27G of filling or obturation material, can be disposed between the handpiece 3A and the interface member 4.

In some embodiments, the cartridge 601 can be removably engaged with the interface member 4. For example, prior to a cleaning procedure, the clinician can connect the handpiece 3A to the interface member 4 (e.g., using a suitable connecting mechanism) to enable fluid communication between the console 2 and the handpiece 3A. The clinician can activate the cleaning procedure (e.g., at the console 2), and cleaning fluids can pass through the supply line 26 from the console 2, through the conduit 34 and interface member 4, and into the handpiece 3. The cleaning fluids can clean the treatment region of the tooth as explained herein.

After cleaning, the clinician can begin a filling or obturation procedure by inserting the cartridge 601 between the handpiece 3A and interface member 4. For example, after removing the handpiece 3A from the interface member 4, the clinician can connect the cartridge 601 to the interface member 4, and can connect the handpiece 3A to the distal portion of the cartridge 601. Thus, in various arrangements, the handpiece 3A and cartridge 601 can have the same connecting configuration. For example, the proximal portion of the handpiece 3A can include connectors similar to those on the proximal portion of the cartridge 601, such that both the cartridge 601 and the handpiece 3A can connect to the interface member 4. Further, the distal portion of the interface member 4 and the distal portion of the cartridge 601 can include similar connectors such that the handpiece 3A can connect to the cartridge 601. In some embodiments, the same handpiece 3A can be used to both clean and fill the treatment region. In other embodiments, different handpieces 3A can be used to clean and fill the tooth.

In other embodiments, the cartridge 601 may be secured or fixed relative to the interface member 4 such that the cartridge 601 remains coupled with the interface member 4. In such arrangements, the clinician can connect the handpiece 3A to the cartridge 601 (which is already connected to the interface member 4), and can conduct a cleaning procedure. After cleaning, the clinician can activate a switch on the cartridge 601 to switch from a cleaning mode to a filling or obturation mode. The switch on the cartridge 601 may be the same as or similar to the switch 25 shown in FIG. 4B. In such embodiments, the clinician may not remove the handpiece 3A between cleaning and filling the treatment region. Further, although the interface member 4 and cartridge 601 are shown as separate components, it should be appreciated that, in some embodiments, the cartridge 601 and interface member 4 can be combined into a single unit.

FIG. 6D is a schematic, cross-sectional magnified view of a cartridge 601 disposed proximal a handpiece 3A. The cartridge 601, handpiece 3A, conduit 34, and supply line 26 may be similar to or the same as similarly-numbered components described above with respect to FIGS. 4A-6C. Although the interface member 4 is not illustrated in FIG. 6D, as explained above with respect to FIG. 6C, the interface member 4 may also be disposed between the cartridge 601 and the conduit 34. In some embodiments, the cartridge 601 is removable from the conduit 34 and/or the interface member 4. In other embodiments, the cartridge 601 may be secured or fixed to the conduit 34 and/or interface member 4. In FIG. 6D, the cartridge 601 can couple to conduit 34 by way of a first connector 603. The first connector 603 may be the same as or similar to the interface member 4 described herein, or the first connector 603 may include different connections for coupling with the conduit 34. A second connector 602 can connect the cartridge 601 with the handpiece 3A. The connector 602 can be separate from the handpiece 3A and cartridge 601, or the connector 602 can be coupled to or formed with either the handpiece 3A or the cartridge 601.

As with FIG. 6C, the cartridge 601 can comprise a reservoir 27G for storing and/or supplying the obturation or filling material to the handpiece 3A and treatment region. For example, in some embodiments, the reservoir 27G can comprise a volume or container that stores the filling material. However, if a container or vessel that encloses a large, enclosed volume is used to store the filling material, then the container may be subject to high pressures. If a relatively large amount of filling material is pressurized (e.g., by way of the high pressure supply line 26) and stored in the container, then the resulting high pressures may damage the container or cause the container to fail or rupture. Thicker walls or improved container designs may be suitable, however, such solutions may increase the cost or complexity of the cartridge 601 and reservoir 27G.

Accordingly, in some embodiments, the cartridge 601 can comprise a reservoir 27G in which the supply line 26 is coiled within or on the cartridge 601 or other type of storage or supply device. As shown in FIG. 6D, the high pressure supply line 26 can pass from the console 2, through the conduit 34, and into the cartridge 601. The portion of the supply line 26 passing in the conduit 34 may be uncoiled. However, the supply line 26 can be formed into a coiled portion 626 at the cartridge 601. Thus, at the cartridge 601 (e.g., within the cartridge 601), the supply line 26 can be deformed to form multiple coils. The use of multiple coils at the cartridge 601 can enable the storing or supply of a relatively high volume of filling material, as compared with an uncoiled supply line. For example, coiling the supply line 26 can effectively increase the length of supply line within the cartridge 601, enabling the coiled portion 626 of the supply line 26 to store or supply a higher volume of filling material. Furthermore, the high pressure imparted on the supply line 26 is distributed across the relatively large internal surface area provided by the coiled portion 626, which can reduce the load on the supply line 26 and reduce or prevent damage or failure to the cartridge 601 or supply line 26. The supply line 26 may be straightened or uncoiled distal the cartridge 601 when the supply line 26 passes through the handpiece 3A.

It should be appreciated that the cartridge 601 and/or reservoir 27G shown in FIG. 6D with the coiled portion 626 of the supply line 26 may be used in any of the embodiments disclosed herein. For example, the reservoir 27 of FIG. 4B may similarly comprise a coiled portion of the supply line 26. Similarly, reservoirs 27B and 27C of FIG. 6B may also comprise a coiled portion of the supply line 26.

FIG. 7A is a schematic side view of a handpiece 3A having a removable obturation reservoir 27D. FIG. 7B is a schematic side cross-sectional view of the handpiece 3A shown in FIG. 7A. The handpiece 3A shown in FIGS. 7A-7B can advantageously be configured to be reused in multiple obturation treatments. Unless otherwise noted, reference numerals used in FIGS. 7A-7B may correspond to components similar to or the same as similarly-numbered components in FIGS. 4A-6D. For example, the handpiece 3A of FIGS. 7A-7B includes a pressure wave generator 5 and a sealing cap 40 at a distal portion 19 of the handpiece 3A. The pressure wave generator 5 can comprise a fluid jet device including a nozzle (not shown), a guide tube 21, one or more openings 42 in the guide tube 21, and an impingement surface 33 at a distal end of the guide tube 21. A suction port 43 can fluidly communicate with a waste line 44 configured to convey waste fluids to a waste collection system. An interface member 4 can connect the handpiece 3A to one or more conduits coupled with the console 2.

The handpiece 3A can also include a high pressure supply line 26 extending from the console 2 to the interface member 4 and into the handpiece 3A. As explained with respect to FIGS. 4A-6B, a pressurization system (e.g., high pressure pump) in the console 2 can pressurize suitable fluids, which are driven distally to the handpiece 3A and guide tube 21 by way of the supply line 26. Unlike the embodiments of FIGS. 4A-6B, however, the handpiece 3A can include a compartment 31 sized and shaped to receive a removable obturation reservoir 27D. For example, the obturation reservoir 27D may be provided separately from the handpiece 3A. The clinician can insert the reservoir 27D into the compartment 31 prior to an obturation or filling procedure. One or more connectors 35 can be provided in the handpiece 3A to secure the reservoir 27D to the compartment 31 and to provide fluid communication between the reservoir 27D and the supply line 26.

During an obturation or filling procedure, as explained above, the clinician can activate the handpiece 3A (e.g., using the console 2) to drive a pressurized fluid along the supply line 26 to the reservoir 27D. In the embodiment of FIGS. 7A-7B, the pressurized fluid can press against a plunger 29 or piston, which can drive the obturation or filling material along the supply line 26 to the guide tube 21 and the treatment region. In other arrangements, as explained above, the pressurized fluid can directly drive the obturation material and/or can mix or dissolve the obturation material to cause the obturation material to be flowable. Once the filling procedure is complete the clinician can remove the obturation reservoir 27D from the handpiece 3A and can reuse the handpiece 3A in a subsequent procedure.

The handpiece 3A illustrated in FIGS. 7A-7B does not show a switch that changes the handpiece to a cleaning mode. However, it should be appreciated that the reservoir 27 shown in the multi-mode handpiece 3A of FIG. 4B can instead be configured to be removable, similar to the embodiment shown in FIG. 7B. Thus, in some embodiments, a multi-mode handpiece 3A may be reused for both cleaning and obturation procedures, provided that adequate cleaning and/or sanitation safeguards are maintained. The pressurized fluid that drives the piston or plunger 29 can be pressurized using the pressurization system described above with respect to U.S. application Ser. No. 14/172,809 and U.S. Patent Publication No. US 2012/0237893, each of which is incorporated by reference herein. It should further be appreciated that the reservoir 27D shown in FIG. 7B can include a coiled portion 626 of the supply line 26, as shown and described with relation to FIG. 6D.

FIG. 8A is a schematic side cross-sectional view of a handpiece 3A configured to deliver a first composition (e.g., a gelifying material) and a second composition (e.g., a gelifying initiator) to a treatment region of a tooth to obturate or fill the treatment region of the tooth, according to one embodiment. Unless otherwise noted, reference numerals used in FIG. 8A may correspond to components similar to or the same as similarly-numbered components in FIGS. 4A-7B. For example, the handpiece 3A of FIG. 8A includes a sealing cap 40 at a distal portion 19 of the handpiece 3A and a suction port 23 in fluid communication with a waste line 44 configured to convey waste fluids to a waste collection system. An interface member 4 can connect the handpiece 3A to one or more conduits coupled with the console 2.

Figure 8C:
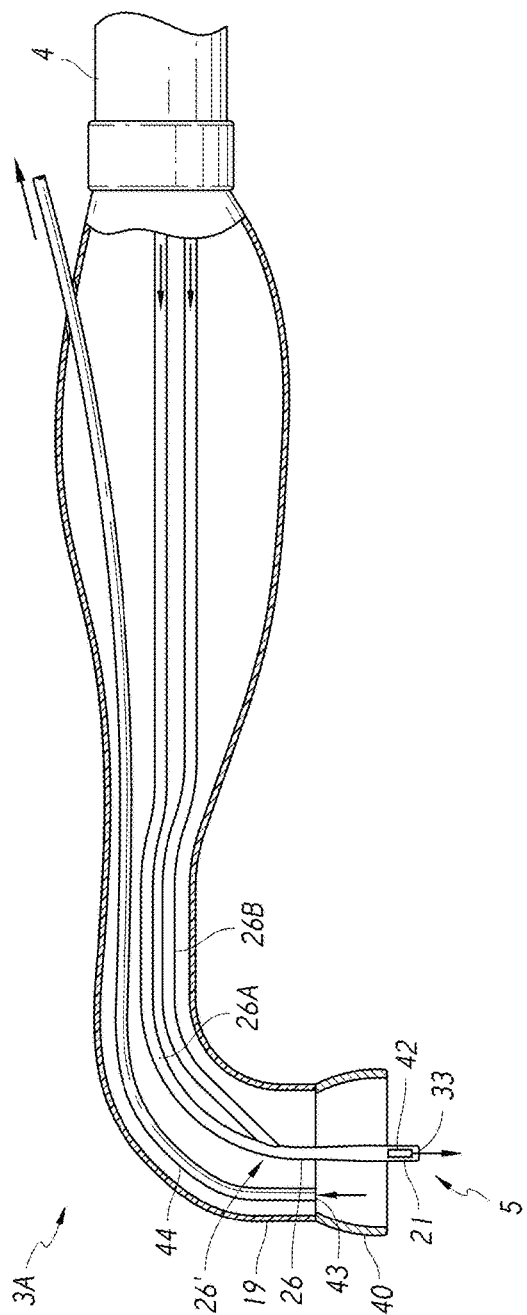
FIG. 8C is a schematic side cross-sectional view of a handpiece configured to deliver multiple components of an obturation material to the treatment region, according to one embodiment.

Unlike the embodiments of FIGS. 4A-7B, however, the embodiment of FIG. 8A includes a first high pressure fluid supply line 26A and a second high pressure fluid supply line 26B extending from the console 2 to the distal portion 29 of the handpiece 3A. The first and second supply lines 26A, 26B can be configured to deliver two materials that, when mixed in the tooth or just prior to entering the tooth, form a gel that is suitable for filling the treatment region of the tooth. For example, a gelifying initiator can be conveyed along the first supply line 26A to the distal portion 19 of the handpiece 3, and a gelifying obturation material can be delivered along the second supply line 26B to the distal portion 19 of the handpiece 3A. The gelifying initiator and obturation material can be stored in reservoirs located at the console 2 (or anywhere along the pathway between the console 2 and the handpiece 3A, and suitable pressurization systems (such as the pumps disclosed herein) can drive the initiator and obturation material to the handpiece 3A. In some embodiments, the reservoirs can comprise a coiled portion of the supply lines 26A, 26B. Although gelifying initiators and materials are disclosed with respect to FIGS. 8A-8D, it should be appreciated that any suitable combination of compositions may be used, including materials configured to be cured, hardened, etc.

The gelifying material can comprise any suitable obturation material that turns into a gel when it interacts with a gelifying initiator. For example, as explained herein, a sodium Alginate solution can gelify upon exposure to calcium or calcium containing compounds (e.g., $CaCl_2$). In such an arrangement, the sodium Alginate may act as the gelifying material, and the calcium-containing material may act as the gelifying initiator. It should be appreciated that sodium Alginate and calcium-containing materials are just a few illustrative examples. Any other suitable gelifying materials and initiators may be used in the embodiments disclosed herein, including additional gel arrangements disclosed herein. Furthermore, although the materials are described as gelifying initiators and materials, it should be appreciated that any other combination of materials can be mixed at the treatment region of the tooth. In addition, although two supply lines are illustrated for mixing two materials in FIG. 8A, it should be appreciated that additional supply lines may be provided to mix or cause more than two materials (e.g., three, four, five, or more) to interact at the treatment region. Furthermore, it should be appreciated that any suitable combination of materials other than gelifying materials may be used in the embodiments of FIGS. 8A-8D.

The gel initiator can be conveyed into the treatment region of the tooth by way of a first inlet 21A in fluid communication with the first supply line 26A. The gelifying obturation material can be conveyed into the treatment region of the tooth by way of a second inlet 21B in fluid communication with the second supply line 26B. The gelifying initiator can interact with the gelifying obturation material at the treatment region (e.g., within the tooth chamber or near a carious region of the tooth), and the resulting obturation gel can fill the treatment region (e.g., a root canal or a cleaned carious region), including small spaces and cracks in the tooth. Although a pressure wave generator is not illustrated in FIG. 8A, it should be appreciated that any suitable pressure wave generator 5 (such as a fluid jet) can also be used to assist in filling the treatment region. Thus, in FIG. 8A, the components of the obturation material can be supplied to the tooth by inlets 21A, 21B, and the pressure wave generator can be activated to enhance the filling. Although the embodiment of FIG. 8A has been disclosed with reference to a gelifying base material and a gelifying initiator, it should be appreciated that the handpiece 3A of FIG. 8A can be used with any suitable combination of components for an obturation material.

FIG. 8B is a schematic side cross-sectional view of a handpiece 3A configured to deliver a first composition (e.g., a gelifying material) and a second composition (e.g., a gelifying initiator) to fill a treatment region of a tooth, according to another embodiment. Unless otherwise noted, reference numerals used in FIG. 8B may correspond to components similar to or the same as similarly-numbered components in FIG. 8A. For example, the handpiece 3A of FIG. 8B includes a sealing cap 40 at a distal portion 19 of the handpiece 3A and a suction port 43 in fluid communication with a waste line 44 configured to convey waste fluids to a waste collection system. An interface member 4 can connect the handpiece 3A to one or more conduits coupled with the console 2.

The handpiece 3A can also include a first supply line 26A that conveys a gelifying initiator and a second supply line 26B that conveys a gelifying obturation material. A first inlet 21A can supply the gelifying initiator to the treatment region and a second inlet 21A can supply the gelifying obturation material to the treatment region. The gelifying initiator can interact with the base gelifying obturation material to form a gel sufficient to fill the treatment region of the tooth, including small spaces and cracks of the tooth. However, unlike the embodiment of FIG. 8A, the handpiece 3A shown in FIG. 8B can include a gelifying initiator reservoir 27E and a gelifying obturation material reservoir 27F that are loaded on or coupled with the handpiece 3A. Plungers 29 can be driven by pressurized fluid to drive the gelifying initiator from the reservoir 27E and the gelifying obturation material from the reservoir 27F. The reservoirs 27E, 27F may be permanently formed with or coupled to the handpiece 3A in some arrangements. In other arrangements, the reservoirs 27E, 27F may be removably coupled with the handpiece 3, similar to the arrangement described above with respect to FIGS. 7A-7B. In some embodiments, a pressure wave generator can be activated during or after the supply lines 26A, 26B deliver the materials to the tooth to enhance filling. Although the embodiment of FIG. 8B has been disclosed with reference to a gelifying base material and a gelifying initiator, it should be appreciated that the handpiece 3A of FIG. 8B can be used with any suitable combination of components for an obturation material. Further, although the reservoirs 27E, 27F are illustrated as including plungers 29, it should be appreciated that any suitable reservoir can be used, including a reservoir that comprises a coiled portion of the supply lines 26A, 26B.

FIG. 8C is a schematic side cross-sectional view of a handpiece 3A configured to deliver multiple components of an obturation material to the treatment region. Unless otherwise noted, reference numerals used in FIG. 8C may correspond to components similar to or the same as similarly-numbered components in FIGS. 8A-8B. For example, the handpiece 3A of FIG. 8C includes a sealing cap 40 at a distal portion 19 of the handpiece 3A and a suction port 43 in fluid communication with a waste line 44 configured to convey waste fluids to a waste collection system. An interface member 4 can connect the handpiece 3A to one or more conduits coupled with the console 2.

The handpiece 3A can also include a first supply line 26A that conveys a gelifying initiator and a second supply line 26B that conveys a gelifying obturation material. The first and second supply lines 26A, 26B can extend from the console 2 to the handpiece 3A, as explained above with respect to FIG. 8A. A reservoir may store the filling material and can be disposed in the console 2, in the handpiece 3A, or between the handpiece 3A and console 2. In some embodiments, the reservoir can comprise a coiled portion of the supply lines 26A, 26B, as described above with respect to FIG. 6D. Unlike the embodiment of FIGS. 8A-8B, however, the first and second supply lines 26A, 26B can join at a junction 26'. The respective materials that pass through the supply lines 26A, 26B can be mixed at the junction 26' and can pass along a common supply line 26 to a guide tube 21 of a pressure wave generator 5. The gelifying initiator can interact with the base gelifying obturation material to form a gel sufficient to fill the treatment region of the tooth, including small spaces and cracks of the tooth. The mixed material can pass along the guide tube 21 and can form a jet after passing through an orifice. The jet of obturation material can enter the treatment region through the openings 42. An impingement surface 33 can deflect the jet to prevent damage to the anatomy.

As shown in FIG. 8C, the pressure wave generator 5 can therefore deliver a combination of materials to the treatment region. Because the two components (e.g., the gelifying initiator and the base material) are mixed in the handpiece 3A just prior to entering the treatment region, the hardening or gelification process may not have been completed, and the obturation material may be sufficiently flowable to fill the treatment region. As explained herein, the pressure wave generator 5 can be activated to substantially fill the treatment region, including small spaces of the tooth. Further, although the embodiment of FIG. 8C has been disclosed with reference to a gelifying base material and a gelifying initiator, it should be appreciated that the handpiece 3A of FIG. 8C can be used with any suitable combination of components for an obturation material.

Figure 8D:
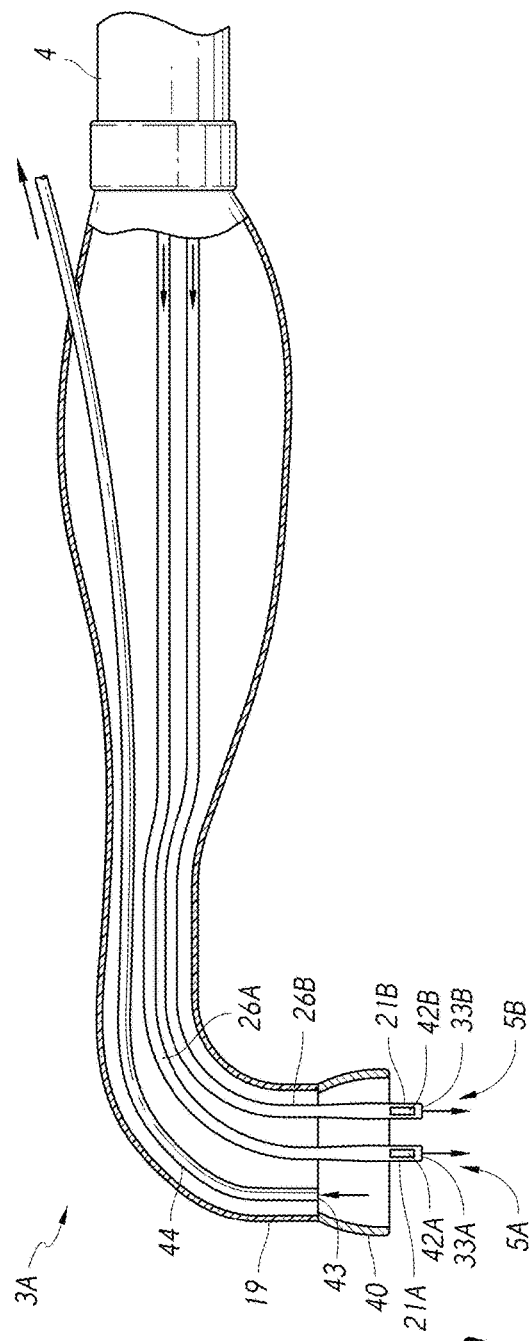
FIG. 8D is a schematic side cross-sectional view of a handpiece configured to deliver multiple components of an obturation material to the treatment region, according to another embodiment.

FIG. 8D is a schematic side cross-sectional view of a handpiece 3A configured to deliver multiple components of an obturation material to the treatment region. Unless otherwise noted, reference numerals used in FIG. 8D may correspond to components similar to or the same as similarly-numbered components in FIGS. 8A-8C. For example, the handpiece 3A of FIG. 8D includes a sealing cap 40 at a distal portion 19 of the handpiece 3A and a suction port 43 in fluid communication with a waste line 44 configured to convey waste fluids to a waste collection system. An interface member 4 can connect the handpiece 3A to one or more conduits coupled with the console 2. A reservoir may store the filling material and can be disposed in the console 2, in the handpiece 3A, or between the handpiece 3A and console 2.

The handpiece 3A can also include a first supply line 26A that conveys a gelifying initiator and a second supply line 26B that conveys a gelifying obturation material. The first and second supply lines 26A, 26B can extend from the console 2 to the handpiece 3A, as explained above with respect to FIG. 8A. As shown in FIG. 8D, a first pressure wave generator 5A and a second pressure wave generator 5B can be disposed near the distal portion 19 of the handpiece 3A. The first pressure wave generator 5A can comprise a first guide tube 21A in fluid communication with the first supply line 26A, and the second pressure wave generator 5B can comprise a second guide tube 21B in fluid communication with the second supply line 26B. Components of the obturation material can pass along the supply lines 26A, 26B to the respective guide tubes 21A, 21B. Upon passing through an orifice (not shown), two jets can be formed that are conveyed along the guide tubes 21A, 21B. The components of the obturation material (e.g., the gelifying initiator and the gelifying obturation material) can enter the treatment region by way of first and second openings 42A, 42B, respectively. Impingement surfaces 33A, 33B can prevent the jet from impacting the anatomy directly. In the embodiment of FIG. 8D, the pressure wave generators 5A, 5B can generate pressure waves that cause the two component materials to mix at the treatment region and to substantially fill the treatment region. Further, although the embodiment of FIG. 8D has been disclosed with reference to a gelifying base material and a gelifying initiator, it should be appreciated that the handpiece 3A of FIG. 8D can be used with any suitable combination of components for an obturation material.

III. Examples of Filling Materials and Methods

Various embodiments disclosed herein may be used to obturate a root canal of a tooth after cleaning, and/or to fill a portion of a treatment region after cleaning, e.g., a treated carious region. As explained herein, various methods can be used to clean a treatment region of a tooth. For example, in some embodiments, a pressure wave generator 5 can be used to clean diseased materials, bacteria, and other undesirable materials from the root canal of the tooth. In other embodiments, the pressure wave generator 5 can clean a carious region from an outer surface of the tooth. When the treatment region (e.g., root canal, carious region, etc.) is substantially clean, the clinician can obturate or fill the treatment region with a suitable obturation material. For example, in a root canal treatment, the clinician may fill the canals with the obturation material in order to prevent bacteria or other undesirable materials from growing (or otherwise forming) in the canal spaces after treatment. Accordingly, to protect the long-term health of the tooth, it can be advantageous to substantially fill the canal spaces of the tooth, including the major canal spaces as well as minor cracks and spaces in the tooth. The filling or obturation material can be cured or hardened to form the final material. Indeed, it should be appreciated that setting, curing, hardening, etc. may all refer to processes by which initial components are transformed into the final material. It should be appreciated that each of the obturation materials (and also the handpieces) disclosed herein may be used in conjunction with filling root canals after root canal treatments and/or with filling treated carious regions after treatment. Thus, the use of the term "obturation material" should be understood to mean a material that is configured to fill root canals and/or treated carious regions of the tooth. Similarly, as used herein, obturating or filling a treatment region should be understood to mean a procedure in which a treatment region is filled or restored, e.g., filling a root canal or a treated carious region of a tooth.

In some embodiments, a pressure wave generator 5 is used to assist in obturating the treatment region. For example, in some embodiments, the obturation material can be delivered using a needle and pressure driven mechanism, such as a syringe. In such arrangements, the pressure wave generator 5 can be provided separate from the syringe, and can be activated to assist in causing the obturation material to flow into small spaces and cracks of the treatment region. In other embodiments, the clinician can use another type of mechanical device or the clinician's hand to place the material inside the tooth chamber, and the pressure wave generator 5 can be activated to help cause the obturation material to fill the treatment region. In still other embodiments, a suction-based delivery system can apply a negative pressure to the root canal space, causing the obturation material to be drawn into the root canal spaces. The pressure wave generator 5 can be activated to assist in filling the treatment region. In yet other embodiments, the pressure wave generator 5 can deliver one component of the filler material at a high pressure, and another device (such as a syringe or other mechanical delivery device) can deliver a second component of the filler material at any suitable pressure.

In some arrangements, as explained herein, the pressure wave generator 5 can act as the delivery device to supply the obturation material to the treatment region and to cause the obturation material to substantially fill the treatment area, e.g., the canal spaces of a root canal. For example, in some embodiments, the pressure wave generator can comprise a liquid jet device. The obturation material (which may include one, two, or more compositions) may be flowed through a handpiece (see FIGS. 4A-8D) under pressure. A liquid jet device at a distal portion of the handpiece can include a jet-forming nozzle or orifice and a guide tube along which the jet propagates. The obturation material(s) may form a liquid jet upon passing through the liquid jet device. For a particular type of obturation material, the driving pressure and orifice/nozzle diameter can be selected such that the obturation or filling material forms a fluid jet. One or more openings in the guide tube can allow the obturation material(s) to flow into the treatment region (e.g., root canal) to supply the obturation material(s) to the treatment region. The jet of obturation material can pass through fluid in the treatment region (e.g., other flowable obturation material, other treatment fluids, etc.), which may generate pressure waves in the fluid. As explained herein, the generated pressure waves can assist in propagating the obturation material throughout the treatment region, including, e.g., small spaces and cracks in the tooth.

In addition, the handpiece 3 can be used to deliver multiple materials, or a mixture of multiple materials, to the treatment region (e.g., root canal). For example, in some embodiments, multiple materials can be mixed at the handpiece or upstream of the handpiece. The resulting mixture can be supplied to the treatment region by the handpiece (e.g., by the pressure wave generator). In other arrangements, multiple materials can be delivered to the treatment region and can be mixed at the treatment region, such as within the tooth.

As explained above, the pressure wave generator can be activated to assist in causing obturation material to flow throughout the treatment region, including into small spaces, cracks, and tubules of the tooth. Moreover, in some arrangements, the pressure wave generator 5 can be activated to assist in curing or hardening the obturation material. For example, in some arrangements, mechanical agitation by the pressure waves can assist in hardening the obturation material. In other arrangements, agitation by the pressure waves can break apart an encapsulating material that covers a particular type of material (such as ionic particles or compounds, or a polymerization initiator), which, when released, can react with another material (such as a monomer, oligomer, polymer, etc.). The energy delivered by the pressure wave generator can be controlled to control the rate of hardening of the obturation material in the tooth or treatment region. Thus, the use of a pressure wave generator 5 can assist in ensuring that the entire treatment region is filled with obturation material, and can also assist in the hardening of the obturation material.

It should be appreciated that the filling material and procedural parameters for the pressure wave generator 5 may be selected such that the filling material is flowable as it fills the canal or treatment region, and then once it fills the canals or treatment region, it can be hardened. For multiple component mixtures, for example, the reaction rate between the components, the mixing rate of the components, and the fill rate of the filling material can at least in part determine whether the obturation is effective. For example, if the fill rate is less than the reaction rate, then the composition may harden before filling the treatment region. If the fill rate is faster than the mixing rate of the two components, then an inhomogeneous mixture may result in the canals or treatment region. Accordingly, it can be important so select combinations of compositions such that the material is able to flow fully into the treatment region before it hardens and such that the compositions mix well before it fills the treatment region and hardens. In addition, for single component materials, the material and curing method can be selected such that the filling material does not harden before it fills the treatment region.

A. Non-Limiting Examples of Obturation Materials

Various types of obturation or filling materials may be suitable with the embodiments disclosed herein. In some embodiments, the obturation or filling material can comprise two or more components that react with one another to form a hardened obturation material. In other embodiments, the obturation or filling material can comprise a composition that is curable from a flowable state to a hardened state by way of an external trigger (e.g., light, heat, etc.). Still other types of obturation materials may be hardened by precipitation, by the addition of moisture, by drying or evaporation, or by combination with a catalyst or initiator.

1. Multi-Component Obturation Materials

Various obturation materials used with the embodiments disclosed herein may include two components that are mixed prior to entering the tooth, or that are mixed inside the tooth or at the treatment region. The components may comprise one or more chemical compounds. For example, a first, flowable carrier component, X, may act as a flowable carrier material and may act to flow through the treatment region to fill the treatment region (e.g., the root canal system). A second filler component, Y, may comprise a material that is a solid, a semisolid, a powder, a paste, a granular material, a liquid-containing granular material, a solution containing particles (such as nanoparticles), a liquid containing gas, a gas, or any other physical form. In various arrangements, the first flowable component X may have physical properties (such as viscosity) closer to water than the second component Y. In some embodiments, the second flowable component X is configured to be delivered by way of the pressure wave generator 5 of the handpiece 3, e.g., by way of a high pressure fluid supply line in the handpiece 3. The second filler component Y may be delivered via a separate high-pressure line, or by a low pressure line, in the handpiece 3. For example, the second filler component Y may be delivered with active pressure or may be driven via suction, for example, by way of the suction created by the jet in a jet apparatus. The second filler component Y may be delivered by a separate pump or delivery mechanism that may or may not be synchronized with and/or coupled to the handpiece 3. In some embodiments, the second filler component Y may comprise a material that is placed into the treatment region by hand, needle, or any other delivery mechanism before, during, or after the introduction of the first flowable component X.

The filler component Y may be mixed with the flowable component X in the console 2, somewhere along the high pressure flow path between the handpiece 3 and the console 2, in the handpiece 3 (e.g., in a reservoir or cartridge within the handpiece 3), or at the treatment region (e.g., in the tooth chamber or root canals). The flowable component X may dissolve or carry filler material Y with itself into the treatment region of the tooth. The filler component Y may be applied directly into the tooth, and flowable component X may be supplied and flowed through the treatment region with the pressure wave generator 5. In some embodiments, the hydroacoustic and hydrodynamic effects created by the pressure wave generator 5 may dissolve or activate filler material Y. Other triggers may also be used, e.g., light, heat, etc. The flowable component X may be sufficiently degassed such that the resulting mixture of flowable component X and filler component Y is also adequately degassed.

The physical properties of the obturation material may be controlled such that the obturation material can be delivered into the treatment region of the tooth by way of the pressure wave generator 5 to provide adequate filling and sealing before the properties of the obturation material changes and/or before the obturation material sets or is cured. The setting/curing time may be controlled such that adequate mixing is obtained and adequate filling and sealing is obtained before the obturation material sets. In one embodiment, the entire filling process is completed in about 5 seconds or less. In other embodiments it may take up to about 30 s, 60 s, or 5 minutes for proper and adequate filling and sealing to occur.

The second fillable component Y may be provided inside a cartridge or reservoir that is disposed in or near the handpiece 3. As explained above, the cartridge can be provided at the handpiece 3 or upstream from the handpiece 3. The cartridge or reservoir may contain the filler component Y, which may or may not be degassed. In embodiments in which the cartridge is upstream of the handpiece 3, the cartridge may provide features that allow for sufficient mixing with adequate uniformity of components X and Y before entering the handpiece. In embodiments in which the reservoir or cartridge is disposed in the handpiece 3, the components X and Y can be suitably mixed in the handpiece 3 just prior to being supplied to the treatment region of the tooth. In still other arrangements, the components X and Y are maintained separate from one another in the handpiece 3 and are mixed together at or near the treatment region of the tooth. In various embodiments, the cartridge or reservoir may be disposable. The handpiece can also be disposable.

2. Other Examples of Multi-Component Obturation Materials

In some embodiments, the filling or obturation material may be hardened by utilizing a multi-component (e.g., two component) chemically curable system. Hardening of such systems may comprise mixing of stoichiometric or approximately stoichiometric relative amounts of initially separate components, herein termed component A and component B, which can then undergo chemical reactions to form a hardened material. In some arrangements, the mixing of components may be done by volume or other suitable measure. Mixing may occur immediately prior to delivering the material into the root canal system (or other treatment region), or mixing may occur within the root canal system or treatment region after simultaneous, consecutive, or alternating delivery of both parts into the tooth through diffusion. For example, in some embodiments, component A and component B can be mixed in the handpiece 3 or along the fluid pathway between the handpiece 3 and console 2. The components A and B can therefore be delivered as a mixture to the tooth. In other embodiments, component A and component B can be delivered to the tooth along separate fluid pathways and can be mixed in the tooth. In some embodiments, component A and B can be introduced to the treatment region concurrently. In other embodiments, component A can be introduced to the treatment region, then component B can be introduced to the treatment region. In still other embodiments, component A can be delivered to the tooth, then component B can be delivered to the tooth, then component A can be delivered to the tooth, component B can be delivered to the tooth, and so on, until the treatment region is filled. Any suitable order or permutation of material delivery may be suitable. Mixing may also be assisted by agitation provided by the pressure wave generators disclosed herein.

In some embodiments, the hardening reaction may comprise the addition of suitably reactive functional groups of the first component A to strained cyclic functional groups present in the second component B. Examples include, without limitation, reactions between oxirane or oxetane groups and nucleophilic functional groups, including the known epoxy-amine and epoxy-thiol systems. In one embodiment, component A may comprise diepoxy functionalized prepolymers. The prepolymers can advantageously be hydrophilic, which may facilitate penetration of the uncured liquid deep into small spaces within the root canal system, such as side canals and dentinal tubules. However, hydrophobic prepolymers may also be suitable. The prepolymers may include without limitation poly(alkylene glycol) diglycidyl ether, and may further comprise poly(glycidyl ether) crosslinking prepolymers including without limitation trimethylolpropane tri(glycidyl ether), ethoxylated trimethylolpropane tri(glycidyl ether), pentaerythritol tetra(glycidyl ether), ethoxylated pentaerythritol tetra(glycidyl ether), and the like. Component B may comprise hydrophobic and, advantageously, hydrophilic polyamine compounds including without limitation poly(alkylene oxide) diamines such as poly(ethylene glycol) di(3-aminopropyl ether). The obturation material may further contain radio contrast agents in the form of fine powders dispersed in part A or part B, or both. Suitable radio contrast agents include without limitation barium sulfate, bismuth oxychloride, bismuth carbonate, calcium tungstate, zirconium dioxide, ytterbium fluoride, and other suitable agents.

In another embodiment, the hardening reaction may comprise ionic crosslinking of anionically functionalized polysaccharides with multivalent cations. Component A may comprise a solution of an anionic polysaccharide and component B may comprise a solution of salts and polyvalent metal cations. The solvents in components A and B may be identical or they may be mutually miscible. One example solvent for components A and B may be water; however, other solvents may also be suitable. In one embodiment, the anionic polysaccharide may be selected from alginic acid and its salts with monovalent cations. One non-limiting example is sodium alginate, as explained in more detail below. The multivalent cation may be selected from earth alkaline metal salts or other cations that form stable chelates with the anionic polysaccharide. In one embodiment, the multivalent cation can be divalent calcium. Multivalent cations of metals with high atomic numbers may be added to impart radiopacity. Non-limiting examples of high atomic number cations include divalent strontium and barium salts.

In yet another embodiment, the hardening reaction may comprise a reaction between acid-dissolvable metal oxide solids and polyacids in the presence of water. Component A may comprise a metal oxide solid as a powder, dispersed in water, or other, water miscible, liquid. For the purposes of this disclosure, the term metal oxide is to be understood as broadly defined to include other basic acid-dissolvable inorganic salts, minerals, compounds, and glasses that may contain anions other than oxide anions such as phosphate, sulfate, fluoride, chloride, hydroxide, and others. Component B may comprise a solution of a polyacid in water or other, advantageously water miscible, liquid. An amount of water sufficient to at least partially support the setting reaction can be present in part A or part B, or both. The polyacid can undergo an acid-base reaction with the generally basic metal oxide, which may lead to the release of multivalent metal cations that form ionic crosslinks with the at least partially dissociated anionic polyacid to form a stable hardened matrix. Examples for suitable polyacids include without limitation polycarboxylic acids such as poly(acrylic acid), poly(itaconic acid), poly(maleic acid) and copolymers thereof, and may also be selected from polymers functionalized with other acidic functional groups such as sulfonic, sulfinic, phosphoric, phosphonic, phosphinic, boric, boronic acid groups, and combinations thereof. Examples of suitable basic metal oxides include without limitation zinc oxide, calcium oxide, hydroxyapatite, and reactive glasses such as aluminofluorosilicate glasses which may further contain calcium, strontium, barium, sodium, and other metal cations. In one embodiment, radio contrast agents as defined above may further be present in component A or component B, or both. In another embodiment, the material may further contain a hardenable resin composition that is curable by exposure to actinic radiation such as ultraviolet or visible light. The presence of a radiation curable resin may allow the practitioner to command cure at least part of the composition following the filling procedure to advantageously provide an immediate coronal seal. The radiation curable resin may be present in component A or component B, or both.

In yet another embodiment, the hardening reaction may comprise addition polymerization of silicone prepolymers that proceed with or without addition of catalysts. A non-limiting example of this reaction is a hydrosilylation addition to vinyl groups. Suitable silicone prepolymers may be selected from poly(diorgano siloxane) additionally substituted with reactive functional groups. Poly(diorgano siloxane) prepolymers of the general formula Z1-[R1R2SiO2]n-Z2 include without limitation poly(dialkyl siloxane) wherein R1 and R2 comprise identical or different alkyl radicals, poly(diaryl siloxane) wherein R1 and R2 comprise identical or different aryl radicals, and poly(alkyl aryl siloxane) wherein R1 and R2 comprise alkyl and aryl radicals. A suitable, non-limiting example for a poly(dialkyl siloxane) is poly(dimethyl siloxane); however other linear or branched alkyl substituents may be suitable. In one embodiment, component A may comprise vinyl functionalized silicone prepolymers including without limitation poly(diorgano siloxane) prepolymers carrying at least one vinyl group. Non-limiting examples are vinyl terminated poly(dimethyl siloxane) where Z1 and Z2 are vinyl groups, and copolymers of dialkyl siloxane and vinyl alkyl or vinyl aryl siloxane where R1 or R2 is a vinyl group in at least one repeat unit. Component B may comprise hydrosilane functionalized silicone prepolymers including without limitation vinyl hydride terminated poly(dimethyl siloxane) wherein Z1 and Z2 are hydrogen, and copolymers of dialkyl siloxane and hydro alkyl or hydro aryl siloxane wherein R1 or R2 is hydrogen in at least one repeat unit. Advantageously, the hydrosilane prepolymer can be functionalized with at least two, three or more hydrosilane groups. A polymerization catalyst may be added to either part A or part B. Examples of suitable catalysts include platinum catalysts such as hexachloroplatinic acid or Karstedt's catalyst (platinum(0)-1,3-divinyl-1,1,3,3-tetramethyldisiloxane complex).

Optionally, additives such as polymerization mediators and retarders may further be present in component A or component B, or both. Advantageously, the composition may further contain surfactants to facilitate penetration of the uncured liquid into small spaces within the root canal system. In some embodiments, radio contrast agents as defined above may further be present in component A or component B, or both. In one embodiment, component A and component B may be non-reactive in the absence of a suitable catalyst. In such an embodiment, components A and B may be combined prior to delivery. In some arrangements, components A and B may be stored in combined form for extended periods of time. The setting reaction may be induced by adding a suitable catalyst to the composition immediately prior to or following delivery of the composition into the root canal system, which advantageously obviates the mixing of the two components A and B in predefined ratios during delivery.

3. Gel-Based Obturation Materials

In various embodiments, the filling material used to fill the treatment region of a tooth (e.g., a tooth chamber, a root canal system, a treated carious region of a tooth) can include a gel-based material such as polymer molecules dissolved in water or hydrogel. In some arrangements, the polymer molecules can form a gel as soon as the molecules are in contact with water molecules. In various arrangements, other types of polymer molecules may form a gel following a trigger when the molecules are already in an aqueous solution. For example, the trigger can comprise heat, the addition of a composition having a predetermined pH, and/or chemical reactions between the polymer molecules and a different compound (such as a gelifying initiator). In some embodiments, the gel-based obturation materials may also comprise a multi-component obturation material, e.g., a polymer-ionic compound reaction, a polymer-polymer reaction, etc.

In some embodiments, the gelification (e.g., solidification) of a polymer solution (e.g., sodium alginate) in the presence of ionic compounds (e.g., calcium) may be used to obturate a root canal system. A liquid solution of polymers (e.g., sodium alginate) can be delivered into the treatment area, e.g. inside the tooth. Once the delivery of the solution (which may be three-dimensional and/or bubble-free) is complete, gelification can be achieved by, for example, providing ionic compounds to the solution. An ion-based (e.g., calcium-based) liquid may be delivered, or a calcium-based material (for example calcium hydroxide) may be applied, somewhere inside the tooth (or just prior to being delivered to the tooth) to contact the polymer. The calcium in this material can diffuse into solution and initiate the gelification of the material inside the tooth.

The gelification process can occur at different rates as a function of the availability of ions to the polymer compound. Gelification time scales can range from a fraction of a second to minutes, hours, etc. During an obturation or filling procedure, it can be important to precisely control the rate of gelification. For example, if gelification occurs too rapidly, then the obturation material may harden before it has fully filled the treatment region. Furthermore, rapid gelification may result in a non-homogenous mixture of materials, which may result in a poor obturation. On the other hand, if gelification occurs too slowly, then the obturation procedure may take too much time, creating discomfort for the patient and reducing efficiency of the treatment procedure. Accordingly, it can be desirable to control the rate of gelification such that the obturation procedure is relatively fast, while also ensuring that the obturation material is substantially homogenous and that the obturation material substantially fills the treatment region.

In some embodiments, a pressure wave generator can be used to help control the gelification process. For example, as explained above, the pressure wave generator can cause pressure waves to propagate through the obturation material, which can assist in causing the obturation material to flow through substantially the entire treatment region. For example, for root canal obturation procedures, the pressure wave generator can cause obturation material to flow through the major canal spaces, as well as the tiny cracks and spaces of the tooth. In addition, if the gelifying initiator (e.g., calcium particles or a calcium compound) is coated with an encapsulant, the pressure wave generator can be activated to break up the encapsulant to cause the release of the gelifying initiator. The pressure wave generator can be controlled to cause the release of the gelifying initiator at the desired rate. For example, if the gelification rate is to be increased, the energy supplied by the pressure wave generator may be increased to increase the rate at which the gelifying initiator is released. If the gelification rate is to be decreased, then the energy supplied by the pressure wave generator may be decreased to decrease the rate at which the gelifying initiator is released.

In other embodiments, another control mechanism may be the rate of ions released into the solution. For example, the ions can be supplied directly by means of concentrated solutions of triggering ions. If the concentrated solutions are supplied at a higher flow rate, then the gelification may occur at a faster rate. If the concentrated solutions are supplied at a lower flow rate, then the gelification may occur at a slower rate.

One example of a multi-composition obturation material may be formed by a trigger comprising an ionic reaction between two or more materials. In such arrangements, an obturation base material can be reacted or mixed with a gelifying initiator or agent. For example, sodium alginate (a flowable base material) may be in a liquid form when dissolved in water with a very low level of cations, but can gelify substantially instantaneously when in the presence of a gelifying initiator (e.g., calcium ions, potassium ions, etc.). When in a flowable state, the sodium alginate can be delivered into the treatment region of the tooth (e.g., the tooth chamber, root canal spaces, carious region, etc.) by way of the disclosed handpieces (FIG. 4A-8B), or by any other suitable delivery devices. The sodium alginate solution can gelify upon exposure to calcium or calcium containing compounds.

In some embodiments, the sodium alginate and calcium-containing compound can be delivered separately and can be mixed in the treatment region of the tooth. For example, in such embodiments, one outlet of the handpiece can deliver the sodium alginate to the tooth, and another outlet can deliver the calcium-containing compound to the tooth. The sodium alginate and calcium ions can react in the treatment region of the tooth. In other embodiments, the sodium alginate and calcium-containing compound can be mixed and reacted in the handpiece just prior to being delivered to the tooth. For example, the calcium-containing ions may be combined with the sodium alginate in a reservoir just prior to exiting the handpiece, such that the composition remains flowable. In yet other embodiments, coated calcium particles can be provided within the flowable sodium alginate solution. An encapsulant that coats the calcium particles can be broken or dissolved to release calcium when agitated, for example, by acoustic or shear forces that can be imparted on the particles by a pressure wave generator or other source. Although sodium alginate is one example of a base obturation material, any other suitable base material can be used, such as agar, collagen, hyaluronic acid, chondroitin sulfate, ulvan, chitosan, collagen/chitosan, chitin/hydroxyapatite, dextran-hydroxyethyl methacrylate, and/or pluronic. Furthermore, a radiopaque material may also be mixed with the obturation material to assist with radiographic visualization of obturation or filling for reimbursement (insurance) and assessment purposes.

In some embodiments, the ionic solution or gelifying initiator may be dispensed by way of a syringe and needle. In other embodiments, the ionic solution may be dispensed by a handpiece including a pressure wave generator, such as that disclosed herein. In one embodiment, the ionic solution or gelifying initiator may be dispensed by saturated cotton positioned in the pulp chamber of the tooth. As disclosed herein, in some arrangements, calcium compounds may be introduced into the polymer solution and trigger gelification. The solubility of the particular calcium compound may be used to control the time required for the gel to form. As an example, calcium chloride can initiate immediate gel formation due to its high water solubility, whereas the use of calcium sulfate or calcium carbonate can delay gel formation because of their lower solubility in water. In various embodiments, gelification may be achieved by ions that may be naturally provided by the surrounding dentin. Ions can diffuse from the dentin into the polymer solution (e.g., sodium alginate) and trigger gelification.

In some embodiments, ions (e.g., calcium) may be provided by common dental compounds such as dental sealers, calcium hydroxide or mineral trioxide aggregate (MTA). The dental compound may be applied anywhere in the proximity of the solution, for example, at the top of the canal and can initiate gelification by diffusion. Calcium rich compounds may also be introduced into the canals as points (e.g., calcium hydroxide points).

In some embodiments, the gelifying initiator (e.g., ions) may be encapsulated in nano/microspheres that are dispersed in the polymer solution. When subjected to high shear or oscillation, or any other chemical or physical phenomena, the encapsulating shell may be torn and ions can be released into the polymer solution within the root canal system or other treatment region. Such release can induce gelification of the polymer solution within the root canal. As explained above, in some arrangements, activation of the pressure wave generator can cause the encapsulating shell or encapsulant to break apart, which can control the gelification of the polymer solution. In some embodiments, ion-enriched microspheres or particles that are not subject to shear or that are shear resistant may be dispersed into solution within the root canal system. Once full obturation is achieved (e.g., assisted by the pressure wave generator in some embodiments), the particles or microspheres can slowly dissolve into solution, thereby initiating gelification. In some embodiments, light or heat can be applied to the encapsulated initiator to cause the release of the initiator.

In various embodiments, ions (e.g. calcium) may be introduced into solution by flowing the polymer solution (e.g. sodium alginate) through an ion (e.g. calcium) enriched capillary tube (e.g. guide tube or needle). By flowing through the tube, ions are introduced into solution and thereby can initiate gelification.

Further, when using sodium alginate as a base material for gel formation, various types of ions may be used. For example, cross-linking of the polymers can be achieved using divalent ions. Divalent ions that may be used as a gelifying initiator may include $Ca^{2+}$, $Ba^{2+}$, $Sr^{2+}$, $Mg^{2+}$, and/or $Fe^{2+}$. In some embodiments, barium ($Ba^{2+}$), may be used under its barium sulfate form as a gelifying agent or initiator. Advantageously, barium sulfate is also a radiopaque compound, such that barium sulfate may serve as a dual purpose compound, allowing for full gelification as well as radiopaque control of the proper extent of obturation.

In some embodiments, instead of using sodium alginate as a base obturation material, Kappa-Carrageenan can be used in conjunction with an initiator that includes potassium ions. In other embodiments, Iota-Carrageenan can be used in conjunction with an initiator that includes calcium ions. In some embodiments, the polymer base material may be a poly(carboxylate) polymer. For example, the polymer base material may include poly(acrylic acid), poly(methacrylic acid), copolymers of acrylic and itaconic acid, copolymers of acrylic and maleic acid, or combinations thereof. These polymers can be cross-linked through reaction with di- or trivalent cations, such as $Ca^{2+}$, $Zn^{2+}$, and/or $Al^{3+}$.

In various embodiments, crosslinking may be achieved through a glass-ionomer reaction, e.g., an acid-base reaction between a poly(carboxylic acid) and a reactive, ion-leachable glass in the presence of water. The reactive, ion-leachable glasses may comprise a fluoroaluminosilcate glass. The reactive fluoroaluminosilcate glass may further comprise calcium, barium, or strontium ions, and may further comprise phosphates and/or borates. In various embodiments, the polymer can be gelified via a reduction-oxidation reaction (redox) when in the presence of ions. It should be appreciated that, while the examples above discuss the use of hydrogels, the examples are non-limiting and the same concepts may apply to organogels.

In various embodiments disclosed herein, the gel can comprise a polymer matrix that traps fluid within its structure. For example, in the case of a hydrogel, this trapped fluid is water. The physical mechanical properties of the matrix may be controlled based on, for example, concentration of polymer or molecular properties (e.g. High M or High G grade in the case of sodium alginate). The matrix formed after gel formation (e.g. cross-linking) may exhibit various physical properties such as, for example, viscosity, strength, elasticity or even "mesh" size. The physical properties of the gel matrix may be tailored by way of the gel formation process. For example, in one embodiment, the physical properties of the obturation material may be controlled by generation of a gel using cross-linking. In various arrangements, the physical properties may be controlled by generation of a gel using thermally sensitive polymer molecules. In one embodiment, the physical properties may be controlled by generation of a gel using polymer molecules with free radicals, e.g., free radical polymerization.

In some embodiments, the physical properties of the obturation material may be controlled by combining more than one polymer (e.g. two polymers A & B). The molecules of polymer A may be linked to molecules of polymer B. For example, each polymer B molecule may be linked to polymer A molecules such that a matrix A-B-A-B . . . is formed. The link may be covalent or ionic in various embodiments. Click chemistry may be used to control this process in some arrangements. In some embodiments, polymer A may be selected from epoxy prepolymers, while polymer B may selected from amine prepolymers. The epoxy prepolymer can comprise at least two reactive epoxy (oxirane) functional groups and may be selected from bis(glycidyl ether) of bisphenol-type oligomers, bis(glycidyl ether) of poly (alkylene glycol) oligomers, triglycidyl ether of trimethylolpropane, triglycidyl ether of ethoxylated trimethylolpropoane, poly(glycidyl ether) of pentaerythritol, and the like. The amine prepolymer may comprise bis(aminoalkyl) poly(alkylene glycol), ethylenediamine, diethylenetriamine, triethylenetetramine, poly(ethylene imine), and the like. In other embodiments, polymer A may comprise a poly(isocyanate) and polymer B may comprise a polyol. In other embodiments, different types of polymers may be formed. For example, the compound may include copolymers that are randomly distributed. In some embodiments, block copolymers may be used. In various arrangements, polymerization and cross-linking can happen at the same time.

The polymer matrix may also be formed because of thermo-sensitivity of the molecule, in various arrangements. The physical mechanical properties of a gel (e.g. "mesh" size) may be adjusted to control the resistance of a gel to different chemical components, compounds or organisms. For example, the physical mechanical properties of a gel (e.g. "mesh" size) may be adjusted to trap organisms (e.g. bacteria) and prevent their proliferation after obturation. Trapping of bacteria may induce starvation or desiccation of the micro-organisms, which may induce death of the microorganism. In some embodiments, the physical mechanical properties of a gel (e.g. "mesh" size) may be adjusted by controlling the concentration of the gel. In some embodiment, the physical mechanical properties of a gel (e.g. "mesh" size) may be adjusted by controlling the molecular weight of the gel. In various embodiments, the physical mechanical properties of a gel (e.g. "mesh" size) may be adjusted by using different grades of polymers (e.g. different shapes) that induce different gelification patterns (e.g. different cross-linking pattern).

The obturation material may also comprise a gel that possesses various degradation properties that may be tailored to the application and expected life-time required of the obturation material. For example, in some cases, degradation of the obturation material may occur by surface erosion or bulk erosion. The rate of degradation may be controlled by adjusting the degree of oxidation of the polymer, by changing the purity of the polymer, and/or by adjusting the chain length or density of the polymer. In some embodiments, the degradation properties of the obturation material may be adjusted by changing the fluid used in the formation of the gel (e.g. fluid trapped in the structure).

In various embodiments, light may trigger, or assist in triggering, the gelification reactions described herein. For example, in some embodiments, photo-induced gelification may be used. Photo-induced gelification may be achieved using ultraviolet (UV) light or visible light in various arrangements, typically in the presence of a photoinitiator. In some embodiments, gels such as pluronic based hydrogels (e.g. DA Pluronic F-127) may be formed when exposed with UV and/or visible light. Such polymer solutions may be introduced in the root canal system or other suitable treatment regions. Once introduced into the root canals or treatment region, a UV and/or visible light source may be introduced on the coronal portion of the tooth or into the pulp chamber to initiate gelification. The UV and/or visible light source may be provided by a dental curing light. The source may also be located on the treatment handpiece 3 (e.g., near the proximal end of the guide tube) and may be activated after delivering the light-curable polymer solution.

In some embodiments, gels such as Dex-HEMA (Dextranhydroxyethyl methacrylate) based gels may be initiated by visible light. Light triggers can be achieved by delivering visible light to the coronal portion of the tooth or in the pulp chamber. The visible light source may be a regular light source or a visible dental curing light (e.g. blue). The visible light source may be located on the treatment handpiece 3 (e.g., near the proximal end of the guide tube) and activated after delivery of the polymer solution.

Additional examples of photo-inducible gels may include systems based on poly(alkylene glycol) diacrylate, poly (alkylene glycol) dimethacrylate, trimethylolpropane tri (meth)acrylate, ethoxylated trimethylolpropane tri(meth) acrylate, pentaerythritol poly(meth)acrylate, and the like, as well as combinations thereof, preferably in the presence of a photoinitiator.

Another gelification trigger that may be used in accordance with various embodiments is heat. Some hydrogels (e.g., agar) may gelify at known temperatures. Some of these materials may, however, exhibit a hysteresis behavior that may be useful in the obturation process. Such a thermally-activated gel can be heated to a melting temperature T1 to reach a liquid state. After reaching the liquid state, the solution can cool down and transition back to a gel structure at a temperature T2. The gelification temperature T2 can be much lower than the melting temperature T1. As an example, agar gels may exhibit this hysteresis property. For example, a 1.5% w/w agar gel melts at about 85° C. but gelifies at a temperature T2 between about 32° C. and about 45° C. The hysteresis properties of agar may be tailored to the obturation process. For example, a hydrogel such as agar (in liquid form) may be heated and delivered to the root canal system at a temperature larger than T2 such that the hydrogel is in a flowable state sufficient to flow through the treatment region. Heat may be delivered to the obturation material directly by conduction or radiation, or indirectly by, for example, heat absorbing elements inside the material, such as nanoparticles that absorb a specific wavelength of light and produce heat inside the material. As the gel cools down (e.g., if the body temperature is below T2), the solution may gelify within the root canal system or treatment region. Heat may also catalyze a polymerization or curing process in various embodiments.

4. Resin-Based Obturation Materials

In some embodiments, the obturation material may be selected from curable (e.g., hardenable) resin-based materials. The resin-based material may be delivered into the tooth in its uncured, flowable state and may be cured following delivery using a trigger. The trigger may be an external stimulus and may include radiation, e.g. actinic radiation. The trigger may also be thermal energy or mechanical energy, e.g. sonic and/or ultrasonic energy (which may be provided by the pressure wave generator). The trigger may further comprise a chemical reaction, including, but not limited to, a redox reaction to initiate polymerization, e.g., free radical polymerization of ethylenically unsaturated monomers (e.g. acrylate, methacrylate). Chemical triggers may further comprise nucleophiles to initiate anionic polymerization (e.g. cyanoacrylate) and further may comprise acids to initiate cationic (ring-opening) polymerization. Curing may also be achieved through addition polymerization of complementary resin monomers having at least two reactive functional groups. Examples for complementary resin monomers include epoxy-amine systems, epoxy-thiol systems, isocyanate-alcohol (urethane) and isocyanate-amine (polyurea) systems.

In some embodiments, the resin-based obturation material may be delivered by way of a syringe, or any dental or non-dental material delivery device. For example, as explained above, the resin-based obturation material may be delivered using the pressure wave generator 5 disclosed herein. In various embodiments, the resin-based material may be unfilled or may include a particulate filler. Fillers may be used to adjust viscosity and rheological properties of the obturation material. In some arrangements, the filler may also impart radiopacity for verification during or after the obturation procedure. Examples for radiopaque fillers include without limitation barium sulfate, bismuth oxychloride, bismuth subcarbonate, ytterbium fluoride, yttrium fluoride, and the like. Particulate fillers may also be used to advantageously reduce polymerization shrinkage during curing.

In various embodiments, the resin-based material includes monomers having at least one ethylenically unsaturated group. Examples of ethylenically unsaturated groups include vinyl groups, acrylate and/or methacrylate groups. Some resin monomers may comprise at least two ethylenically unsaturated groups. Examples of monomers containing two ethylenically unsaturated groups may include without limitation di(meth)acrylate monomers selected from bisphenol-A diglycidyl dimethacrylate (BisGMA), ethoxylated bisphenol-A dimethacrylate (EBPADMA), triethyleneglycol dimethacrylate (TEGDMA), urethane dimethacrylate (UDMA), and other suitable monomers.

The resin-based material may further include adhesion promoters to increase adhesion of the material to the tooth structure to provide a more efficient seal with the tooth. Adhesion promoters may contain acidic groups including without limitation carboxylic, phosphoric, phosphonic, sulfonic, and sulfinic groups. The adhesion promoter may further be capable of copolymerizing with the other resin components. In some embodiments, the resin-based obturation material may include a photoinitiator system that may be cured after being delivered into the tooth using actinic radiation, e.g. UV and/or visible light. The light source may be a standard dental curing light unit.

In some embodiments, the resin-based material may comprise two components, termed a base material and catalyst, respectively. The resin-based obturation material may be cured chemically through a redox reaction. The catalyst part may include oxidizing species including without limitation peroxides, e.g. organic peroxides. The organic peroxide may be selected from benzoyl peroxide, tert.-butyl hydroperoxide, cumene hydroperoxide, and the like. The base material may also comprise reducing co-initiators. Reducing co-initiators may include amines, e.g. tertiary alkyl and/or aryl amines, thiourea, and the like. The two-part resin-based material may further contain a photoinitiator, as explained above.

5. Moisture Cure Systems

In some embodiment, the obturation material may be hardened by reacting with water or other residual moisture inside the root canal system or treatment region. The water may act as catalyst to initiate the hardening reaction, or the water may be a reactant in stoichiometric or near stoichiometric relative amounts. In some embodiments, the moisture curable material may comprise cyanoacrylate esters of the general formula $CH_2=C(CN)COOR$, where R is a linear or branched alkyl radical, aryl radical, or combinations thereof. The ester group R may further comprise heteroatoms such as oxygen, nitrogen, phosphorus, and sulfur atoms, and combinations thereof. Non-limiting examples of suitable alkyl cyanoacrylates include methyl cyanoacrylate, ethyl cyanoacrylate, butyl cyanoacrylate, branched or linear octyl cyanoacrylate, and the like. In certain embodiments, additives such as plasticizers, inert fillers, and stabilizers may be added. In some embodiments, a radio contrast agent may further be present. Without being bound by theory, the chemical structure of the ester group R may be utilized to adjust the rate of the hardening reaction. It is believed that bulkier R groups provide lower reaction rates, which may increase the setting time. It is further believed that more hydrophilic R groups may facilitate penetration of the uncured liquid into small spaces within the root canal system.

In various embodiments, the moisture curable material may comprise condensation cure silicone. Suitable examples include one-part condensation cure systems, commonly referred to as one-part room temperature vulcanizeable (RTV) silicones. Suitable silicone materials may be selected from silicone prepolymers functionalized with readily hydrolysable groups including without limitation acetoxy ($O(CO)CH_3$), enoxy ($O(C=CH_2)CH_3$), alkoxy (OR; R is an alkyl radical), and oxime ($ON=CR_1R_2$; $R_1$, $R_2$ are identical or different alkyl radicals). Optionally, silanol functionalized silicone prepolymers may further be present. Without being bound by theory, exposure to moisture may lead to hydrolysis of these hydrolysable groups followed by rapid crosslinking. In certain embodiments, the material may further contain radio contrast agents.

In some embodiments, the moisture curable material may be selected from mineral cements. For the purposes of the present disclosure, the term mineral cement includes siliceous, aluminous, aluminosiliceous materials in the presence of calcium species such as calcium oxide, calcium hydroxide, calcium phosphate, and others. These cements may harden through hydration and crystallization of the hydrated species. Non-limiting examples include Portland cement, mineral trioxide aggregate (MTA), calcium aluminate, calcium silicate, and calcium aluminosilicate. In some embodiments, the mineral cement may be provided as a dispersion of the solid cement particles in a non-reactive, water miscible liquid. In some embodiments, additives including radio contrast agents may be present. Optionally, organic modifiers including polymeric modifiers may further be present.

6. Precipitation or Evaporation Hardening Systems

In some embodiments, the obturation material may harden through precipitation. The obturation material can comprise a polymer dissolved in a first solvent. The first solvent can be any suitable material, such as a solvent in which the polymer is substantially soluble or miscible. Hardening of the material can be caused by combining the polymer solution with a second solvent or liquid that is miscible with the first solvent but that does not display appreciable solubility for the polymer, which causes the polymer to precipitate out of solution. Advantageously, the second solvent can comprise water and the first solvent can comprise a water miscible solvent for the polymer. Examples for water miscible solvents include, without limitation, alcohols such as ethanol, iso-propanol, and the like, acetone, dimethyl sulfoxide, and dimethyl formamide. Examples of suitable water-insoluble polymers include without limitation partially hydrolyzed poly(vinyl acetate) and copolymers of vinyl alcohol, vinyl pyrrolidone, or acrylic acid copolymerized with hydrophobic vinyl monomers such as ethylene, propylene, styrene, and the like.

In another embodiment, the obturation material may harden through evaporation. The obturation material may comprise a solution of a polymer in a volatile solvent. After delivery of the material into the tooth, the volatile solvent can be evaporated, leaving behind a solid polymer. Evaporation of the solvent may proceed spontaneously or it may be assisted by any suitable mechanism, such as heating or reduced pressure (e.g., vacuum).

7. Catalytic Cure Systems

In some embodiments, the setting or curing reaction may be induced by adding a suitable catalyst to a catalytically curable composition immediately prior to, during, or immediately following delivery of said composition into the root canal system or treatment region. Appropriate distribution of the catalyst throughout the curable composition may be provided through diffusion or it may be provided through agitation. As explained herein, agitation may advantageously be provided by the pressure wave generator 5 and systems disclosed herein.

In various embodiments, the catalytically curable material can comprise a curable resin mixture. The curable resin mixture may be selected from ethylenically unsaturated monomers. In various embodiments, the ethylenically unsaturated monomers may be selected from (meth)acrylate monomers including acrylate, methacrylate, diacrylate, dimethacrylate, monomers with three or more acrylate or methacrylate functional groups, and combinations thereof. The (meth)acrylate monomers may advantageously be hydrophilic to facilitate penetration of the filling material into small spaces within the root canal system; however, the (meth)acrylate monomers may also be hydrophobic in other arrangements. Examples for particularly suitable (meth) acrylate monomers include without limitation, methyl methacrylate, hydroxyethyl methacrylate, hydroxypropyl methacrylate, hydroxyethoxyethyl methacrylate, poly(ethylene glycol) methacrylate, ethylene glycol dimethacrylate, diethylene glycol dimethacrylate, triethylene glycol dimethacrylate, poly(ethylene glycol) dimethacrylate, hexanediiol dimethacrylate, urethane dimethacrylate, bisphenol-A diglycidyl dimethacrylate (BisGMA), ethoxylated bisphenol-A dimethacrylate, trimethylolpropane trimethacrylate, pentaerythritol tetramethacrylate, ethoxylated trimetgylolpropane trimethacrylate, and their acrylate analogues. The (meth)acrylate monomers may be radically polymerizable. Free radical polymerization may be caused by any suitable catalyst system or combination, including without limitation thermal and redox free radical initiator systems. Examples for thermal free radical initiators include peroxide salts, hydrogen peroxide, and organically substituted peroxides and hydroperoxides, as well as azo compounds. Non-limiting examples for redox free radical initiator systems include peroxide-amine combinations, peroxide-thiourea combinations, peroxide-sulfinic acid combinations, peroxide-ferrous salt combinations, peroxide-cuprous salt combinations, and combinations thereof. One component of the redox initiator system may be part of the liquid catalytically curable composition, and the second component may be added immediately prior to, during, or immediately following delivery.

In some embodiments, radio contrast agents may further be added to the material. The radio contrast agent can advantageously comprises nanoparticles having a mean particle size of less than about 200 nm. Advantageously, the nanoparticles can be substantially non-agglomerated. Suitable nanoparticles may be selected from heavy metal, heavy metal salt, and heavy metal oxide nanoparticles. Examples include without limitation colloidal, silver, gold, platinum, palladium, and tantalum particles, zirconia, yttria, ytterbia, yttrium fluoride, ytterbium fluoride, tungstate, and bismuth oxide particles. In another embodiment, the composition may further contain polymerization mediators including chain-transfer agents, stabilizers, accelerators, and the like. The composition may further comprise rheology modifiers and colorants. In yet another embodiment, the composition may further comprise a photoinitiator system to provide additional light-cure capabilities, thus allowing the practitioner to rapidly seal the coronal aspect of the root canal system.

8. Light Cure Systems

In various embodiments, the setting or curing reaction for the obturation material may be induced by exposing a photo-curable composition to actinic radiation, such as ultraviolet and/or visible light. The obturation material may be delivered into the root canal system through the pressure wave generators and systems disclosed herein, and at least part of the material can be exposed to a source of actinic radiation. Exposure may be direct or indirect by irradiating the material through at least part of the tooth structure.

In some embodiments, the obturation material may be substantially translucent and may further display a refractive index higher than the refractive index of the tooth structure. Without being bound by theory, in such embodiments, the high refractive index material may act as a waveguide material transmitting actinic radiation through internal reflection throughout at least part of the tooth's internal volume. The photo-curable composition may be selected from ethylenically unsaturated monomers with or without the presence of a separate photoinitiator. Examples of suitable ethylenically unsaturated monomers include without limitation (meth)acrylate monomers as described herein. Advantageously, at least part of the monomer composition may comprise high refractive index monomers or additives. The refractive index can be greater than about 1.5, preferably greater than about 1.6. Non-limiting examples of a suitable (meth)acrylic high index monomer include halogen-substituted (meth)acrylates, zirconium (meth)acrylates, hafnium (meth)acrylates, thio-substituted (meth)acrylates such as phenylthiolethyl acrylate and bis(methacryloylthiophenyl)sulfide, and combinations thereof. Optionally, high refractive index nanoparticles having a mean particle size of less than about 200 nm may further be added. Advantageously, the high refractive index nanoparticles can be substantially non-agglomerated. Non-limiting examples of suitable nanoparticles include zirconia and titania colloidal particles; other high refractive index materials may also be suitable. In some embodiments, the photoinitiator system may be selected from type I or type II photoinitiator systems or a combination thereof. Non-limiting examples of type I initiators may include benzoin ethers, benzyl ketals, α-dialkoxy acetophenones, α-hydroxy alkylphenones, α-amino alkylphenones, and acyl phosphine oxides; examples of type II initiators include benzophenone-amine combinations, thioxanthone-amine combinations, α-diketone-amine combinations such as phenyl propanedione-amine and camphorquinone-amine systems, and combinations thereof.

9. Further Examples of Obturation Materials and Combinations

Additional examples of obturation materials are disclosed in Table 1 below. It should be appreciated that the disclosed materials are examples; other suitable combinations of materials and cures may be suitable.

TABLE 1

| Cure Type | Chemistry | Description | Example Benefits |
| --- | --- | --- | --- |
| Two component chemical cure | Epoxy-amine | Component A: hydrophilic diepoxy prepolymer (e.g. PEG-diglycidyl ether) + poly(glycidyl) crosslinker) Component B: hydrophilic polyamine (e.g. PEG diamine) dispersed radio contrast agent | good long term stability hydrophilic nature may facilitate tubule penetration slight expansion by water absorption possible to improve seal |
| Two component chemical cure | Alginate + $Ca^{2+}$ | Component A: sodium alginate solution in water Component B: calcium salt solution Component B can also include Ba or Sr salt for radiopacity | good biocompatibility excess Ca may provide remineralization properties |
| Two component chemical cure | metal oxide-polyacid (polyalkenoate or glass ionomer cement) | Component A: acid-dissolvable metal oxide (e.g. HAp, CaO, ZnO, reactive glass) Component B: polyacid, e.g. poly(acrylic acid) Light curable resin can be added for rapid coronal seal. dispersed radio contrast agent | good biocompatibility remineralizing may be possible hydrophilic for tubule penetration |
| Two component chemical cure | VPS addition silicone | Component A: vinyl poly(siloxane) + Pt catalyst Component B: Hydrosilane crosslinker dispersed radio contrast agent (similar to "Gutta Flow" matrix without dispersed gutta percha particles) | excellent long term stability good biocompatibility |

TABLE 1-continued

| Cure Type | Chemistry | Description | Example Benefits |
| --- | --- | --- | --- |
| One component moisture cure | Cyanoacrylate (CA) | Water inside root canal catalyzes setting reaction; hydrophobic/ hydrophilic balance can be adjusted (within limits) | No additional catalyst needed good tubule penetration may be possible |
| One component moisture cure | Condensation cure silicone (one-part RTV silicone) | silanol-terminated siloxane prepolymer + hydrolysis-sensitive crosslinker dispersed radio contrast agent | No additional catalyst needed good biocompatibility good long term stability |
| One component moisture cure | Refractory cement | calcium silicates, aluminosilicates + radiopaque metal oxide, water miscible carrier liquid; MTA and "bio-ceramics" are similar. | excellent long term stability excellent biocompatibility good dimensional stability bonds to dentin |
| Precipitation or evaporation hardening | Dissolved polymers in water miscible or highly volatile solvents | Contact with water inside the root canal evaporation of volatile solvent causes polymer to precipitate | Non-reactive systems Solvent may facilitate or tubule penetration |
| Catalytic cure | VPS addition silicone | Single part vinyl siloxane + hydrosilane, dispersed radio contrast agent; Pt catalyst delivered into tooth; solvent may be used to control viscosity | excellent long term stability good biocompatibility |
| Catalytic cure | Acrylic/ methacrylic resin | PEG (meth)acrylates, PEG di(meth)acrylates, dispersed radio contrast agent peroxide catalyst delivered by syringe; additional light cure possible to provide rapid coronal seal | excellent long term stability good biocompatibility tunable hydrophilicity to facilitate tubule penetration slight expansion possible through water sorption to compensate for shrinkage |
| Light cure | Acrylic/ methacrylic resin | (meth)acrylate-PEG system with high refractive index (RI) additives (e.g. zirconia nanoparticles) high RI additive may be sufficient to provide radiopacity; RI higher than that of dentin (~1.6) may allow the material to act as wave guide to ensure complete cure | excellent long term stability good biocompatibility tunable hydrophilicity to facilitate tubule penetration slight expansion possible through water sorption to compensate for shrinkage |

B. Obturation Material Removal

In some embodiments, it can be desirable to remove an obturation material that fills a treatment region of the tooth. For example, the clinician may desire to remove the obturation material in order to re-treat the treatment region if the treatment region becomes infected or if the obturation or restoration material is damaged. In some embodiments, the hardened obturation material may be removed using the pressure wave generator 5 disclosed herein. As one example, a fully gelified hydrogel (e.g., a calcium-alginate gel) may be broken down using a treatment handpiece 3 that includes a pressure wave generator 5. A suitable treatment fluid can be supplied to the obturated region of the tooth (e.g., an obturated root canal). The pressure wave generator 5 (which may comprise a liquid jet device) can be activated to propagate pressure waves through the treatment fluid to dissolve the obturation material. As explained herein, the pressure wave generator may also be used to supply the treatment fluid to the obturated region. The pressure waves propagating through the obturation material can assist in agitating, breaking apart, and/or dissolving the obturation material. In other embodiments, the obturation material can be removed via heat, mechanical contact, light, electromagnetic energy, rinsing, suction, etc.

Any suitable treatment fluid may be employed to remove the gelified obturation material. For example the treatment fluid used to remove the obturation material may comprise a solvent specific to the obturation material of interest. In one embodiment, ionically cross-linked hydrogels, such as calcium-alginate gels, may be broken down using a solution of sodium hypochlorite or chelating agents (e.g., EDTA, citric acid, stearic acid). For example, chelating agents may help to break down gels (e.g. ionically cross-linked hydrogels) by breaking the ionic links between molecules, which may be formed using divalent ions. For calcium-based gels, EDTA may be used based on its calcium binding properties. Thus, in some embodiments, EDTA or other treatment fluid may be supplied to the obturated region, and the pressure wave generator 5 can be activated to assist with removing the calcium-based gel.

In various embodiments, two different treatment fluids may be used when removing the obturation material. One treatment fluid may be configured to quickly diffuse within the obturation medium, and the other treatment fluid can be configured to break down the structure of the obturation material matrix. For example, sodium hypochlorite can be used in combination with EDTA.

C. Other Characteristics of Obturation Materials

The obturation materials disclosed herein can include a flowable state and a cured or hardened state. When in the flowable state, the obturation material can be delivered to the treatment region (e.g., root canal). For example the material can be flowable such that it can be delivered into root canals, including into all of the isthmuses and ramifications. The flowability or viscosity of the material may depend at least in part on the method of delivery and agitation that would assist in filling complex and small spaces inside the tooth and root canal system. For example, if the material is delivered by syringe, the obturation material may be less viscous (e.g., more flowable) so that it can penetrate into small spaces (e.g., micron size spaces) without using excessive force that could potentially cause extrusion of materials into the periapical space and potentially harm the patient. Accordingly, a flowable obturation material can advantageously fill small spaces while protecting the patient from injury. In other arrangements, the viscosity of the obturation material can be selected such that the obturation material can form a liquid jet when it passes through a nozzle or orifice. For example, an obturation material used to form a liquid jet may have a viscosity similar to that of water or other treatment fluids (such as EDTA, bleach, etc.). The flowable obturation material can be hardened or cured after it fills the treatment region in order to provide a long-term solution for the patient.

For gel-based materials, an obturation gel in its flowable state (e.g., before gelification) can be efficiently delivered into the root canal system based at least in part on its relatively low viscosity. The gel may be degassed in some arrangements, e.g., substantially free of dissolved gases. In some embodiments, the viscosity of the obturation material may be controlled by adjusting the polymer concentration or the molecular weight of the molecule. In other embodiments, the viscosity of the gel-based obturation material may be controlled by exposing the polymer molecules to specific shear/strain rates. The molecules may be designed and formed in such a way that when the molecules are subjected to high deformation rates, the molecules or chemical links may break and therefore induce a lower apparent viscosity. In some embodiments, the molecules may go back to their original state (repair) when the source of deformation is removed, therefore regaining the higher viscosity.

In various embodiments, the obturation material may be delivered by way of a syringe or any dental or non-dental material delivery device. In some embodiments, the obturation material can be delivered by the handpiece 3 disclosed herein. For example, the pressure wave generator 5 can be used to deliver the obturation material (or various components of the obturation material). When delivered by the pressure wave generator 5, the solution can be passed through a small orifice by way of the handpiece 3. A stream of obturation material can be created, and the obturation material can be delivered within the root canal system (or other treatment region). The resulting flow of obturation material into the root canal system, the broadband frequency pressure waves, or a combination of both, helps to ensure a complete obturation of the root canal system (or treatment region). Thus, in some embodiments, a pressure wave generator 5 (such as a liquid jet device) can be activated before or during obturation to enhance the obturation of the root canal system. The liquid stream of obturation material may be a high velocity stream, and may pass through fluid that is retained at the treatment region. The stream of obturation fluid may be diverted to ensure efficient and safe delivery of material. The obturation material may or may not be degassed, e.g., substantially free of dissolved gases.

The viscosity (flowability) of the material may remain substantially constant or it may vary during the procedure. For example, during the delivery of the material into the tooth, the viscosity may be low, but the viscosity may increase after the filling is completed. The viscosity can be increased during the procedure to stabilize the obturation material in place after completion of the filling procedure. At or near the beginning of the procedure, a flowable liquid obturation material can be used, which can be cured into a semi-solid or solid obturation material after filling is completed.

The viscosity of the material may change automatically or by way of an external trigger or force. The viscosity of the obturation material may change by way of changes in chemical reaction in the material or molecular structure of the material. The external trigger or force may comprise an external stimulus including energy having one or more frequencies, or ranges of frequencies, e.g., in the electromagnetic wave spectrum. For example, in some embodiments, the external trigger may include energy having frequencies or ranges of frequencies at frequencies corresponding to microwaves, UV light, visible light, IR light, sound, audible or non-audible acoustics, RF waves, gamma rays, etc. The trigger may comprise an electrical current safe for a human or mammalian body, a magnetic field, or a mechanical shock. In some embodiments, a clinician or user can engage the external trigger to change the obturation material from a substantially flowable state (e.g., a liquid-like state in some arrangements) to a substantially solid or semi-solid state. For example, when the filling is complete or almost complete, the clinician or user can activate the trigger to convert or change the obturation material to a solid or semi-solid state. In still other embodiments, the obturation material may be configured to cure (set) automatically. The setting and curing may be irreversible and permanent, or the setting and curing may be reversible such that the obturation material can be more easily removed.

In some embodiments, the obturation material may be seeded with another material which can preferentially absorb a specific type of electromagnetic wave or a plurality of electromagnetic waves (or frequencies thereof). For example, near-IR absorbing gold nanoparticles (including gold nanoshells and nanorods) may be used to produce heat when excited by light at wavelengths from about 700 to about 800 nm. In such embodiments, heat may help in reducing the viscosity of the material, rendering it more flowable until the material is delivered and has filled substantially all the spaces inside the tooth and root canals. The material viscosity can then return to its original state as the heat is dissipate.

In another embodiment, the filling material may be seeded by particles of a magnetic material, such as stainless steel. In such an embodiment, the magnetic material may be driven into the root canals and small spaces remotely by way of an external magnet. In another embodiment, the obturation material may be seeded with electrically conductive particles which can help in controlling the delivery of the material. For example, when the obturation material reaches the apex of the root canal, the circuit electrical circuit is completed and the console may signal the operator that the filling process is completed. In yet other embodiments, the obturation material can be made electrically conductive and, through safe electrical currents that are absorbed by the energy absorbing material, heat can be generated. The heat can act to reduce the viscosity of the filling material, rendering it more flowable until the source of energy is stopped and the heat is dissipated. The material can then become more viscous as it cools down until it hardens, for example, as a semi-solid or solid material.

In various arrangements, the obturation material may have a surface tension that is sufficiently low such that the material can flow into small complex (or irregular) spaces inside the tooth. Having a low surface tension can reduce or eliminate air bubbles trapped in the spaces of the canals or tooth. In some embodiments, the obturation material can be radiopaque. Radiopaque obturation materials can allow the clinician to monitor the location and quality of obturation material inside the tooth. Radiopaque obturation materials may also be used to alert the doctor or clinician in the future about which teeth have received root canal treatment(s) in the past.

The obturation material may comprise a biocompatible material configured to minimize or reduce any negative effects that the filling or obturation material may have on the body. For example, the obturation material can be designed to prevent the growth of bacteria, biofilms, parasites, viruses, microbes, spores, pyrogens, fungi or any microorganisms that may trigger patient/body reactions or infections/diseases. For example, the growth of bacteria or biofilms may be prevented or reduced by way of an antibacterial agent that is designed such that it kills bacteria while not inducing bacterial resistance to such agent. The antibacterial agent may be suitable for in vivo use and can be configured such that it does not induce unwanted body/patient reactions. The antibacterial agent may also be designed such that it does not react with the various components of the obturation material. In some embodiments, the antibacterial agent may be designed such that it is soluble or miscible in the obturation material. The antibacterial agent may be combined with other agents (e.g. surfactants, polymers, etc.) to increase its potency and efficiency. In some embodiments, the antibacterial agent can be encapsulated in a coating. In some arrangements, the antibacterial agent may be replaced or supplemented by antiparasitic agents, antiviral agents, antimicrobial agents, antifungal agents or any agents that may prevent development of infections/diseases or patient/body reactions.

Moreover, the obturation material may be configured to be naturally absorbed by the body over time. The absorption of the obturation material may occur in combination with pulp tissue regeneration that helps the pulp tissue to grow and fill the root canal space as the filling material is absorbed. In some cases, the obturation material may be absorbed without any pulp tissue regeneration. In some cases, the obturation material may not be absorbed by the patient's body. The obturation materials disclosed herein can also be configured to bond securely to dentin. Bonding to dentin can help provide a better seal, which can then reduce the rate and extent of penetration of contaminants and bacteria.

Some obturation materials disclosed herein (e.g. long chain polymers or cross-linked polymer networks) may have a certain molecular structure, or may be seeded by such a material, that causes a reduction of viscosity of the material (making them more flowable) when under the application of shear forces. This reduction in viscosity may be reversible or irreversible. The reversing mechanism can be automatic or by way of an external trigger or chemical reaction. If the reduction of viscosity is reversible, the reversing time may be adjustable to allow for the time required for filling the teeth.

In some arrangements, shear-thinning behavior can usually be observed when in the presence of various configurations, such as a solution of long chain polymers or a cross-linked polymer (e.g. short chain) network. When in the presence of long chain polymers, the molecular network of the obturation material can be subjected to a shear flow that can evolve from an entangled state to a more structured orientation that follows the main direction of the flow. The alignment can reduce the apparent resistance of the fluid to the driving force (e.g., can exhibit lower viscosity) due to the untangling of the polymer molecules. The fluid may therefore exhibit shear thinning behavior. When the amount of strain applied to the fluid is sufficient, the change in the fluid properties can be reversible. The relaxation time of the molecules may drive the time it takes for the fluid to go back to its original state.

When in the presence of a cross-linked polymer network, each polymer molecule of the obturation material can be linked to its neighboring molecules (e.g., by cross-linking, typically covalent or ionic bonds). When subjected to a shear flow, the links between the molecules may be broken and the polymer molecules can move "freely" into solution, hence leading to a lower apparent viscosity. If the links can be reformed (e.g., via heat, pH, etc . . . ), the process may be reversible. If the network cannot be reformed, the process may be irreversible.

When subjected to a large enough deformation, polymer molecules of the obturation material may break. The breakage may lead to a drop in apparent viscosity (shear thinning). Such large-deformation processes may be irreversible.

IV. Examples of Test Results

Figure 9A:
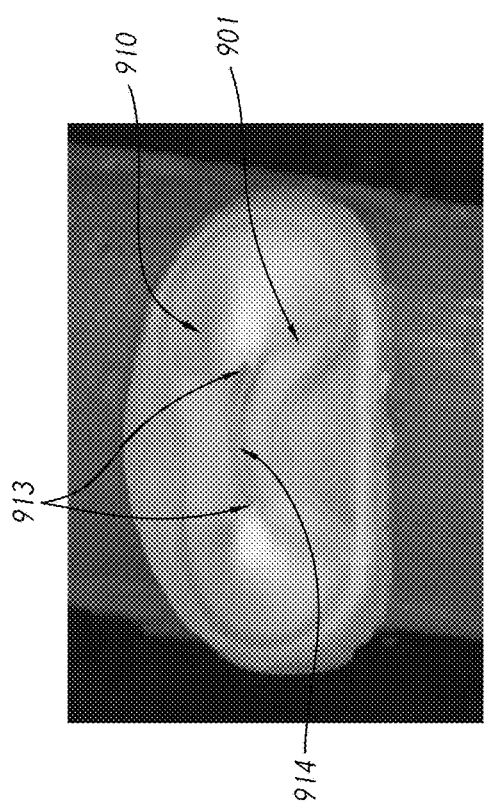
FIG. 9A is a photograph illustrating a cross-sectional view of an obturated root canal that was filled in a procedure in accordance with various embodiments disclosed herein.
Figure 9B:
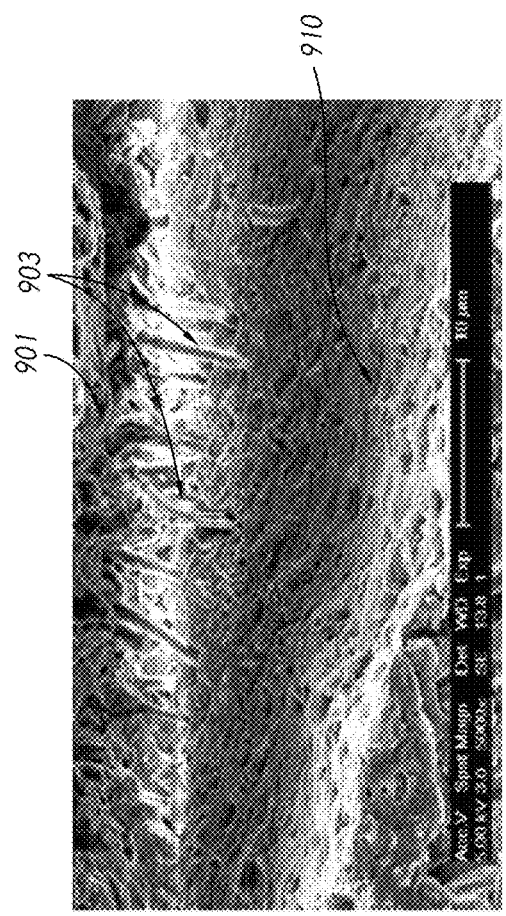
FIG. 9B is a scanning electron micrograph of a split, obturated root that was filled in the procedure of FIG. 9A.

FIG. 9A is a photograph illustrating a top cross-sectional view of obturated root canals 913 of a tooth 910 that was filled in a procedure in accordance with various embodiments disclosed herein. As shown in FIG. 9A, a narrow isthmus 914 (e.g., which may be as narrow as about 10-20 microns) can connect the canals 913. It should be appreciated that other obturation procedures may not be able to effectively fill such narrow, irregular and complex isthmuses 914. FIG. 9B is a scanning electron micrograph of a split, obturated root that was filled in the procedure of FIG. 9A. The root canals 913 in the test of FIGS. 9A-9B was filled using a treatment handpiece similar to those disclosed in FIGS. 4A-8D. In FIG. 9B, the tooth 910 (e.g., walls of the canals 913) are shown at the bottom of the image, and the obturation material 901 is shown at the top of the image. For the test conducted in accordance with FIGS. 9A-9B, the obturation material comprised a catalytically curable resin-based material delivered using a handpiece comprising a liquid jet device.

In this example, a filling material composition, referred to as a base resin, was prepared by combining 49 parts by weight of 2-hydroxyethyl methacrylate, 43 parts by weight of poly(ethylene glycol) dimethacrylate, 5 parts by weight of triethyleneglycol dimethacrylate, and 5 parts by weight of N,N-di(hydroxyethyl)-p-toluidine. The mixture was degassed prior to being delivered to the root canal. A separate catalyst resin mixture was prepared by combining 19 parts by weight of poly(ethylene glycol) dimethacrylate and 1 part by weight of dibenzoyl peroxide. Extracted human molars were prepared with an endodontic access opening and the root canal systems were cleaned using a handpiece with a liquid jet device. The base resin was delivered into the root canal system by way of the jet device, e.g., the base resin was routed through a small orifice at a proximal portion of a guide tube. The stream of base resin material was delivered within the root canal system. Subsequently, a small volume (about the same or less than the volume of base resin within the root canal system) of the catalyst resin was injected through the endodontic access opening into the pulp chamber by syringe, followed by additional delivery of base resin via the jet device. The combined composition hardened within less than about 3 minutes throughout the entire root canal system.

In the test associated with FIGS. 9A-9B, the root canals 913 and isthmuses 914 were fully filled with obturation material 901. The obturation material 901 was uniformly hardened and void-free throughout the entire canal system. As shown in FIG. 9B, the sectioned, obturated roots were further examined using scanning electron microscopy imaging, which reveals the obturation material filling several micrometers into dentinal tubules. The sample was desiccated prior to imaging, which caused the material filling the tubules to be removed from the tubules. The imaged strings 903 shown in FIG. 9B represent the filling material 901 that filled the tubules and small spaces of the tooth. Thus, as shown in FIGS. 9A-9B, the pressure wave generator 5 disclosed herein can effectively and fully fill a root canal system of a tooth, including small spaces in the tooth such as dentinal tubules.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. A dental apparatus comprising:
   a handpiece having a distal portion to be positioned at a treatment region of a tooth, the handpiece further comprising a first fluid supply line and a second fluid supply line to deliver fluid to the treatment region; and
   a pressure wave generator configured to generate pressure waves through the treatment region to cause a filling material to substantially fill the treatment region,
   wherein the apparatus is configured to deliver a first composition through the first fluid supply line and a second composition through the second fluid supply line to the treatment region, and
   wherein the apparatus is further configured to combine the first composition with the second composition at a location in the handpiece or at the treatment region of the tooth to form the filling material to substantially fill the treatment region.

2. The dental apparatus of claim 1, wherein the pressure wave generator comprises a first pressure wave generator in communication with the first fluid supply line and a second pressure wave generator in communication with the second fluid supply line.

3. The dental apparatus of claim 1, further comprising a console to be in fluid communication with the handpiece, the console comprising one or more pumps to drive the first and second compositions to the handpiece.

4. The dental apparatus of claim 3, wherein the console comprises a controller configured to change the handpiece from a cleaning mode to a filling mode or from the filling mode to the cleaning mode.

5. The dental apparatus of claim 3, wherein the console comprises one or more reservoirs to store the first and second compositions.

6. The dental apparatus of claim 1, wherein the handpiece comprises one or more reservoirs to store the first and second compositions.

7. The dental apparatus of claim 6, wherein the one or more reservoirs is disposed in or on the handpiece.

8. The dental apparatus of claim 7, wherein the one or more reservoirs is removable from the handpiece.

9. The dental apparatus of claim 1, further comprising an interface member configured to couple to a conduit in fluid communication with a console, the handpiece configured to removably engage with a distal portion of the interface member.

10. The dental apparatus of claim 9, further comprising a cartridge configured to couple with the distal portion of the interface member, the handpiece configured to removably engage with a distal portion of the cartridge, the cartridge comprising one or more reservoirs configured to store the first and second compositions.

11. The dental apparatus of claim 10, wherein the cartridge is configured to removably engage with the interface member.

12. The dental apparatus of claim 10, wherein the cartridge comprises a supply line, the supply line coiled within the cartridge.

13. The dental apparatus of claim 1, wherein the pressure wave generator comprises a liquid jet device.

14. The dental apparatus of claim 13, wherein the liquid jet device comprises a guide tube and an opening disposed near a distal portion of the guide tube.

15. The dental apparatus of claim 1, further comprising a cap near the pressure wave generator, the cap at least partially defining a chamber, the cap configured to retain fluid in the chamber when the cap is positioned against the treatment region.

16. The dental apparatus of claim 1, wherein the pressure wave generator is coupled to or formed with the handpiece.

17. The dental apparatus of claim 16, wherein the pressure wave generator comprises a filling mode in which the pressure wave generator fills the treatment region and a cleaning mode in which the pressure wave generator cleans the treatment region.

18. The dental apparatus of claim 17, wherein the handpiece comprises a switch to switch between the filling mode and the cleaning mode.

19. The dental apparatus of claim 16, further comprising a console in fluid communication with the handpiece, the console configured to control the operation of a treatment procedure.

20. The dental apparatus of claim 19, wherein the one or more reservoirs is disposed in or on the console.

21. The dental apparatus of claim 1, wherein one of the first and second compositions comprises water.

22. The dental apparatus of claim 1, further comprising the first composition.

23. The dental apparatus of claim 1, wherein the pressure wave generator is further configured to deliver cleaning fluid through an opening and to generate pressure waves through the treatment region to cause the cleaning fluid to substantially clean the treatment region.

24. The dental apparatus of claim 1, further comprising a cartridge configured to couple with the handpiece, wherein the cartridge comprises the first supply line and the second supply line, the cartridge comprising a switch to switch between the first and second supply lines.

25. The dental apparatus of claim 1, wherein the apparatus is configured to operate in a cleaning mode in which cleaning fluid passes through an opening to clean the treatment region, and
   wherein the apparatus is configured to operate in a filling mode in which the filling material passes through the opening to fill the treatment region.

26. The dental apparatus of claim 1, wherein the pressure wave generator comprises an opening to deliver at least one of the first composition, the second composition, and the filling material to the treatment region.

27. The dental apparatus of claim 1, wherein the pressure wave generator is further configured to substantially clean the treatment region.

* * * * *